(12) United States Patent
Sibilia

(10) Patent No.: US 10,309,966 B2
(45) Date of Patent: Jun. 4, 2019

(54) PERSONALIZED THERAPY OF INFLAMMATION-ASSOCIATED CANCER USING METHODS OF ASSESSING THE SUSCEPTIBILITY OF A SUBJECT TO THE TREATMENT WITH EGFR INHIBITORS/ANTAGONISTS

(71) Applicant: Medizinische Universität Wien, Vienna (AT)

(72) Inventor: Maria Sibilia, Vienna (AT)

(73) Assignee: Medizinische Universität Wien, Vienna (AT)

( * ) Notice: Subject to any disclaimer, the term of this patent is extended or adjusted under 35 U.S.C. 154(b) by 0 days.

(21) Appl. No.: 15/312,252

(22) PCT Filed: May 21, 2015

(86) PCT No.: PCT/EP2015/061220
§ 371 (c)(1),
(2) Date: Nov. 18, 2016

(87) PCT Pub. No.: WO2015/177266
PCT Pub. Date: Nov. 26, 2015

(65) Prior Publication Data
US 2017/0184595 A1    Jun. 29, 2017

(30) Foreign Application Priority Data
May 22, 2014    (EP) .................................. 14169512

(51) Int. Cl.
G01N 33/574    (2006.01)
G01N 33/50    (2006.01)

(52) U.S. Cl.
CPC .. *G01N 33/57419* (2013.01); *G01N 33/57438* (2013.01); *G01N 2333/71* (2013.01); *G01N 2800/50* (2013.01); *G01N 2800/7095* (2013.01)

(58) Field of Classification Search
None
See application file for complete search history.

(56) References Cited

PUBLICATIONS

Dube et al., Epidermal growth factor receptor inhibits colitis-associated cancer in mice, J. Clin. Invest. 122(8): 2780-2792, Aug. 2012.*
Wu et al., Molecular mechanisms underlying chronic inflammation-associated cancers, Canc. Lett. 345:164-173, 2014.*
Chen et al., "Gefitinib as an effective therapy for advanced hepatocellular carcinoma with lung metastasis?" *Liver Int.*, 30(10):1548-1549, 2010.

(Continued)

*Primary Examiner* — Claire Kaufman
(74) *Attorney, Agent, or Firm* — Parker Highlander PLLC

(57) ABSTRACT

The present invention relates to in vitro methods of assessing the susceptibility or responsiveness of a subject to the treatment with an epidermal growth factor receptor (EGFR) inhibitor/antagonist, wherein the subject has been diagnosed or suspected of suffering from inflammation-associated cancer. These methods comprise determining the level of expression of EGFR in myeloid cells in a sample from the subject, wherein an expression of EGFR in the myeloid cells is indicative of the subject being susceptible to the treatment with an EGFR inhibitor/antagonist.

Figure 1:
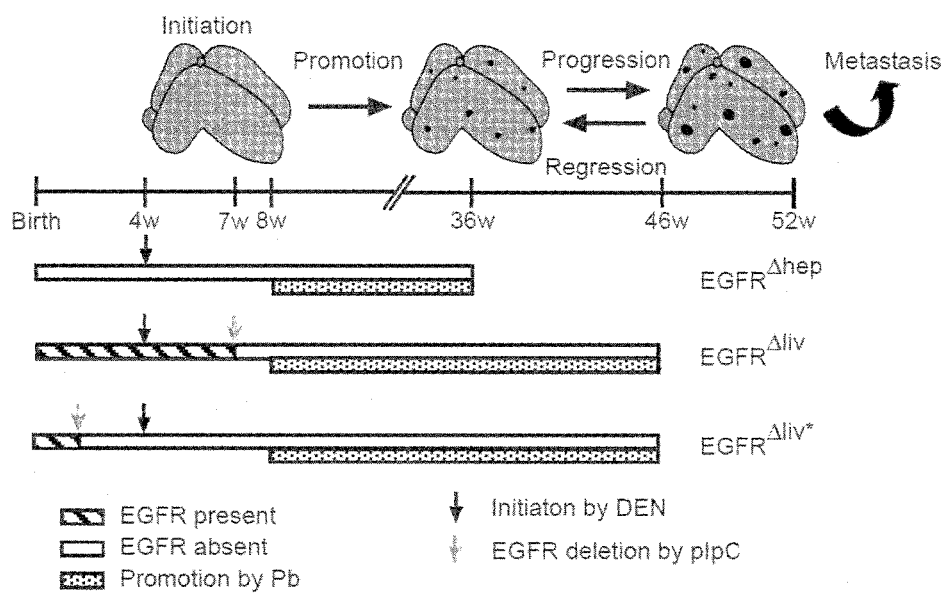
Figure 1:
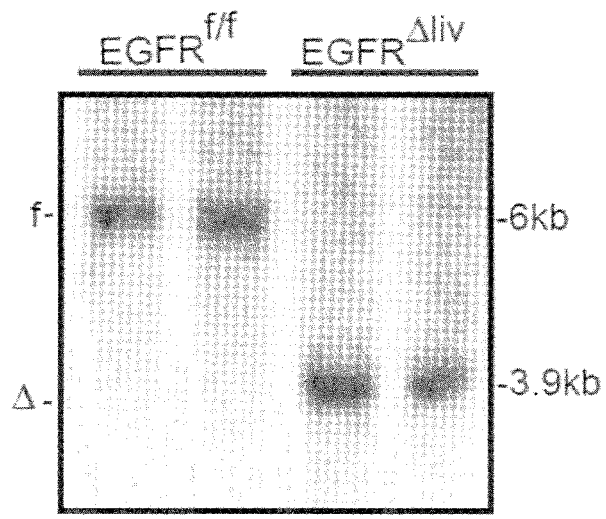
Figure 1:
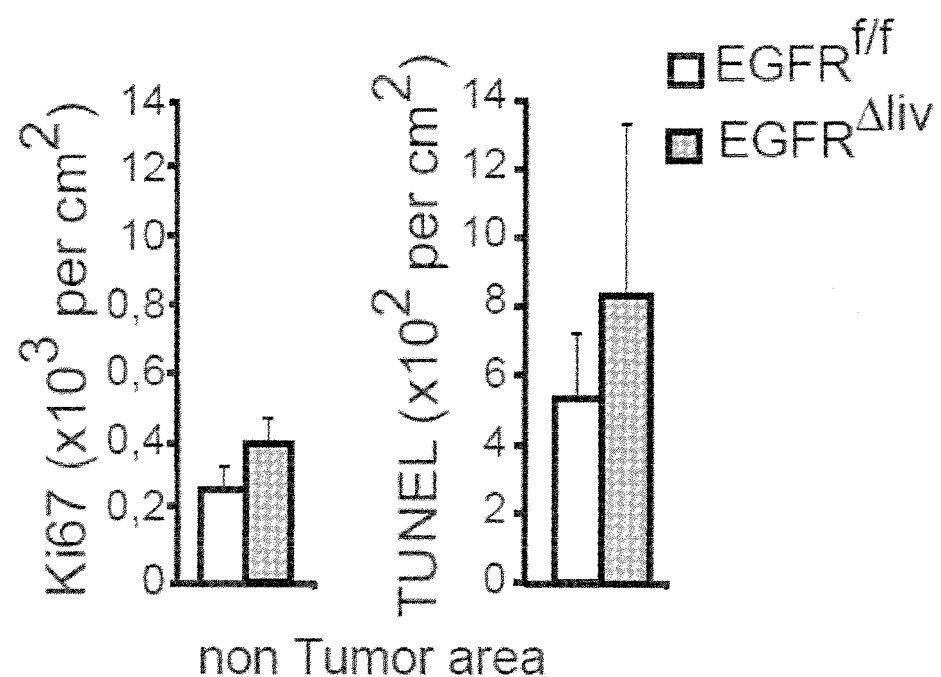
Figure 1:
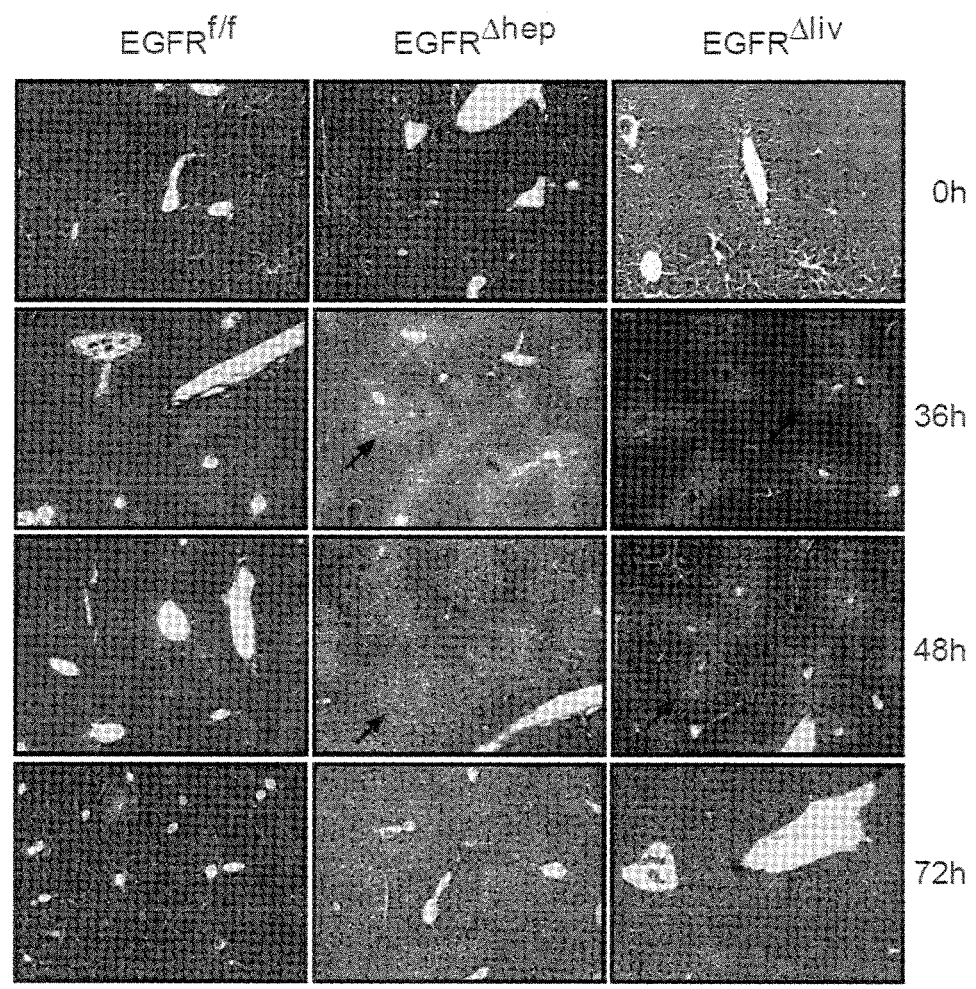
Figure 1:
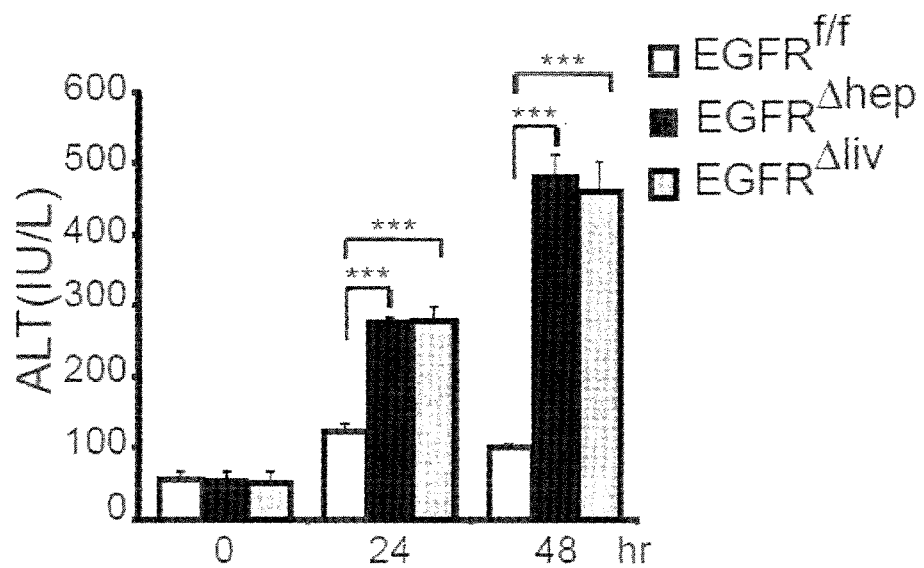
Figure 1:
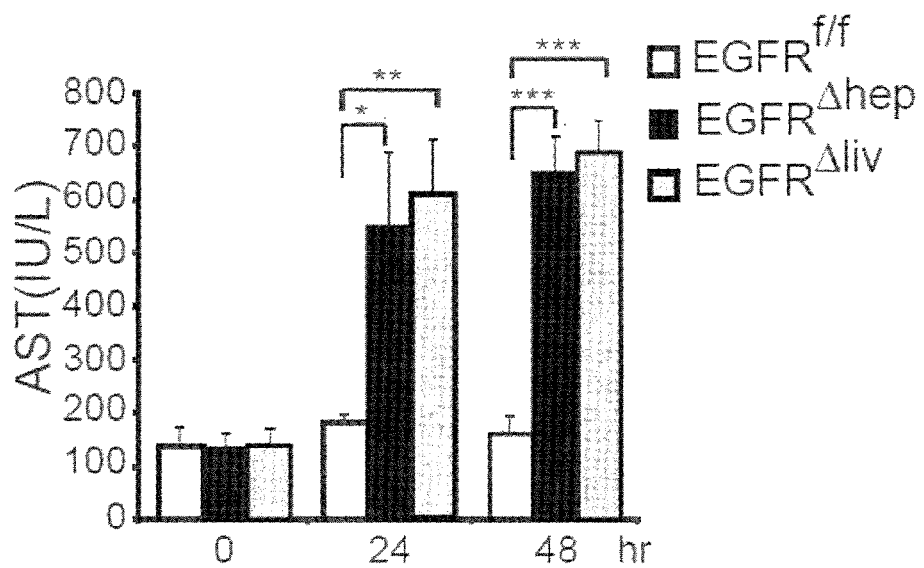
Figure 1:
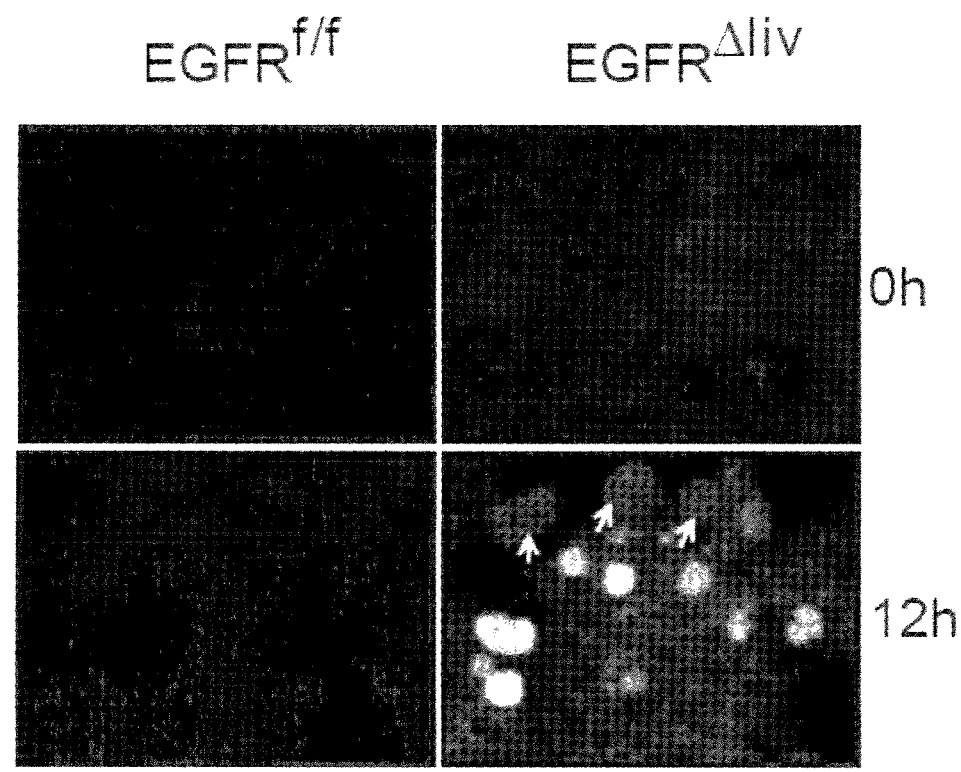
Figure 1:
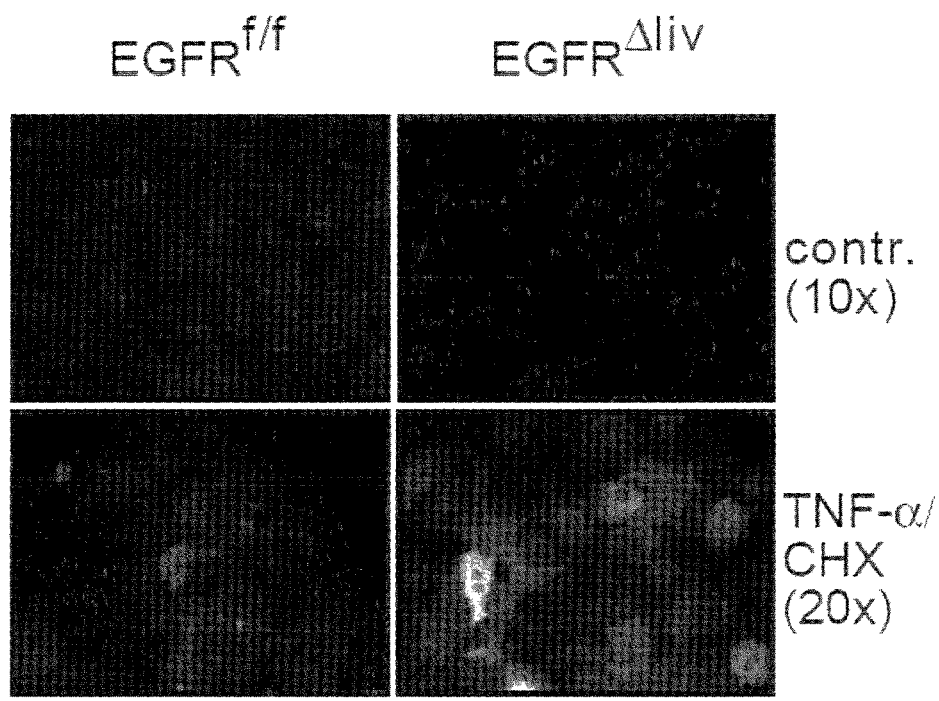
Figure 1:
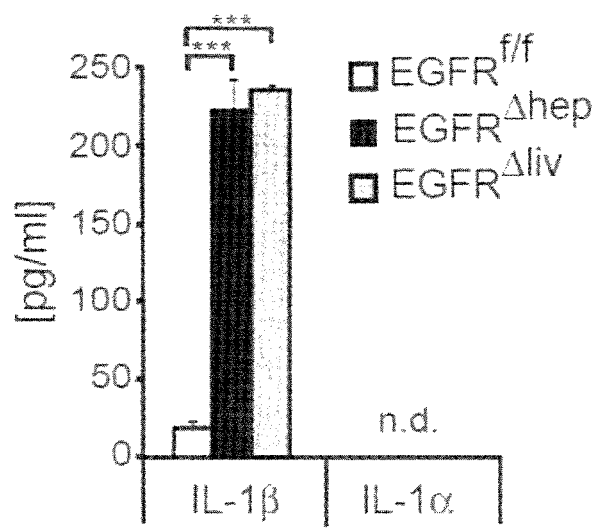

15 Claims, 67 Drawing Sheets
Specification includes a Sequence Listing.

(56) References Cited

PUBLICATIONS

Hoechst et al., "A New Population of Myeloid-Derived Suppressor Cells in Hepatocellular Carcinoma Patients Induces CD4<+>CD25<+>Foxp3<+> T Cells," *Gastroenterology*, 135(1):234-243, 2008.

International Search Report and Written Opinion issued in corresponding PCT Application No. PCT/EP2015/061220, dated Aug. 3, 2015.

Murdoch et al., "The role of myeloid cells in the promotion of tumour angiogenesis," *Nat. Rev. Cancer*, 8(8):618-631, 2008.

Wiedmann et al., "Molecular Targeted Therapy of Hepatocellular Carcinoma—Result of the First Clinical Studies," *Curr. Cancer Drug Targets*, 11(6):714-733, 2011.

\* cited by examiner

A)

B)

c)

D)

E)

F)

G)

H)

I)

A)

B)

C)

D)

E)

F)

G)

H)

I)

J)

A)

B)

C)

D)

E)

F)

A)

B)

C)

D)

E)

A)

B)

C)

D)

E)

F)

G)

H)

l)

J)

K)

L)

M-P)

A)

B)

C)

D)

E)

F)

G)

A)

B)

C)

D)

E)

F)

G)

H)

I)

J)

A)

B)

C)

D)

E)

F)

G)

A)

B)

C)

A)

B)

C)

D)

E)

F)

A)

B)

C-F)

A-D)

A)

F)

G)

D)

E)

F)

A-C)

B)

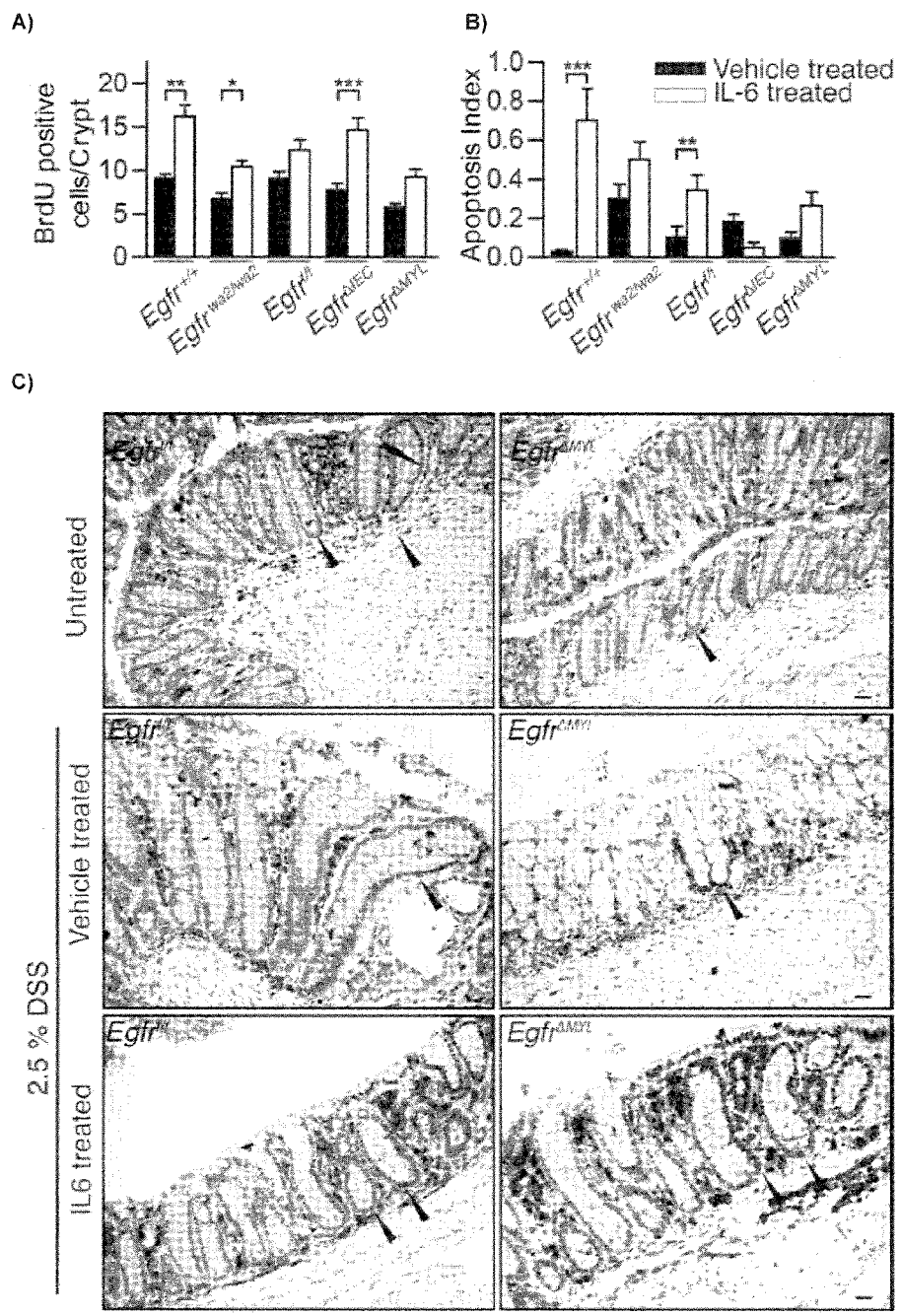

D)

A) B)

c)

D)

A)

B)

C)

D)

E)

A-B)

C)

A)

B)

A-B)

A)

B)

A-B)

SEQUENCE LISTING

```
<160> NUMBER OF SEQ ID NOS: 33

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220
```

```
Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640
```

```
Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg His
660                 665                 670

Ile Val Arg Lys Arg Thr Leu Arg Arg Leu Leu Gln Glu Arg Glu Leu
    675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
                915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
            995                 1000                 1005

Asp Val Val Asp Ala Asp Glu  Tyr Leu Ile Pro Gln  Gln Gly Phe
   1010                 1015                 1020

Phe Ser Ser Pro Ser Thr Ser  Arg Thr Pro Leu Leu  Ser Ser Leu
   1025                 1030                 1035

Ser Ala Thr Ser Asn Asn Ser  Thr Val Ala Cys Ile  Asp Arg Asn
   1040                 1045                 1050

Gly Leu Gln Ser Cys Pro Ile  Lys Glu Asp Ser Phe  Leu Gln Arg
```

```
              1055                1060                1065
Tyr Ser  Ser Asp Pro Thr Gly Ala Leu Thr Glu Asp  Ser Ile Asp
             1070                1075                1080

Asp Thr  Phe Leu Pro Val Pro Glu Tyr Ile Asn Gln  Ser Val Pro
             1085                1090                1095

Lys Arg  Pro Ala Gly Ser Val Gln Asn Pro Val Tyr  His Asn Gln
             1100                1105                1110

Pro Leu  Asn Pro Ala Pro Ser Arg Asp Pro His Tyr  Gln Asp Pro
             1115                1120                1125

His Ser  Thr Ala Val Gly Asn Pro Glu Tyr Leu Asn  Thr Val Gln
             1130                1135                1140

Pro Thr  Cys Val Asn Ser Thr Phe Asp Ser Pro Ala  His Trp Ala
             1145                1150                1155

Gln Lys  Gly Ser His Gln Ile Ser Leu Asp Asn Pro  Asp Tyr Gln
             1160                1165                1170

Gln Asp  Phe Phe Pro Lys Glu Ala Lys Pro Asn Gly  Ile Phe Lys
             1175                1180                1185

Gly Ser  Thr Ala Glu Asn Ala Glu Tyr Leu Arg Val  Ala Pro Gln
             1190                1195                1200

Ser Ser  Glu Phe Ile Gly Ala
             1205                1210

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
cccagaaatg ccagattacg                                           20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
gcaaacatac gcaagggatt                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
gagggatgaa attcctgcaa                                           20

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gcctgtgtcc gggtctcgtc g                                         21
```

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
caaccagtgc acctagcctg gc                                              22

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gggcctcaaa ggaaagaatc                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
taccagttgg ggaactctgc                                                 20

<210> SEQ ID NO 9
<211> LENGTH: 26
<212> TYPE: DNA
<213> ORGANISM: Artificial Sequence
<220> FEATURE:
<223> OTHER INFORMATION: Synthetic primer

<400> SEQUENCE: 9
caccttacac ctaccagagt gatttg                                          26

<210> SEQ ID NO 10
<211> LENGTH: 24
<212> TYPE: DNA
<213> ORGANISM: Artificial Sequence
<220> FEATURE:
<223> OTHER INFORMATION: Synthetic primer

<400> SEQUENCE: 10
tgttgcaggt catttaacca agtg                                            24

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
ttccatccag ttgccttctt gg                                              22

<210> SEQ ID NO 12
<211> LENGTH: 23
<212> TYPE: DNA
<213> ORGANISM: Artificial Sequence
<220> FEATURE:

<223> OTHER INFORMATION: Synthetic primer

<400> SEQUENCE: 12
ttctcatttc cacgatttcc cag                                          23

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
accagtggag aatcccctat ac                                           22

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
gccaagactg tagtgtggtc a                                            21

<210> SEQ ID NO 15
<211> LENGTH: 19
<212> TYPE: DNA
<213> ORGANISM: Artificial Sequence
<220> FEATURE:
<223> OTHER INFORMATION: Synthetic primer

<400> SEQUENCE: 15
tctgggtacg tgggtgttc                                               19

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
acaggtgata atgaggacag cc                                           22

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
ggtcttaggc tcaggccatt a                                            21

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
cgcttatggt ggaaacctct c                                            21

```
<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
caccgagaaa gaaggatgga                                               20

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
tcacggttgt gctgataact g                                             21

<210> SEQ ID NO 21
<211> LENGTH: 19
<212> TYPE: DNA
<213> ORGANISM: Artificial Sequence
<220> FEATURE:
<223> OTHER INFORMATION: Synthetic primer

<400> SEQUENCE: 21
gacgagcaaa ctccctcct                                                19

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
atcaagcaga ccaccaggat                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
accactttgg tgcctttcgt                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
gtcgcagact gtagatccct                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 25
agacgtgctg actgtgcaac                                           20

<210> SEQ ID NO 26
<211> LENGTH: 22
<212> TYPE: DNA
<213> ORGANISM: Artificial Sequence
<220> FEATURE:
<223> OTHER INFORMATION: Synthetic primer

<400> SEQUENCE: 26
ccgtgtgatt tcgagtgaga ga                                        22

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
cccaggcaac gtatcaaagt                                           20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
ggtcataccc aggaaagcaa                                           20

<210> SEQ ID NO 29
<211> LENGTH: 21
<212> TYPE: DNA
<213> ORGANISM: Artificial Sequence
<220> FEATURE:
<223> OTHER INFORMATION: Synthetic primer

<400> SEQUENCE: 29
agaagcatgg ggaggactac a                                         21

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
gtcgttgttc atcactggcg                                           20

<210> SEQ ID NO 31
<211> LENGTH: 21
<212> TYPE: DNA
<213> ORGANISM: Artificial Sequence
<220> FEATURE:
<223> OTHER INFORMATION: Synthetic primer

<400> SEQUENCE: 31
gcctgtgtcc gggtctcgtc g                                         21

<210> SEQ ID NO 32
<211> LENGTH: 21

```
<212> TYPE: DNA
<213> ORGANISM: Artificial Sequence
<220> FEATURE:
<223> OTHER INFORMATION: Synthetic primer

<400> SEQUENCE: 32
caaccagtgc acctagcctg g                                          21

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
aagtttaaga aacccgctc tact                                        24
```

PERSONALIZED THERAPY OF INFLAMMATION-ASSOCIATED CANCER USING METHODS OF ASSESSING THE SUSCEPTIBILITY OF A SUBJECT TO THE TREATMENT WITH EGFR INHIBITORS/ANTAGONISTS

This application is a national phase application under 35 U.S.C. § 371 of International Application No. PCT/EP2015/061220, filed May 21, 2015, which claims benefit of European Application No. EP 14169512.2, filed May 22, 2014, the entire contents of each of which are hereby incorporated by reference.

The present invention relates to in vitro methods of assessing the susceptibility or responsiveness of a subject to the treatment with an epidermal growth factor receptor (EGFR) inhibitor/antagonist, wherein the subject has been diagnosed as suffering from inflammation-associated cancer or is suspected of suffering from inflammation-associated cancer, such as hepatocellular carcinoma (HCC) or colorectal cancer. These methods comprise a step of determining the level of expression of EGFR in myeloid cells in a sample obtained from the subject, wherein an expression of EGFR in the myeloid cells is indicative of the subject being susceptible or responsive to the treatment with an EGFR inhibitor/antagonist. The invention also relates to an EGFR inhibitor/antagonist for use in the treatment or amelioration of inflammation-associated cancer, such as HCC or colorectal cancer, in a subject that has been identified in the aforementioned methods as being susceptible or responsive to such treatment. The invention furthermore provides in vitro methods of prognosing the survival time, the progression-free survival time or the disease course of a subject that has been diagnosed as suffering from inflammation-associated cancer or is suspected of suffering from inflammation-associated cancer, which methods also rely on determining the expression of EGFR in myeloid cells in a sample obtained from the subject. In addition thereto, the invention relates to in vitro diagnostic methods of assessing the proneness of a subject to develop inflammation-associated cancer, such as colorectal cancer, wherein the expression of EGFR in myeloid cells in a sample from the subject is determined. The invention further provides an EGFR inhibitor/antagonist for use in the prevention of inflammation-associated cancer in a subject that has been identified in the aforementioned diagnostic methods as being prone to develop inflammation-associated cancer.

Inflammation-associated cancer, such as hepatocellular carcinoma (HCC) or colorectal cancer, poses a serious threat to human health. HCC, for example, is the sixth most frequent cancer with limited treatment options and poor prognosis. Moreover, HCC is the third most common cause of cancer-related mortality worldwide and represents the fastest growing cause of cancer-related death (Jemal, A. et al., 2011). The main risk factors for HCC include hepatitis B or C virus infection, alcoholic liver injury, non-alcoholic steatohepatitis, environmental carcinogens and hereditary metabolic diseases (Whittaker, S. et al., 2010). HCC almost inevitably develops in the setting of chronic hepatitis or cirrhosis, conditions regarded as preoplastic stages (Laurent-Puig, P. et al., 2006). HCC is a tumor with very heterogeneous biology and etiology, growth dynamics and outcome. Although therapeutic approaches to HCC have been proposed (e.g., Wiedmann, M. W. et al., 2011; Chen, W. C. et al., 2010; and Hoechst, B. et al., 2008), current treatment options are limited, which may be due in part to the lack of tissue markers for patient stratification for individualized treatment. Indeed, there is a limited use of liver biopsies for HCC diagnosis, which is largely based on radiological criteria (EASL-EORTC clinical practice guidelines: management of hepatocellular carcinoma, 2012). Biomarker based individualized drug treatment has recently brought major breakthroughs in previously poorly controlled malignancies such as lung and breast cancer. Therefore, more work is urgently needed to better understand the relevant biological mechanisms driving HCC development and progression.

Adding to disease complexity is the known role of various non-tumor cells in HCC development. It is known that persistent infection, activation of resident liver macrophages (Kupffer cells) and recruitment of inflammatory cells lead to chronic inflammation (Finkin, S. et al., 2011; Luedde, T. et al., 2007; Sakurai, T. et al., 2006; Vainer, G. W. et al., 2008) accompanied by the production of cytokines, chemokines and growth factors favoring HCC development (Coussens, L. M. et al., 2002). However, the molecular link between inflammation and HCC is not completely understood. Cytokines such as IL-6 and IL-1 play a central role in liver carcinogenesis. IL-6 is produced by Kupffer cells following stimulation with IL-1, which is released by dying hepatocytes (Grivennikov, S. I. et al., 2010; Sakurai, T. et al., 2008). IL-6 is responsible for compensatory proliferation of damaged hepatocytes leading eventually to HCC development (Naugler, W. E. et al., 2007). Possible roles of myeloid cells including macrophages in connection with tumor angiogenesis have also been described (Murdoch, C. et al., 2008).

Many signaling pathways have been suggested to play a role in HCC development. Genetic studies in mice have shown that MyD88, JNK1/2, p38α and IKKβ can drive HCC development, and their deletion in parenchymal versus non-parenchymal cells can differentially affect hepatocarcinogenesis (Sakurai, T. et al., 2006; Grivennikov, S. I. et al., 2010; Naugler, W. E. et al., 2007; Das, M. et al., 2011; Heinrichsdorff, J. et al., 2008; Hui, L. et al., 2007; Hui, L. et al., 2008; Maeda, S. et al., 2005). JNK1, p38 and IKKβ have also been shown to be involved in human HCC (Hui, L. et al., 2008; Li, H. P. et al., 2013; Wang, S. N. et al., 2012). Moreover, these signaling molecules can regulate IL-6 production in the liver, although the mechanisms are unclear.

EGFR signaling has also been linked with HCC pathogenesis. EGFR is overexpressed in 40-70% of human HCCs (Buckley, A. F. et al., 2008), and elevated expression of the EGFR ligand TGFα has been reported in preoplastic lesions suggesting a role for EGFR signaling in early HCC (Feitelson, M. A. et al., 2004). EGFR antagonists have been shown to be effective in human HCC cells and have demonstrated therapeutic efficacy in a preventive trial in a rat HCC model (Hopfner, M. et al., 2004; Schiffer, E. et al., 2005). However, in a therapeutic trial conducted in xenograft models with human HCC cells, it has been observed that erlotinib treatment was ineffective in reducing HCC burden and even combination therapy with sorafenib did not show any synergistic effect (W. Sieghart, unpublished results). So far clinical trials with EGFR inhibitors have also shown only modest activity, which might be due to unselected patient populations and advanced stages of HCC. Erlotinib showed moderate effects (disease stabilization at 6 months) in phase 2 trials, whereas gefitinib and cetuximab have so far provided only disappointing clinical results in advanced stage HCC patients (Whittaker, S. et al., 2010). Moreover, the SEARCH trial, by far the largest and only phase III study performed, was unable to show any improvement in survival through the addition of erlotinib in advanced stage HCC-patients (Mallarkey, G. et al., 2013).

In view of these unsatisfactory therapeutic results achieved with EGFR inhibitors/antagonists so far, there is an urgent need for a better understanding of the mechanisms whereby EGFR signaling influences the progression of inflammation-associated cancer such as HCC and, accordingly, for an improved personalized therapy of inflammation-associated cancer based on the purposive use of EGFR inhibitors/antagonists.

It is therefore an object of the present invention to provide an improved personalized therapy of inflammation-associated cancer, particularly HCC or colorectal cancer. Moreover, it is also an object of the invention to provide improved methods of assessing the susceptibility or responsiveness of a subject suffering from inflammation-associated cancer to the treatment with an EGFR inhibitor/antagonist.

It was found in the context of the present invention that EGFR is expressed in liver macrophages in both human HCC and a mouse HCC model. Genetically modified mice lacking EGFR in different cell types of the liver were employed in order to dissect the role of different cellular players and signaling pathways in HCC development. As also demonstrated in Example 1, mice lacking EGFR in macrophages were found to show impaired hepatocarcinogenesis, whereas mice lacking EGFR in hepatocytes unexpectedly develop more HCC due to increased hepatocyte damage and compensatory proliferation. The presence of EGFR-positive liver macrophages in HCC patients has further been found to be associated with poor survival. Without being bound by theory, it is considered that mechanistically, following IL-1 stimulation, EGFR is required in liver macrophages to transcriptionally induce IL-6, a tumor-inducing cytokine, triggering hepatocyte proliferation and HCC. These findings demonstrate a new tumor-promoting mechanism for EGFR in non-tumor cells, on the basis of which the present invention provides an improved therapy of inflammation-associated cancer using EGFR inhibitors/antagonists.

In particular, the present invention is based on the unexpected finding that the expression of EGFR specifically in myeloid cells that are localized in tissues affected by inflammation-associated cancer, particularly in CD68-positive macrophages (such as Kupffer cells in the case of HCC), is indicative of the corresponding subject/patient being susceptible/responsive to the treatment with an EGFR inhibitor/antagonist. Positive clinical results are to be expected in these patients who have CD68-positive macrophages in the inflammation-associated cancer tissue. This is in clear contrast to previous treatment regimens proposed in the prior art. The determination of the expression of EGFR in myeloid cells thus allows to identify those subjects that can benefit from the treatment with an EGFR inhibitor/antagonist. The present invention hence provides an improved personalized therapy of inflammation-associated cancer, such as HCC or colorectal cancer, based on the purposive identification of those patients that are susceptible to the treatment with an EGFR inhibitor/antagonist.

Accordingly, in a first aspect the present invention provides an in vitro method of assessing the susceptibility or responsiveness of a subject to the treatment with an EGFR inhibitor/antagonist, wherein the subject has been diagnosed as suffering from inflammation-associated cancer or is suspected of suffering from inflammation-associated cancer, the method comprising a step of determining the level of expression of EGFR in myeloid cells in a sample obtained from the subject, wherein the expression of EGFR in the myeloid cells in the sample from the subject is indicative of the subject being susceptible or responsive to the treatment with an EGFR inhibitor/antagonist.

The invention also relates to the method according to the above-described first aspect, wherein a higher level of expression of EGFR in the myeloid cells in the sample from the subject is indicative of a greater susceptibility or responsiveness of the subject to the treatment with an EGFR inhibitor/antagonist.

In a second aspect, the present invention relates to an in vitro method of identifying a subject that is susceptible or responsive to the treatment with an EGFR inhibitor/antagonist, wherein the subject has been diagnosed as suffering from inflammation-associated cancer or is suspected of suffering from inflammation-associated cancer, the method comprising a step of determining the level of expression of EGFR in myeloid cells in a sample obtained from the subject, wherein an increased level of expression of EGFR in the myeloid cells in the sample from the subject as compared to a control expression level of EGFR in corresponding myeloid cells in a healthy subject is indicative of the subject being susceptible or responsive to the treatment with an EGFR inhibitor/antagonist.

In a third aspect, the present invention provides an in vitro method of prognosing the survival time, the progression-free survival time or the disease course of a subject that has been diagnosed as suffering from inflammation-associated cancer or is suspected of suffering from inflammation-associated cancer, the method comprising a step of determining the level of expression of EGFR in myeloid cells in a sample obtained from the subject, wherein a higher level of expression of EGFR in the myeloid cells in the sample from the subject is indicative of a shorter survival time, a shorter progression-free survival time, and a worse disease course, respectively.

In accordance with this third aspect, the invention relates to each one of: (i) an in vitro method of prognosing the survival time of a subject that has been diagnosed as suffering from inflammation-associated cancer or is suspected of suffering from inflammation-associated cancer, the method comprising a step of determining the level of expression of EGFR in myeloid cells in a sample obtained from the subject, wherein a higher level of expression of EGFR in the myeloid cells in the sample from the subject is indicative of a shorter survival time; (ii) an in vitro method of prognosing the progression-free survival time of a subject that has been diagnosed as suffering from inflammation-associated cancer or is suspected of suffering from inflammation-associated cancer, the method comprising a step of determining the level of expression of EGFR in myeloid cells in a sample obtained from the subject, wherein a higher level of expression of EGFR in the myeloid cells in the sample from the subject is indicative of a shorter progression-free survival time; and (iii) an in vitro method of prognosing the disease course of a subject that has been diagnosed as suffering from inflammation-associated cancer or is suspected of suffering from inflammation-associated cancer, the method comprising a step of determining the level of expression of EGFR in myeloid cells in a sample obtained from the subject, wherein a higher level of expression of EGFR in the myeloid cells in the sample from the subject is indicative of a worse disease course.

The term "progression-free survival time" refers to the length of time starting from the determination of the level of expression of EGFR, during which time the subject lives with the inflammation-associated cancer but it does not progress. The progression of the inflammation-associated cancer is preferably determined in accordance with the Response Evaluation Criteria in Solid Tumors (RECIST) version 1.1, as described and defined in Eisenhauer, E. A. et al., 2009. In particular, it is preferred that the inflammation-associated cancer is considered to progress if there is at least a 20% relative increase in the sum of diameters of target lesions (all lesions up to a maximum of five lesions in total and a maximum of two lesions per organ are identified as target lesions and are recorded and measured at baseline), taking as reference the smallest sum previously determined, and if, in addition to the aforementioned relative increase of 20%, the sum of diameters of target lesions demonstrates an absolute increase of at least 5 mm and/or one or more new lesions appear; if these conditions are not fulfilled, the inflammation-associated cancer does not progress.

In a fourth aspect, the invention provides an EGFR inhibitor/antagonist for use in the treatment or amelioration of inflammation-associated cancer in a subject, wherein the subject has been identified in a method according to the first or the second aspect of the invention (preferably according to the first aspect) as being susceptible or responsive to the treatment with an EGFR inhibitor/antagonist.

The invention likewise relates to the use of an EGFR inhibitor/antagonist in the preparation of a medicament for the treatment or amelioration of inflammation-associated cancer in a subject, wherein the subject has been identified in a method according to the first or the second aspect of the invention as being susceptible or responsive to the treatment with an EGFR inhibitor/antagonist.

In accordance with this fourth aspect, the present invention further provides a method of treating or ameliorating inflammation-associated cancer in a subject, the method comprising administering an EGFR inhibitor/antagonist to the subject, wherein the subject has been identified in a method according to the first or the second aspect of the invention as being susceptible or responsive to the treatment with an EGFR inhibitor/antagonist.

In a fifth aspect, the invention relates to an EGFR inhibitor/antagonist for use in the treatment or amelioration of inflammation-associated cancer in a subject, wherein the subject has been identified as being susceptible or responsive to the treatment with an EGFR inhibitor/antagonist by determining the level of expression of EGFR in myeloid cells in a sample obtained from the subject, wherein the expression of EGFR in the myeloid cells in the sample from the subject is indicative of the subject being susceptible or responsive to the treatment with an EGFR inhibitor/antagonist.

In accordance with this fifth aspect, the invention also refers to the use of an EGFR inhibitor/antagonist in the preparation of a medicament for the treatment or amelioration of inflammation-associated cancer in a subject, wherein the subject has been identified as being susceptible or responsive to the treatment with an EGFR inhibitor/antagonist by determining the level of expression of EGFR in myeloid cells in a sample obtained from the subject, wherein the expression of EGFR in the myeloid cells in the sample from the subject is indicative of the subject being susceptible or responsive to the treatment with an EGFR inhibitor/antagonist.

Moreover, the invention provides a method of treating or ameliorating inflammation-associated cancer in a subject that has been diagnosed as suffering from inflammation-associated cancer or is suspected of suffering from inflammation-associated cancer, the method comprising:
    determining the level of expression of EGFR in myeloid cells in a sample obtained from the subject;
    determining whether or not the subject is susceptible or responsive to the treatment with an EGFR inhibitor/antagonist, wherein the expression of EGFR in the myeloid cells in the sample from the subject is indicative of the subject being susceptible or responsive to the treatment with an EGFR inhibitor/antagonist; and
    administering an EGFR inhibitor/antagonist to the subject if the subject has been identified as being susceptible or responsive to the treatment with an EGFR inhibitor/antagonist.

In a sixth aspect, the present invention provides an in vitro diagnostic method of assessing the proneness of a subject to develop inflammation-associated cancer (preferably colorectal cancer), the method comprising a step of determining the level of expression of EGFR in myeloid cells in a sample obtained from the subject, wherein the expression of EGFR in the myeloid cells in the sample from the subject is indicative of the subject being prone to develop inflammation-associated cancer.

The invention also relates to the method according to the above-described sixth aspect, wherein a higher level of expression of EGFR in the myeloid cells in the sample from the subject is indicative of a greater proneness of the subject to develop inflammation-associated cancer.

In a seventh aspect, the invention provides an EGFR inhibitor/antagonist for use in the prevention of inflammation-associated cancer in a subject, wherein the subject has been identified in a method according to the sixth aspect of the invention as being prone to develop inflammation-associated cancer.

The invention likewise relates to the use of an EGFR inhibitor/antagonist in the preparation of a medicament for the prevention of inflammation-associated cancer in a subject, wherein the subject has been identified in a method according to the sixth aspect of the invention as being prone to develop inflammation-associated cancer.

In accordance with this seventh aspect, the present invention further provides a method of preventing inflammation-associated cancer in a subject, the method comprising administering an EGFR inhibitor/antagonist to the subject, wherein the subject has been identified in a method according to the sixth aspect of the invention as being prone to develop inflammation-associated cancer.

The following description of general and preferred features and embodiments relates to each one of the methods, uses and EGFR inhibitors/antagonists provided in the present specification, including in particular those according to the above-described first, second, third, fourth, fifth, sixth and seventh aspects of the invention, unless explicitly indicated otherwise.

The inflammation-associated cancer (e.g., the inflammation-associated cancer that the subject has been diagnosed as suffering from or is suspected of suffering from) may be hepatocellular carcinoma (HCC), colorectal cancer (e.g., colitis-associated cancer), lung cancer (e.g., non-small cell lung cancer), breast cancer, or any other type of inflammation-associated cancer, including in particular solid tumors with macrophage infiltration. Cancers associated with inflammation, particularly chronic inflammation, are known in the art and are described, e.g., in Shacter, E. et al., 2002. It is preferred that the inflammation-associated cancer is HCC or colorectal cancer (such as colitis-associated cancer). More preferably, the inflammation-associated cancer is HCC. It is furthermore preferred that the HCC is very early-stage HCC, early-stage HCC or intermediate-stage HCC, more preferably very early-stage HCC or early-stage HCC, wherein the HCC stage is preferably determined using the Barcelona-Clinic Liver Cancer (BCLC) staging system which is described in Llovet, J. M. et al., 1999 and in Pons, F. et al., 2005.

The sample to be used for determining the expression of EGFR in accordance with the present invention is preferably a cancer tissue biopsy sample. If the inflammation-associated cancer is HCC, it is furthermore preferred that the sample is a liver tissue sample (particularly a liver tissue biopsy sample). Liver tissue samples can be obtained using, e.g., ultrasound guided fine needle biopsy. Preferably, fine needle biopsy aspiration is performed after local anesthesia by using a needle guide attached to the side of the ultrasound scanner, e.g., as described in Caturelli, E. et al., 2004. Further methods of performing liver biopsies are known in the art and are described, e.g., in: Bret, P. M. et al., 1986; Edoute, Y. et al., 1991; Edoute, Y. et al., 1992; Guo, Z. et al., 2002; Ho, C. S. et al., 1981; Michielsen, P. P. et al., 1998; Pilotti, S. et al., 1988; Samaratunga, H. et al., 1992. If the inflammation-associated cancer is colorectal cancer, such as colitis-associated cancer, it is particularly preferred that the sample is a colorectal tissue sample (particularly a colorectal tissue biopsy sample) or a colorectal polyp. Colorectal polyps can conveniently be obtained from the subject to be examined using, e.g., colonoscopy. It is furthermore envisaged that, depending on the specific type of inflammation-associated cancer, the sample may also be a body fluid, such as a blood sample.

While one or more samples obtained from the subject can be used in accordance with the invention, including any of the above-mentioned specific samples, it is preferred to use two or more, particularly three or more, more preferably five or more, and even more preferably ten or more samples from the same subject. The use of multiple samples from the subject allows a more accurate assessment of the susceptibility or responsiveness of the subject to the treatment with an EGFR inhibitor/antagonist or of the survival time, the progression-free survival time or the disease course of the subject.

The myeloid cells, in which the level of expression of EGFR is to be determined, are preferably CD68-positive myeloid cells (i.e., myeloid cells expressing CD68 as defined below), more preferably CD68-positive macrophage cells, and in particular CD68-positive tissue-resident macrophage cells. If the inflammation-associated cancer is HCC, it is most preferred that the myeloid cells are Kupffer cells, particularly CD68-positive Kupffer cells. Kupffer cells (also known as Browicz-Kupffer cells) are specialized macrophages that line the walls of liver sinusoids. They are considered as resident macrophages of the liver and form part of the reticuloendothelial system. Kupffer cells are further described and characterized in: Naito, M. et al., 1997; Naito, M. et al., 2004; and Ikarashi, M. et al., 2013. If the inflammation-associated cancer is colorectal cancer (e.g., colitis-associated cancer), it is particularly preferred that the myeloid cells are CD68-positive myeloid cells of the intestinal lamina propria or CD68-positive macrophage cells from a colorectal polyp. If the inflammation-associated cancer is lung cancer, it is preferred that the myeloid cells are CD68-positive macrophage cells.

As used herein, the term "CD68" refers to the glycoprotein Cluster of Differentiation 68 (also known as macrosialin) of Homo sapiens, including all possible isoforms thereof, and particularly refers to a glycoprotein expressed from the gene having the Entrez Gene ID 968 or a glycoprotein expressed from the mRNA having the NCBI reference sequence NM_001251.2 or NM_001040059.1 or a glycoprotein having the NCBI reference sequence NP_001242.2 or NP_001035148.1 or a glycoprotein having the UniProtKB accession number P34810 (including any of its isoforms, such as P34810-1, P34810-2 or P34810-3). CD68 is further described and characterized in Holness, C. L. et al., 1993. The term "CD68" also refers to homologs and/or orthologs of the above-described human glycoprotein that are found in other (non-human) species, particularly other mammalian species, such as Pan troglodytes (Entrez Gene ID: 100615283; NCBI reference sequences: XM_003315355.1; XM_003315356.1; XP_003315403.1; XP_003315404.1) or Rattus norvegicus (Entrez Gene ID: 287435; NCBI reference sequences: NM_001031638.1; NP_001026808.1). It is to be understood that, if the subject to be examined in accordance with the present invention is a human, then the term "CD68" preferably refers to the corresponding human glycoprotein.

In accordance with the present invention, the level of expression of EGFR is determined in myeloid cells in a sample obtained from the subject to be examined. The level of expression can be determined, for example, by determining the level of translation or the level of transcription of EGFR. Thus, the presence and/or the amount of EGFR protein in myeloid cells in the sample can be determined or the presence and/or the amount of EGFR mRNA in myeloid cells in the sample can be established in order to determine the level of expression of EGFR. This can be accomplished using methods known in the art, as described, e.g., in Green, M. R. et al., 2012. Preferably, the level of expression of EGFR is determined by determining the level of translation of EGFR.

The level of translation of EGFR can, e.g., be determined using antibody-based assays, such as an immunohistochemical method, an enzyme-linked immunosorbent assay (ELISA) or a radioimmunoassay (RIA), wherein antibodies directed specifically against the EGFR protein to be quantified are employed, or mass spectrometry, a gel-based or blot-based assay, or flow cytometry (e.g., FACS). If the level of translation is to be determined, it may be advantageous to include one or more protease inhibitors in the sample from the subject.

The level of transcription of EGFR can, e.g., be determined using a quantitative (real-time) reverse transcriptase polymerase chain reaction ("qRT-PCR") or using a microarray (see, e.g., Ding, C. et al., 2004). It is also possible to use single-cell gene expression analysis techniques, such as single-cell qRT-PCR or single-cell microarray analysis, in order to determine the level of transcription of EGFR in single myeloid cells from the sample. If the level of transcription is to be determined, it may further be advantageous to include one or more RNase inhibitors in the sample from the subject.

In accordance with the present invention, it is preferred that the level of expression of EGFR is determined by determining the level of translation of EGFR. Preferably, the level of translation of EGFR is determined using an antibody-based assay, mass spectrometry, a gel-based or blot-based assay, or flow cytometry, more preferably using an immunohistochemical method, an enzyme-linked immunosorbent assay, or a radioimmunoassay, even more preferably using an immunohistochemical method. It is particularly preferred to use immunohistochemical co-staining for EGFR and for CD68 to determine the level of translation of EGFR in CD68-positive myeloid cells. Methods for immunohistochemical staining and immunohistochemical co-staining are well-known in the art and are described, e.g., in: Renshaw, S., 2007 (particularly chapter 4 "Immunochemical staining techniques"); Key, M., 2006 (particularly chapter 9); and Chen, X. et al., 2010. Co-staining for EGFR and for CD68 can also be carried out as described in Example 1.

As used herein, the term "EGFR" refers to the epidermal growth factor receptor gene in Homo sapiens (Entrez Gene ID: 1956; or NCBI reference sequence: NG_007726.3), the corresponding mRNA (including all possible transcripts/splice variants, such as NCBI reference sequence NM_005228.3, NM_201282.1, NM_201283.1, or NM_201284.1), and/or the corresponding protein (including all possible isoforms, such as NP_005219.2, NP_958439.1, NP_958440.1, or NP_958441.1, and all possible mutant forms, such as any of the aforementioned isoforms having one or more of the following mutations: T790M, L861Q, G719A, G873E, L858R, V802I, G719A, G779C and/or the mutation EGFRvIII (which is described, e.g., in Wikstrand, C. J. et al., 1998 and in Gan, H. K. et al., 2013)). This term also refers to homologs and/or orthologs of the human gene that are found in other (non-human) species, particularly other mammalian species, as well as their corresponding mRNAs and their corresponding proteins (also including any mutant forms thereof). Examples of such homologs or orthologs found in other mammalian species include the epidermal growth factor receptor gene in Mus musculus (Entrez Gene ID: 13649) and in Rattus norvegicus (Entrez Gene ID: 24329) as well as the corresponding mRNAs and proteins. It is to be understood that, if the subject to be examined in accordance with the present invention is a human, then the term "EGFR" preferably refers to the human gene, the corresponding human mRNA and/or the corresponding human protein. The human EGFR protein preferably refers to a protein comprising or having the amino acid sequence NP_005219.2 or a protein comprising or having the amino acid sequence shown in SEQ ID NO: 1, and more preferably refers to a protein having the amino acid sequence shown in SEQ ID NO: 1.

The subject to be examined or treated in accordance with the present invention may be an animal and is preferably a mammal, most preferably a human. The mammal may be, e.g., a rodent (e.g., a guinea pig, a hamster, a rat or a mouse), a murine (e.g., a mouse), a canine (e.g., a dog), a feline (e.g., a cat), a porcine (e.g., a pig), an equine (e.g., a horse), a primate, a simian (e.g., a monkey or an ape), a monkey (e.g., a marmoset or a baboon), an ape (e.g., a gorilla, a chimpanzee, an orang-utan or a gibbon), or a human. Most preferably, the subject to be examined or to be treated in accordance with the invention is a human.

In the first, second, third, fourth and fifth aspect of the invention, it is preferred that the subject to be examined or treated is a subject (preferably a human) that has been diagnosed as suffering from inflammation-associated cancer. In the sixth and seventh aspect of the invention, it is preferred that the subject to be examined or treated is a subject (preferably a human) that does not (yet) suffer from inflammation-associated cancer and/or that has been diagnosed as not suffering from inflammation-associated cancer.

A subject suffering from an infection with hepatitis B virus (HBV), hepatitis C virus (HCV) and/or human immunodeficiency virus (HIV) is particularly prone to develop inflammation-associated cancer such as HCC. It is therefore envisaged that the subject to be examined or treated in accordance with the invention is preferably a subject (e.g., a human) diagnosed as suffering from or suspected to suffer from an infection or coinfection with HBV, HCV and/or HIV.

Furthermore, in the first, second, fourth, fifth, and seventh aspect of the invention, it is preferred that the subject to be examined or treated is a human subject that has no activating RAS gene mutation (e.g., no activating KRAS, NRAS and/or HRAS gene mutation; particularly no activating KRAS gene mutation) in the cells in the sample (which is preferably a cancer tissue biopsy sample), particularly in any inflammation-associated cancer cells in the sample. Activating RAS gene mutations are known in the art and may occur, in particular, as missense point mutations at one or more of the codons 12, 13, 61 and 63 (particularly at codon 12 and/or 13) of the KRAS gene, the NRAS gene and/or the HRAS gene. The numbers 12, 13, 61 and 63 refer to those codons of the respective gene that encode the $12^{th}$ amino acid, the $13^{th}$ amino acid, the $61^{st}$ amino acid, and the $63^{rd}$ amino acid of the corresponding RAS protein. Exemplary activating KRAS gene mutations include each one of the mutations G12A (i.e., a replacement of the codon that encodes the $12^{th}$ amino acid of the KRAS protein, which amino acid is glycine (G) in the wild-type form of KRAS, by a codon that encodes alanine), G12D, G12R, G12V, G12C, G12S, G13D, and Q61H.

As used herein, the term "KRAS" refers to the human KRAS gene (full gene name: Kirsten rat sarcoma viral oncogene homolog; Entrez Gene ID: 3845), the corresponding mRNA (including all possible transcripts/splice variants, such as the mRNA having the NCBI reference sequence NM_004985.4 or NM_033360.3; preferably the mRNA having the NCBI reference sequence NM_004985.4), and the corresponding protein (including all possible isoforms, such as the protein having the NCBI reference sequence NP_004976.2 or NP_203524.1; preferably the protein having the NCBI reference sequence NP_004976.2). The term "NRAS" refers to the human NRAS gene (full gene name: neuroblastoma RAS viral (v-ras) oncogene homolog; Entrez Gene ID: 4893), the corresponding mRNA (including all possible transcripts/splice variants, such as the mRNA having the NCBI reference sequence NM_002524.4), and the corresponding protein (including all possible isoforms, such as the protein having the NCBI reference sequence NP_002515.1). The term "HRAS" refers to the human HRAS gene (full gene name: Harvey rat sarcoma viral oncogene homolog; Entrez Gene ID: 3265), the corresponding mRNA (including all possible transcripts/splice variants, such as the mRNA having the NCBI reference sequence NM_001130442.1, NM_005343.2, or NM_176795.3), and the corresponding protein (including all possible isoforms, such as the protein having the NCBI reference sequence NP_001123914.1, NP_005334.1, or NP_789765.1).

In particular, it is preferred that the subject to be examined or treated in accordance with any of the first, second, fourth, fifth, and seventh aspects of the invention is a human subject whose KRAS mutation status is "wild type" at codons 12 and 13 of the KRAS gene (i.e., codons 12 and 13 each encode glycine, as in the wild-type form of KRAS). Even more preferably, the subject to be examined or treated is a human subject whose KRAS mutation status is wild type at codons 12, 13, 61 and 63 of the KRAS gene (i.e., codons 12 and 13 each encode glycine, codon 61 encodes glutamine, and codon 63 encodes glutamate, as in wild-type KRAS). The KRAS mutation status of the subject can be determined, e.g., using DNA that has been isolated from the sample obtained from the subject (preferably DNA that has been isolated from inflammation-associated cancer cells from said sample). The KRAS mutation status and, accordingly, the presence or absence of activating mutations at the aforementioned codons of the KRAS gene can be tested using methodologies known in the art, such as PCR-based methods (e.g., amplification refractory mutation system (ARMS) PCR), nucleic acid sequencing methods (e.g., dideoxy sequencing or pyrosequencing), mutation specific hybridization, or melting point analysis. Test kits that can be used for determining the KRAS mutation status are also commercially available (e.g., the QIAGEN therascreen KRAS RGQ PCR Kit or the QIAGEN therascreen KRAS Pyro Kit, both available from QIAGEN GmbH, Hilden, Germany). Further information on activating RAS mutations, particularly activating mutations in the KRAS gene, as well as methodologies for the detection of such mutations can be found in the literature, including, e.g., in: Schubert, S. et al., 2007; Keohavong, P. et al., 1996; Gerry, N. P. et al., 1999; Faulkner, N. E. et al., 2010; Amado, R. G. et al., 2008; Bokemeyer, C. et al., 2011; Peeters, M. et al., 2010; or Stintzing, S. et al., 2009.

The EGFR inhibitor/antagonist is not particularly limited and may be any agent that inhibits or antagonizes the epidermal growth factor receptor. While the terms "EGFR inhibitor" and "EGFR antagonist" are often used synonymously in the art, the term "EGFR antagonist" in a narrow sense relates to a ligand of the epidermal growth factor receptor that blocks or dampens the response mediated by an agonist (i.e., an EGFR-activating ligand, such as epidermal growth factor (EGF) or transforming growth factor alpha (TGF-α)) but does not itself provoke a response upon binding to the receptor. Such an EGFR antagonist may be, e.g., a small molecule or an antibody, particularly a monoclonal antibody. The term "EGFR inhibitor" in a narrow sense refers to an agent (typically a small molecule) that binds to the epidermal growth factor receptor and inhibits or decreases its intrinsic tyrosine kinase activity. The term "EGFR inhibitor/antagonist" as used herein also relates specifically to an EGFR inhibitor and/or specifically to an EGFR antagonist in the above-defined narrow sense.

Exemplary EGFR inhibitors/antagonists include, inter alia, small-molecule EGFR inhibitors/antagonists, such as gefitinib, erlotinib, lapatinib, afatinib (also referred to as BIBW2992), neratinib, ABT-414, dacomitinib (also referred to as PF-00299804), AV-412, PD 153035, vandetanib, PKI-166, pelitinib (also referred to as EKB-569), canertinib (also referred to as CI-1033), icotinib, poziotinib (also referred to as NOV120101), BMS-690514, CUDC-101, AP26113 or XL647 as well as inhibitory/antagonistic antibodies, particularly inhibitory/antagonistic monoclonal antibodies, such as cetuximab, panitumumab, zalutumumab, nimotuzumab or matuzumab. The EGFR inhibitor/antagonist may also be a pharmaceutically acceptable salt of an EGFR inhibitor/antagonist, including any of the above-described specific agents. Preferably, the EGFR inhibitor/antagonist is selected from gefitinib, erlotinib, lapatinib, afatinib, neratinib, ABT-414, dacomitinib, AV-412, PD 153035, vandetanib, PKI-166, pelitinib, canertinib, icotinib, poziotinib, BMS-690514, CUDC-101, AP26113, XL647, cetuximab, panitumumab, zalutumumab, nimotuzumab, matuzumab, or a pharmaceutically acceptable salt of any one of the aforementioned agents (e.g., lapatinib ditosylate, PD 153035 hydrochloride, or icotinib hydrochloride). If the inflammation-associated cancer is colorectal cancer (e.g., colitis-associated cancer), it is particularly preferred that the EGFR inhibitor/antagonist is selected from cetuximab, panitumumab and matuzumab.

The scope of the invention embraces all pharmaceutically acceptable salt forms of an EGFR inhibitor/antagonist, including any of the above-described specific EGFR inhibitors/antagonists, which may be formed, e.g., by protonation of an atom carrying an electron lone pair which is susceptible to protonation, such as an amino group, with an inorganic or organic acid, or as a salt of a carboxylic acid group with a physiologically acceptable cation as they are well-known in the art. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, glycolate, nicotinate, benzoate, salicylate, ascorbate, or pamoate (embonate) salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; and acidic amino acid salts such as aspartate or glutamate salts.

Where an EGFR inhibitor/antagonist is to be used for the treatment or amelioration of inflammation-associated cancer, particularly in accordance with the fourth or the fifth aspect of the invention, or where an EGFR inhibitor/antagonist is to be used for the prevention of inflammation-associated cancer, in particular in accordance with the seventh aspect of the invention, the EGFR inhibitor/antagonist may be administered per se or may be formulated as a medicament or pharmaceutical composition. Such medicaments or pharmaceutical compositions may comprise one or more pharmaceutically acceptable excipients, such as carriers, diluents, fillers, disintegrants, lubricating agents, binders, colorants, pigments, stabilizers, preservatives, antioxidants, and/or solubility enhancers.

The pharmaceutical compositions can be formulated by techniques known in the art, such as the techniques published in Remington's Pharmaceutical Sciences, $20^{th}$ Edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The EGFR inhibitor/antagonist or the above-described pharmaceutical compositions comprising one or more EGFR inhibitors/antagonists may be administered to the subject by any convenient route of administration, whether systemically/peripherally or at the site of desired action, including but not limited to one or more of: oral (e.g., as a tablet, capsule, or as an ingestible solution), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, and vaginal.

If the EGFR inhibitors/antagonists or the pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the EGFR inhibitors/antagonists or pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known in the art.

The EGFR inhibitors/antagonists or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, the EGFR inhibitors/antagonists or pharmaceutical compositions can be administered in the form of a suppository or pessary, or may be applied topically in the form of a gel, hydrogel, lotion, solution, cream, ointment or dusting powder. They may also be dermally or transdermally administered, for example, by the use of a skin patch.

The EGFR inhibitors/antagonists or pharmaceutical compositions may also be administered by sustained release systems. Suitable examples of sustained-release compositions include semi-permeable polymer matrices in the form of shaped articles, e.g., films, or microcapsules. Sustained-release matrices include, e.g., polylactides (U.S. Pat. No. 3,773,919), copolymers of L-glutamic acid and gamma-ethyl-L-glutamate (Sidman, U. et al., 1983), poly(2-hydroxyethyl methacrylate) (Langer, R. et al., 1981; Langer, R. et al., 1982), ethylene vinyl acetate (Langer, R. et al., 1981; Langer, R. et al., 1982) or poly-D-(−)-3-hydroxybutyric acid (EP133988). Sustained-release pharmaceutical compositions also include liposomally entrapped compounds. Liposomes containing an EGFR inhibitor/antagonist can be prepared by methods known in the art, such as, e.g., the methods described in any one of: DE3218121; Epstein et al., 1985; Hwang et al., 1980; EP0052322; EP0036676; EP088046; EP0143949; EP0142641; JP 83-118008; U.S. Pat. Nos. 4,485,045 and 4,544,545; and EP0102324.

The EGFR inhibitors/antagonists or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the EGFR inhibitors/antagonists for pulmonary administration, particularly inhalation. Such dry powders may be prepared by spray drying under conditions which result in a substantially amorphous glassy or a substantially crystalline bioactive powder. Accordingly, dry powders of the EGFR inhibitors/antagonists can be made according to the emulsification/spray drying process disclosed in WO 99/16419 or WO 01/85136. Spray drying of solution formulations of the compounds of the present invention is carried out, for example, as described generally in the "Spray Drying Handbook", 5th ed., K. Masters, John Wiley & Sons, Inc., NY, N.Y. (1991), and in WO 97/41833 or WO 03/053411.

For topical application to the skin, the EGFR inhibitors/antagonists or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

In one embodiment, the EGFR inhibitors/antagonists or pharmaceutical compositions can be used in combination with other therapeutic agents. When an EGFR inhibitor/antagonist is used in combination with a second therapeutic agent active against the same disease, the dose of each compound may differ from that when one of the compounds is used alone. The combination of an EGFR inhibitor/antagonist with one or more other drugs may comprise the administration of the drug(s) with the EGFR inhibitor/antagonist. Such an administration may be simultaneous/concomitant or sequential/separate.

Preferably, the second therapeutic agent to be administered in combination with an EGFR inhibitor/antagonist (e.g., in accordance with the fourth, fifth or seventh aspect of the invention) is an anticancer drug. The anticancer drug may be a tumor angiogenesis inhibitor (for example, a protease inhibitor); a cytotoxic drug (for example, an antimetabolite, such as purine and pyrimidine analog antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analogue); or a compound that targets an enzyme or receptor that is overexpressed and/or otherwise involved in a specific metabolic pathway that is misregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and kinase inhibitors therefor (such as fibroblast growth factor inhibitors, insulin-like growth factor receptor inhibitors and platelet-derived growth factor receptor kinase inhibitors)); methionine, aminopeptidase inhibitors, proteasome inhibitors, cyclooxygenase inhibitors (for example, cyclooxygenase-1 or cyclooxygenase-2 inhibitors) and topoisomerase inhibitors (for example, topoisomerase I inhibitors or topoisomerase II inhibitors). A particularly preferred anticancer drug to be administered in combination with the EGFR inhibitor/antagonist is sorafenib.

An alkylating agent which can be used as an anticancer drug in combination with the EGFR inhibitor/antagonist may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, Thio-TEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an anticancer drug in combination with the EGFR inhibitor/antagonist may be, for example, cisplatin, carboplatin, nedaplatin, oxaliplatin, satraplatin, or triplatin tetranitrate.

A cytotoxic drug which can be used as an anticancer drug in combination with the EGFR inhibitor/antagonist may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with the EGFR inhibitor/antagonist may be, for example, a taxane (such as docetaxel, larotaxel, ortataxel, paclitaxel/taxol, or tesetaxel), a *Vinca* alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with the EGFR inhibitor/antagonist may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with the EGFR inhibitor/antagonist may be, for example, axitinib, bosutinib, cediranib, dasatinib, lestaurtinib, nilotinib, semaxanib, sorafenib, sunitinib, or vandetanib.

A topoisomerase-inhibitor which can be used as an anticancer drug in combination with the EGFR inhibitor/antagonist may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

Further anticancer drugs may be used in combination with the EGFR inhibitor/antagonist. Such anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, and/or vorinostat.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the EGFR inhibitor/antagonist. Examples of such biological molecules are anti-HER2 antibodies (e.g. trastuzumab, Herceptin®), anti-CD20 antibodies (e.g. rituximab, Rituxan®, MabThera, Reditux®), anti-CD19/CD3 constructs (see, e.g., EP11071752) and anti-TNF antibodies (see, e.g., Taylor, P. C., 2003). Further antibodies, antibody fragments, antibody constructs and/or modified antibodies to be used in co-therapy approaches with the EGFR inhibitor/antagonist can be found in: Taylor, P. C., 2003; Roxana, A., 2006.

In another embodiment, the EGFR inhibitors/antagonists or pharmaceutical compositions are administered in combination with physical therapy, such as radiotherapy. Radiotherapy may commence before, after, or simultaneously with administration of the EGFR inhibitors/antagonists or pharmaceutical compositions. For example, radiotherapy may commence 1-10 minutes, 1-10 hours or 24-72 hours after administration of the EGFR inhibitors/antagonists or pharmaceutical compositions. The subject is exposed to radiation, preferably gamma radiation, whereby the radiation may be provided in a single dose or in multiple doses which are administered over several hours, days and/or weeks. Gamma radiation may be delivered according to standard radiotherapeutic protocols using standard dosages and regimens.

The term "treatment" as in "treatment of inflammation-associated cancer" is well known in the art and implies that the corresponding disorder or disease is suspected or has been diagnosed in a subject. A subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). "Treatment" of a disorder or disease may also lead to a partial response (e.g., amelioration of symptoms) or complete response (e.g., disappearance of symptoms) of the subject suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject may experience a broad range of responses to a treatment (e.g., the exemplary responses as described herein above).

"Treatment" of a disorder or disease may, inter alia, comprise curative treatment (preferably leading to a complete response and eventually to healing of the disorder or disease) and/or palliative treatment (including symptomatic relief).

Also the term "prevention" of a disorder or disease, as in "prevention of inflammation-associated cancer", is well known in the art. For example, a subject suspected of being prone to suffer from a disorder or disease may benefit from a prevention of the disorder or disease. The subject may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the subject (for example, the subject does not show any clinical or pathological symptoms). Thus, the term "prevention" comprises the use of EGFR inhibitors/antagonists or corresponding pharmaceutical compositions before any clinical and/or pathological symptoms are diagnosed or determined or can be diagnosed or determined by the attending physician.

The method according to the first aspect of the present invention may further comprise a step of determining whether the subject is susceptible or responsive to the treatment with an EGFR inhibitor/antagonist, wherein the expression of EGFR in the myeloid cells in the sample from the subject is indicative of the subject being susceptible or responsive to the treatment with an EGFR inhibitor/antagonist.

The method according to the second aspect of the invention may further comprise a step of determining whether the subject is susceptible or responsive to the treatment with an EGFR inhibitor/antagonist, wherein an increased level of expression of EGFR in the myeloid cells in the sample from the subject as compared to a control expression level of EGFR in corresponding myeloid cells in a healthy subject is indicative of the subject being susceptible or responsive to the treatment with an EGFR inhibitor/antagonist.

The method according to the third aspect of the invention may further comprise a step of making a prognosis of the survival time, the progression-free survival time or the disease course of the subject, wherein a higher level of expression of EGFR in the myeloid cells in the sample from the subject is indicative of a shorter survival time, a shorter progression-free survival time, and a worse disease course, respectively.

In accordance with the first, fourth, fifth, sixth and seventh aspect of the invention, determining the level of expression of EGFR refers not only to a quantitative determination of the expression of EGFR but also to a qualitative determination whether or not EGFR is expressed, regardless of the specific (quantitative) level of expression.

In accordance with the first, fourth and fifth aspect of the invention, any expression of EGFR, even a very low level of expression of EGFR, in the corresponding myeloid cells in the sample from the subject is indicative of the subject being susceptible or responsive to the treatment with an EGFR inhibitor/antagonist. A threshold can, however, be applied in order to improve the accuracy of the assessment whether the subject is susceptible/responsive to the treatment with an EGFR inhibitor/antagonist. Thus, if the expression of EGFR is determined by determining the translation of EGFR using immunohistochemical staining for EGFR, it is preferred that only the staining of at least about 5% (more preferably at least about 10%, even more preferably at least about 20%, and still more preferably at least about 30%) of the total number of myeloid cells in an immunohistochemical preparation obtained from the sample (e.g., the tissue biopsy sample) from the subject is considered to be indicative of the subject being susceptible or responsive to the treatment with an EGFR inhibitor/antagonist. In this regard, it is particularly expedient to use immunohistochemical co-staining for EGFR and CD68 and to determine the percentage of co-stained EGFR-positive CD68-positive cells in relation to the total number of CD68-positive cells (i.e., in relation to the sum of the numbers of EGFR-negative CD68-positive cells and EGFR-positive CD68-positive cells). Accordingly, if the expression of EGFR is determined by determining the translation of EGFR using immunohistochemical co-staining for EGFR and for CD68, it is preferred that only the double staining (for both EGFR and CD68) of at least about 5% (more preferably at least about 10%, even more preferably at least about 20%, and still more preferably at least about 30%) of the total number of CD68-stained cells in an immunohistochemical preparation obtained from the sample (e.g., the tissue biopsy sample) from the subject is indicative of the subject being susceptible or responsive to the treatment with an EGFR inhibitor/antagonist.

In the method according to the second aspect of the invention, the level of expression of EGFR in myeloid cells in a sample from the subject to be examined is compared to a control expression level of EGFR in corresponding myeloid cells in a healthy subject. The control expression level of EGFR can be established as part of the method according to the second aspect, which may thus include a further step of determining the level of expression of EGFR in a sample obtained from a healthy subject (i.e., a subject that does not suffer from inflammation-associated cancer) or in a mixture of samples from several healthy subjects (e.g., about 10, about 20, about 50, about 100, or about 500 healthy subjects). Alternatively, the control expression level of EGFR can also be derived from the medical literature or from experiments conducted before carrying out the method of the second aspect of invention. It will be understood that the conditions under which the control expression level is or was obtained (regardless of whether it is derived from the literature or earlier experiments or whether it is determined in the course of carrying out the method according to the second aspect of the invention), including also the type/origin of the sample (or mixture of samples) from the healthy subject, should be identical or at least similar/comparable to the conditions used for determining the level of expression of EGFR in myeloid cells in the sample obtained from the subject to be examined. As an approximation, the control expression level of EGFR in myeloid cells of a healthy subject can normally be expected to be zero, i.e., EGFR is normally not expressed in myeloid cells of a healthy subject.

In the above-described sixth aspect, the present invention provides an in vitro diagnostic method of assessing the proneness of a subject to develop inflammation-associated cancer, the method comprising a step of determining the level of expression of EGFR in myeloid cells in a sample obtained from the subject, wherein the expression of EGFR in the myeloid cells in the sample from the subject is indicative of the subject being prone to develop inflammation-associated cancer. In this sixth aspect, it is preferred that the sample is a colorectal polyp and that the inflammation-associated cancer is colorectal cancer (e.g., colitis-associated cancer). If a subject has been identified in this method as being prone to develop inflammation-associated cancer (particularly colorectal cancer), the subject can take appropriate measures to reduce the risk for the development of inflammation-associated cancer, which provides a substantial benefit for the subject. For example, the subject thus identified can undergo preventive medical checkups (such as, e.g., colonoscopies) more frequently and/or a tissue biopsy sample can be taken from the subject and can be examined in order to make a more accurate diagnosis. The subject thus identified can also be administered an EGFR inhibitor/antagonist for prophylactic treatment, as also described in the seventh aspect of the invention.

The present invention furthermore relates to the use of an antibody against (i.e., binding to) the EGFR protein in an in vitro method of assessing the susceptibility or responsiveness of a subject to the treatment with an EGFR inhibitor/antagonist, which subject has been diagnosed as suffering from inflammation-associated cancer or is suspected of suffering from inflammation-associated cancer. An example of such an in vitro method of assessing the susceptibility or responsiveness of a subject to the treatment with an EGFR inhibitor/antagonist is the method according to the first aspect of the invention. The antibody binds specifically to the EGFR protein and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an $F(ab')_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow, E. et al., 1998. For example, monoclonal antibodies can be prepared by methods such as the hybridoma technique (see, e.g., Köhler, G. et al., 1975), the trioma technique, the human B-cell hybridoma technique (see, e.g., Kozbor, D. et al., 1983) or the EBV-hybridoma technique (see, e.g., Cole, S. P. C. et al., 1985).

As used herein, the term "about" refers to ±10% of the indicated numerical value, and in particular to ±5% of the indicated numerical value. Whenever the term "about" is used, a specific and preferred reference to the exact numerical value indicated is also included.

It is to be understood that the present invention specifically relates to each and every combination of features and embodiments described herein, including any combination of general and/or preferred features/embodiments. In particular, the invention specifically relates to all combinations of preferred features/embodiments which are described herein.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention particularly relates to the following embodiments:

1. An in vitro method of assessing the susceptibility or responsiveness of a subject to the treatment with an epidermal growth factor receptor (EGFR) inhibitor/antagonist, wherein the subject has been diagnosed as suffering from inflammation-associated cancer or is suspected of suffering from inflammation-associated cancer, the method comprising a step of determining the level of expression of EGFR in myeloid cells in a sample obtained from the subject, wherein the expression of EGFR in the myeloid cells in the sample from the subject is indicative of the subject being susceptible or responsive to the treatment with an EGFR inhibitor/antagonist.
2. The method of embodiment 1, wherein a higher level of expression of EGFR in the myeloid cells in the sample from the subject is indicative of a greater susceptibility or responsiveness of the subject to the treatment with an EGFR inhibitor/antagonist.
3. An in vitro method of prognosing the survival time, the progression-free survival time or the disease course of a subject that has been diagnosed as suffering from inflammation-associated cancer or is suspected of suffering from inflammation-associated cancer,
    the method comprising a step of determining the level of expression of epidermal growth factor receptor (EGFR) in myeloid cells in a sample obtained from the subject, wherein a higher level of expression of EGFR in the myeloid cells in the sample from the subject is indicative of a shorter survival time, a shorter progression-free survival time, and a worse disease course, respectively.
4. The method of any one of embodiments 1 to 3, wherein the sample is a cancer tissue biopsy sample.

5. The method of any one of embodiments 1 to 4, wherein the myeloid cells are CD68-positive.
6. The method of any one of embodiments 1 to 5, wherein the myeloid cells are CD68-positive macrophage cells.
7. The method of any one of embodiments 1 to 6, wherein the inflammation-associated cancer is hepatocellular carcinoma.
8. The method of any one of embodiments 1 to 7, wherein the sample is a liver tissue sample.
9. The method of any one of embodiments 1 to 8, wherein the myeloid cells are Kupffer cells.
10. The method of any one of embodiments 1 to 6, wherein the inflammation-associated cancer is colorectal cancer.
11. The method of embodiment 10, wherein the colorectal cancer is colitis-associated cancer.
12. The method of any one of embodiments 1 to 6, 10 or 11, wherein the sample is a colorectal tissue sample or a colorectal polyp.
13. The method of any one of embodiments 1 to 6 or 10 to 12, wherein the myeloid cells are CD68-positive myeloid cells of the intestinal lamina propria.
14. An in vitro diagnostic method of assessing the proneness of a subject to develop inflammation-associated cancer, the method comprising a step of determining the level of expression of epidermal growth factor receptor (EGFR) in myeloid cells in a sample obtained from the subject, wherein the expression of EGFR in the myeloid cells in the sample from the subject is indicative of the subject being prone to develop inflammation-associated cancer.
15. The method of embodiment 14, wherein a higher level of expression of EGFR in the myeloid cells in the sample from the subject is indicative of a greater proneness of the subject to develop inflammation-associated cancer.
16. The method of embodiment 14 or 15, wherein the myeloid cells are CD68-positive.
17. The method of any one of embodiments 14 to 16, wherein the sample is a colorectal polyp.
18. The method of any one of embodiments 14 to 17, wherein the inflammation-associated cancer is colorectal cancer.
19. The method of embodiment 18, wherein the colorectal cancer is colitis-associated cancer.
20. The method of any one of embodiments 1 to 19, wherein the level of expression of EGFR is determined by determining the level of translation of EGFR.
21. The method of embodiment 20, wherein the level of translation is determined using an antibody-based assay, mass spectrometry, a gel-based or blot-based assay, or flow cytometry.
22. The method of embodiment 20 or 21, wherein the level of translation is determined using an immunohistochemical method, an enzyme-linked immunosorbent assay, or a radioimmunoassay.
23. The method of any one of embodiments 1 to 19, wherein the level of expression of EGFR is determined by determining the level of transcription of EGFR.
24. The method of embodiment 23, wherein the level of transcription is determined using a quantitative reverse transcriptase polymerase chain reaction or a microarray.
25. The method of any one of embodiments 1 to 24, wherein the subject is a human.
26. The method of any one of embodiments 1 to 25, wherein the subject has been diagnosed as suffering from or is suspected to suffer from an infection with hepatitis B virus, hepatitis C virus and/or HIV.
27. An EGFR inhibitor/antagonist for use in the treatment or amelioration of inflammation-associated cancer in a subject, wherein the subject has been identified in the method of embodiment 1 or 2 or any one of their dependent embodiments 4 to 13 or 20 to 26 as being susceptible or responsive to the treatment with an EGFR inhibitor/antagonist.
28. Use of an EGFR inhibitor/antagonist in the preparation of a medicament for the treatment or amelioration of inflammation-associated cancer in a subject, wherein the subject has been identified in the method of embodiment 1 or 2 or any one of their dependent embodiments 4 to 13 or 20 to 26 as being susceptible or responsive to the treatment with an EGFR inhibitor/antagonist.
29. An EGFR inhibitor/antagonist for use in the treatment or amelioration of inflammation-associated cancer in a subject, wherein the subject has been identified as being susceptible or responsive to the treatment with an EGFR inhibitor/antagonist by determining the level of expression of EGFR in myeloid cells in a sample obtained from the subject, wherein the expression of EGFR in the myeloid cells in the sample from the subject is indicative of the subject being susceptible or responsive to the treatment with an EGFR inhibitor/antagonist.
30. Use of an EGFR inhibitor/antagonist in the preparation of a medicament for the treatment or amelioration of inflammation-associated cancer in a subject, wherein the subject has been identified as being susceptible or responsive to the treatment with an EGFR inhibitor/antagonist by determining the level of expression of EGFR in myeloid cells in a sample obtained from the subject, wherein the expression of EGFR in the myeloid cells in the sample from the subject is indicative of the subject being susceptible or responsive to the treatment with an EGFR inhibitor/antagonist.
31. A method of treating or ameliorating inflammation-associated cancer in a subject, the method comprising administering an EGFR inhibitor/antagonist to the subject, wherein the subject has been identified in the method of embodiment 1 or 2 or any one of their dependent embodiments 4 to 13 or 20 to 26 as being susceptible or responsive to the treatment with an EGFR inhibitor/antagonist.
32. A method of treating or ameliorating inflammation-associated cancer in a subject that has been diagnosed as suffering from inflammation-associated cancer or is suspected of suffering from inflammation-associated cancer, the method comprising:
 determining the level of expression of epidermal growth factor receptor (EGFR) in myeloid cells in a sample obtained from the subject;
 determining whether or not the subject is susceptible or responsive to the treatment with an EGFR inhibitor/antagonist, wherein the expression of EGFR in the myeloid cells in the sample from the subject is indicative of the subject being susceptible or responsive to the treatment with an EGFR inhibitor/antagonist; and
 administering an EGFR inhibitor/antagonist to the subject if the subject has been identified as being susceptible or responsive to the treatment with an EGFR inhibitor/antagonist.
33. An EGFR inhibitor/antagonist for use in the prevention of inflammation-associated cancer in a subject, wherein the subject has been identified in the method of embodiment 14 or any one of its dependent embodiments 15 to 26 as being prone to develop inflammation-associated cancer.
34. Use of an EGFR inhibitor/antagonist in the preparation of a medicament for the prevention of inflammation-associated cancer in a subject, wherein the subject has been identified in the method of embodiment 14 or any one of its dependent embodiments 15 to 26 as being prone to develop inflammation-associated cancer.

35. A method of preventing inflammation-associated cancer in a subject, the method comprising administering an EGFR inhibitor/antagonist to the subject, wherein the subject has been identified in the method of embodiment 14 or any one of its dependent embodiments 15 to 26 as being prone to develop inflammation-associated cancer.

36. The method of embodiment 1 or 2 or any one of their dependent embodiments 4 to 13 or 20 to 26 or the EGFR inhibitor/antagonist for use according to embodiment 27, 29 or 33 or the use of embodiment 28, 30 or 34 or the method of embodiment 31, 32 or 35, wherein the EGFR inhibitor/antagonist is selected from gefitinib, erlotinib, lapatinib, afatinib, neratinib, ABT-414, dacomitinib, AV-412, PD 153035, vandetanib, PKI-166, pelitinib, canertinib, icotinib, poziotinib, BMS-690514, CUDC-101, AP26113, XL647, cetuximab, panitumumab, zalutumumab, nimotuzumab, matuzumab, or a pharmaceutically acceptable salt thereof.

The invention is also described by the following illustrative figures. The appended figures show:

FIG. 1: HCC Induction and liver damage in mice and hepatocytes. (A) Tumor development was initiated in male $EGFR^{\Delta hep}$ mice (top pattern; $EGFR^{f/f}$; Alfp-Cre) by a single dose of DEN at 4 weeks of age (black arrow). Starting at 8 weeks of age tumors were promoted by a diet complemented with phenobarbital (PB) until mice were sacrificed. Tumor development was initiated in male $EGFR^{f/f}$; Mx-Cre mice by a single dose of DEN at 4 weeks of age (indicated by black arrow). At 7 weeks of age pI-pC was injected to delete EGFR in the liver (middle pattern; $EGFR^{\Delta liv}$, grey arrow). Starting at 8 weeks of age tumors were promoted by a diet complemented with phenobarbital until mice were sacrificed. EGFR deletion in the liver was induced on day 9, 11, and 13 after birth in male $EGFR^{f/f}$; Mx-Cre mice (bottom pattern; $EGFR^{\Delta liv*}$, grey arrow). Tumor development was induced at the age of 4 weeks by a single dose of DEN (black arrow). Starting at 8 weeks of age tumors were promoted by a diet complemented with PB until mice were sacrificed. White bar: EGFR absent; striped bar EGFR present; spotted bar: promotion by PB. (B) Southern Blot analysis showing efficient deletion of EGFR in $EGFR^{\Delta liv}$ livers (f: floxed EGFR allele, Δ: Cre-deleted EGFR allele). (C) Number of Ki67 (left) and TUNEL (right) positive cells in non-tumor tissue adjacent to tumors of $EGFR^{f/f}$ and $EGFR^{\Delta liv}$ mice. (D) H&E staining of liver sections of $EGFR^{f/f}$ (left), $EGFR^{\Delta hep}$ (middle), and $EGFR^{\Delta liv}$ (right) 0, 36, 48, and 72 hours after DEN intoxication in vivo (n=3-4 for each genotype and time point). Black arrows indicate necrotic areas. (E-F) Alanine transaminase (ALT, E) and aspartate transaminase (AST, F) activity measured in the serum of $EGFR^{f/f}$, $EGFR^{\Delta hep}$, and $EGFR^{\Delta liv}$ mice 0, 24, and 48 hours after DEN intoxication. (G) HMGB1 staining of cultured primary $EGFR^{f/f}$ and $EGFR^{\Delta liv}$ hepatocytes 12 hours after DEN treatment in vitro (bottom), demonstrating increased necrotic response in the absence of EGFR. Nuclei (DAPI), actin (Phalloidin), HMGB1 (Alexa 488). (H) Active caspase-3 staining of cultured primary hepatocytes of $EGFR^{f/f}$ and $EGFR^{\Delta liv}$ mice incubated with TNFα/CHX for 12 hours. Nuclei (DAPI), actin (Phalloidin), active caspase-3 (Alexa 488). (I) Release of IL-1β and IL-1α to the supernatant of cultured primary hepatocytes of $EGFR^{f/f}$, $EGFR^{\Delta hep}$, and $EGFR^{\Delta liv}$ mice after incubation with TNFα quantified by ELISA. n.d.=not detectable. (C, E, F, I) Data represent mean±s.e.m. Student's t-test for independent samples and unequal variances was used to assess statistical significance (*p<0.05, p<0.01, *p<0.001).

Figure 2:
Figure 2:
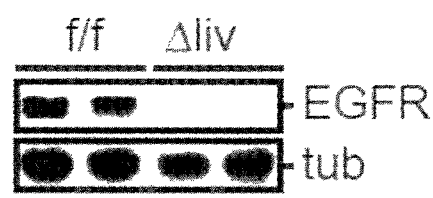
Figure 2:
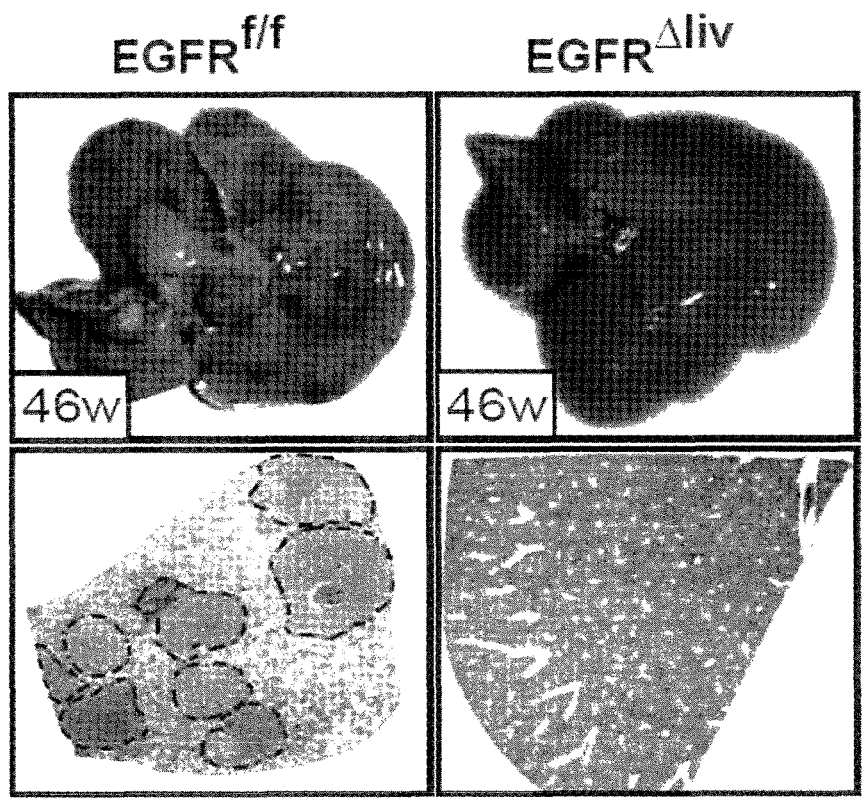
Figure 2:
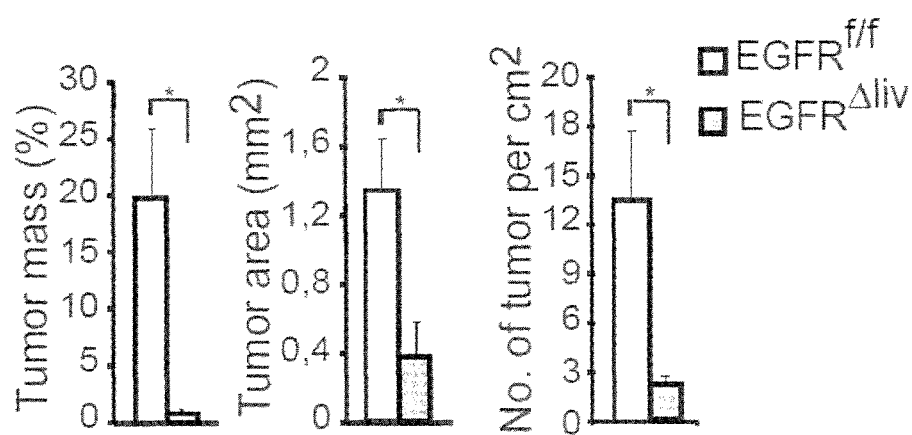
Figure 2:
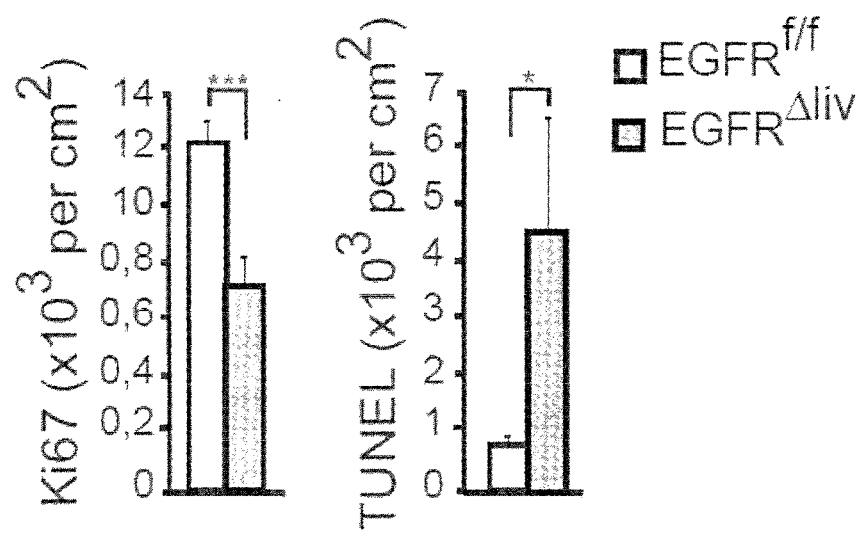
Figure 2:
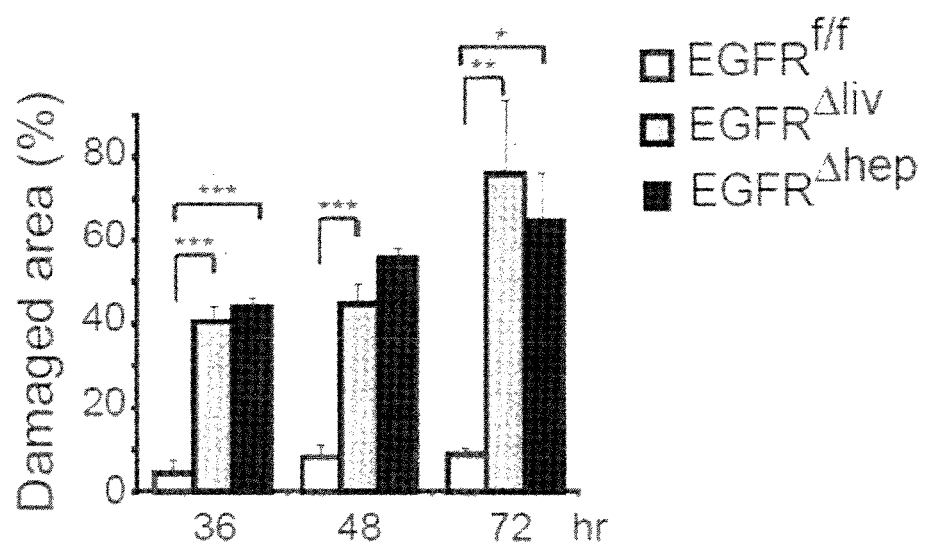
Figure 2:
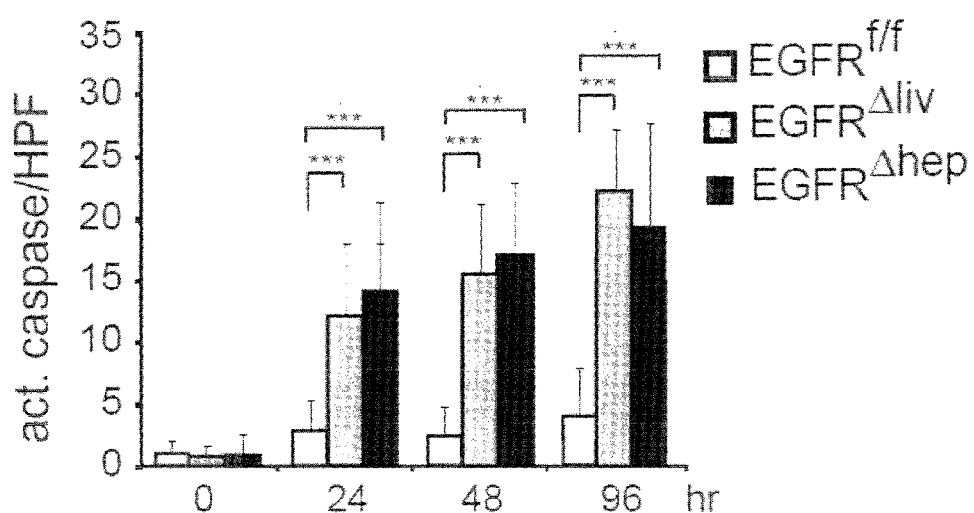
Figure 2:
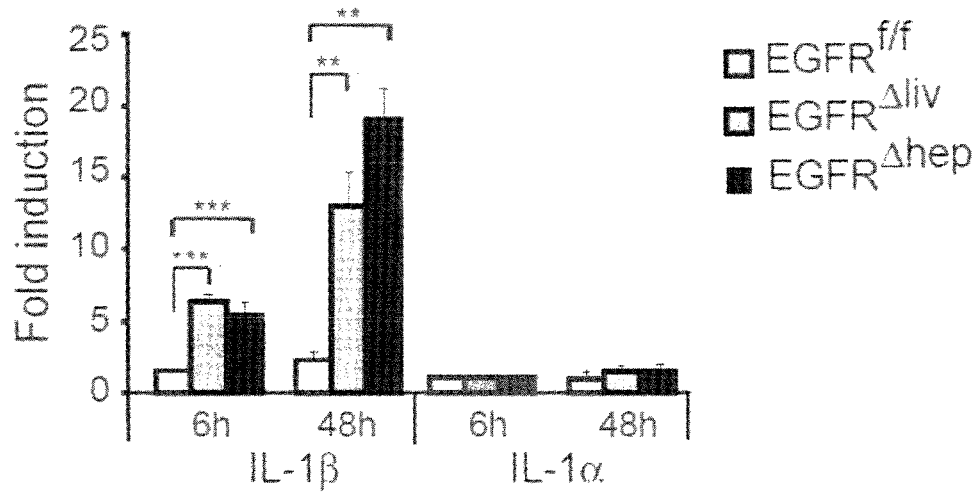
Figure 2:
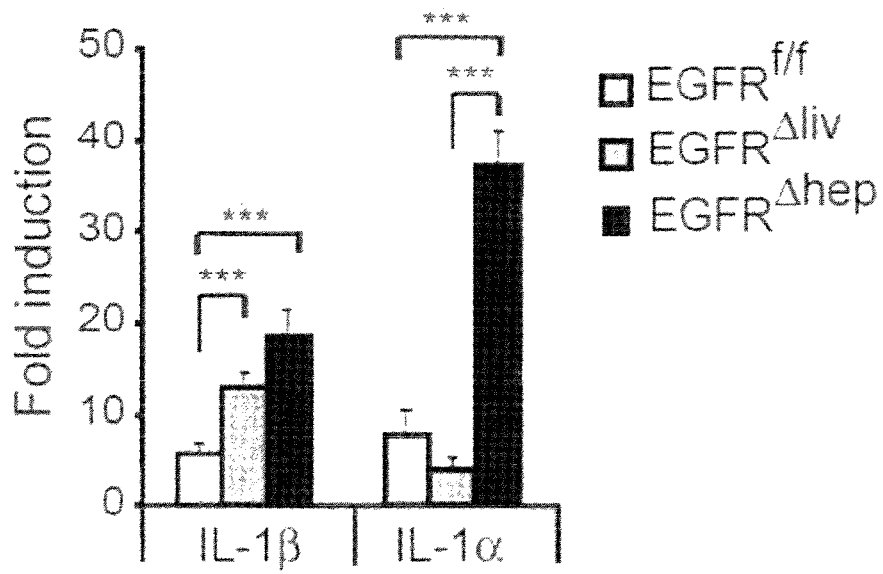
Figure 2:
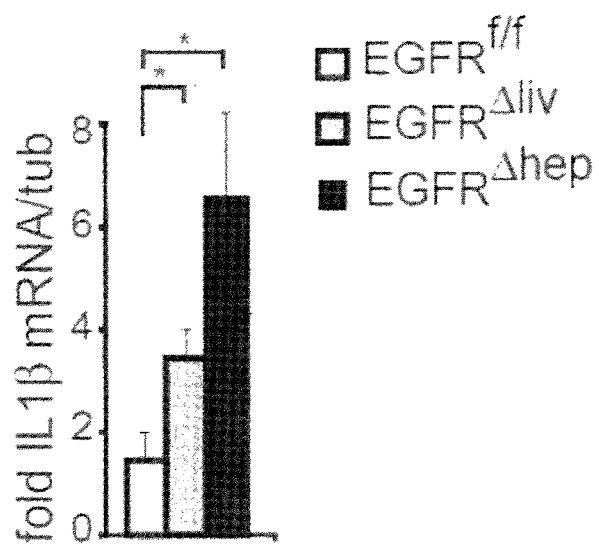

FIG. 2: Reduced HCC formation in mice lacking EGFR in the liver. (A) EGFR staining on liver tumor sections from $EGFR^{f/f}$ (left) and EGFR (right) mice. (B) Western Blot of tumors of $EGFR^{f/f}$ and $EGFR^{\Delta liv}$ livers. (C) Representative livers (top) and H&E staining of liver sections (bottom) of $EGFR^{f/f}$ (left) and $EGFR^{\Delta liv}$ (right) mice 46 weeks after DEN/PB carcinogenesis. Magnification 10x. Dotted lines mark tumor nodules. (D) Tumor mass (left), area (middle), and number (right) in livers of $EGFR^{f/f}$ (n=8) and $EGFR^{\Delta liv}$ (n=10) mice 46 weeks after tumor initiation. (E) Ki67-positive (left) and TUNEL-positive cells (right) in tumors of the indicated genotypes. $EGFR^{f/f}$ (n=8) and $EGFR^{\Delta liv}$ (n=10). Data (D, E) represent mean±s.e.m. (F) Increased damaged liver areas in the absence of EGFR expression quantified on liver sections of $EGFR^{f/f}$, $EGFR^{\Delta liv}$ and $EGFR^{\Delta hep}$ mice 36, 48, and 72 hours after intoxication with DEN. (G) Livers lacking EGFR expression ($EGFR^{\Delta liv}$ and $EGFR^{\Delta hep}$) show elevated numbers of Caspase-3 positive cells per high power field (HPF) 24, 48, and 96 hours after treatment with DEN (100 mg/kg body weight). (H) qRT-PCR showing IL-1β and IL-1α expression in hepatocytes isolated 6 and 48 hours after DEN intoxication in vivo. (I) qRT-PCR for IL-1β and IL-1α of total liver of $EGFR^{f/f}$, $EGFR^{\Delta hep}$, and $EGFR^{\Delta liv}$ mice after 24 hours intoxication with DEN. (J) Quantification of IL-1β transcription in liver tumors of the indicated genotypes. Data (F-J) represent mean±s.d of at least 3 independent samples. Student's t-test for independent samples and unequal variances was used to assess statistical significance (*p<0.05, p<0.01, *p<0.001).

Figure 3:
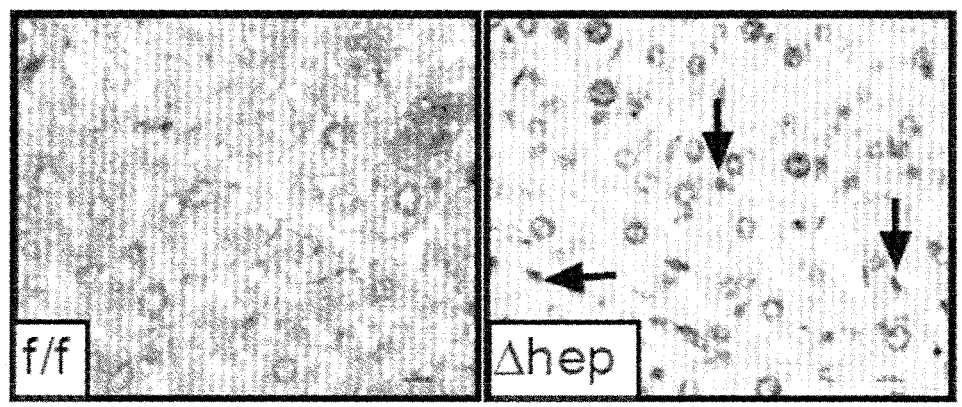
Figure 3:
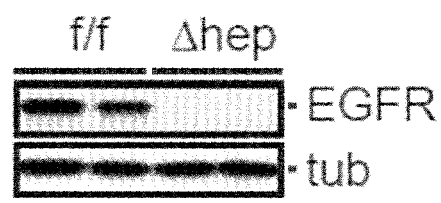
Figure 3:
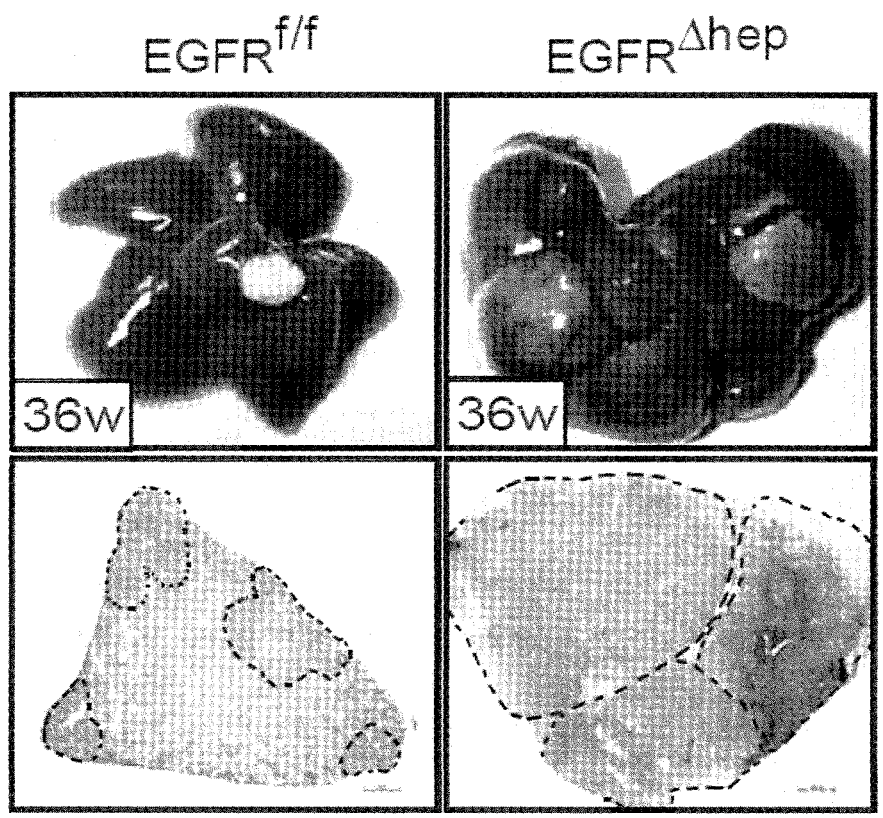
Figure 3:
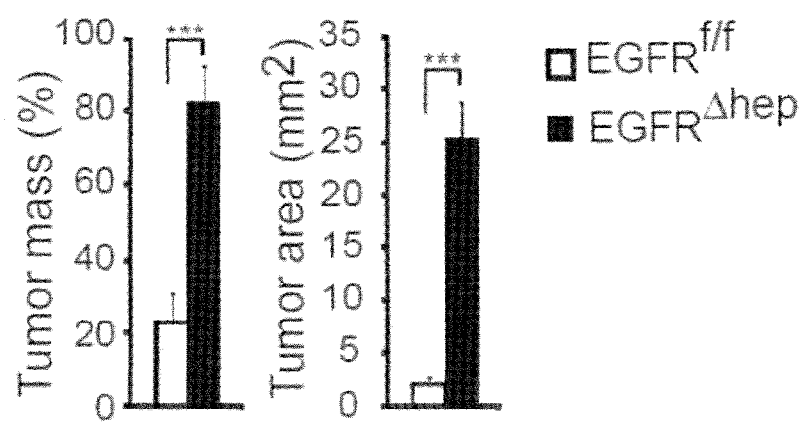
Figure 3:
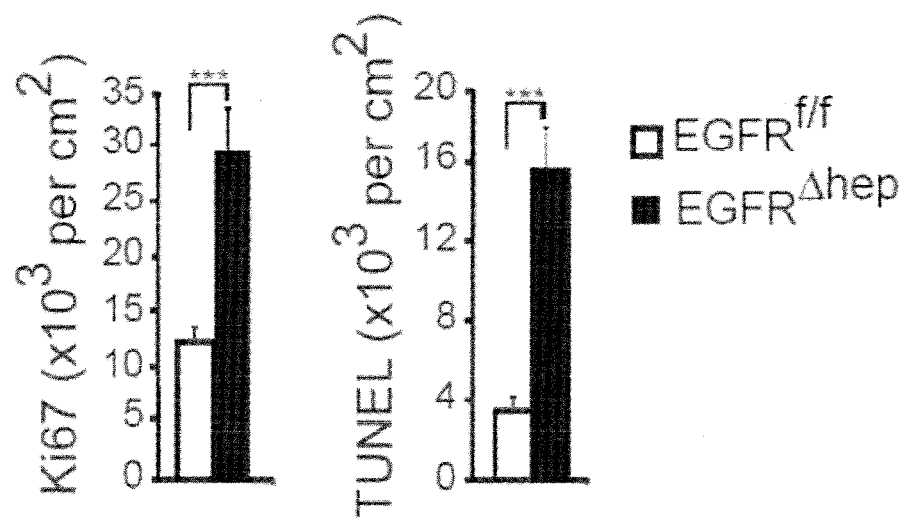
Figure 3:
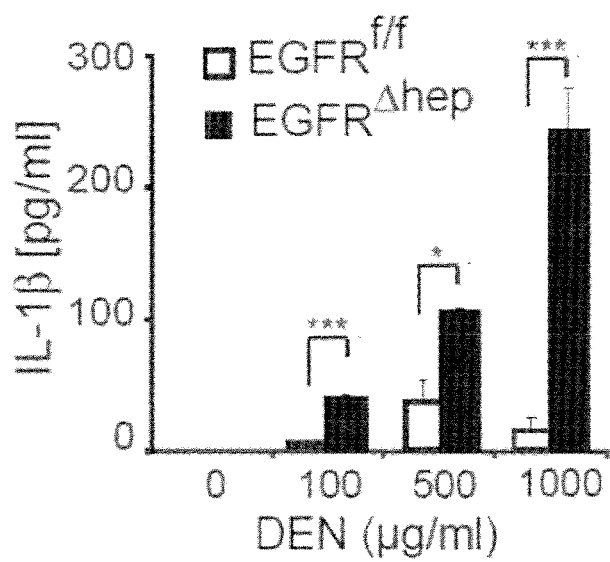

FIG. 3: Increased HCC formation in mice lacking EGFR in hepatocytes. (A) EGFR staining on liver tumor sections from $EGFR^{f/f}$ (left) and $EGFR^{\Delta hep}$ (right) mice. Arrows point to EGFR expressing non-parenchymal cells. (B) Western Blot of tumors showing absence of EGFR expression in $EGFR^{\Delta hep}$ HCCs. (C) Representative livers (top) and H&E staining of liver sections (bottom) of $EGFR^{f/f}$ and $EGFR^{\Delta hep}$ mice at 36 weeks after DEN/PB carcinogenesis. Magnification 10x. (D) Tumor mass (left) and area (right) in livers of $EGFR^{f/f}$ (n=12) and $EGFR^{\Delta hep}$ (n=14) mice 36 weeks after tumor initiation. (E) Ki67-positive (left) and TUNEL-positive cells (right) in tumors of the indicated genotypes. $EGFR^{f/f}$ (n=12) and $EGFR^{\Delta hep}$ (n=14). (F) ELISA showing IL-1 in the supernatant of primary hepatocyte cultures 4 hours after incubation with increasing amounts of DEN in vitro. Data (E, F) represent mean±s.d. Student's t-test for independent samples and unequal variances was used to assess statistical significance (*p<0.05, p<0.01, *p<0.001).

Figure 4:
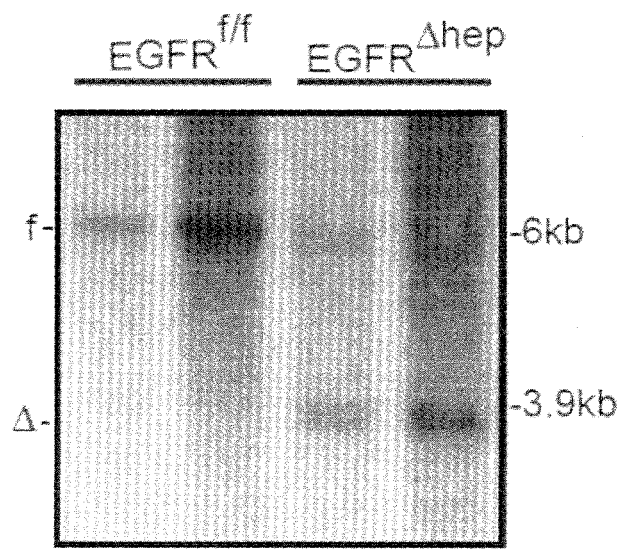
Figure 4:
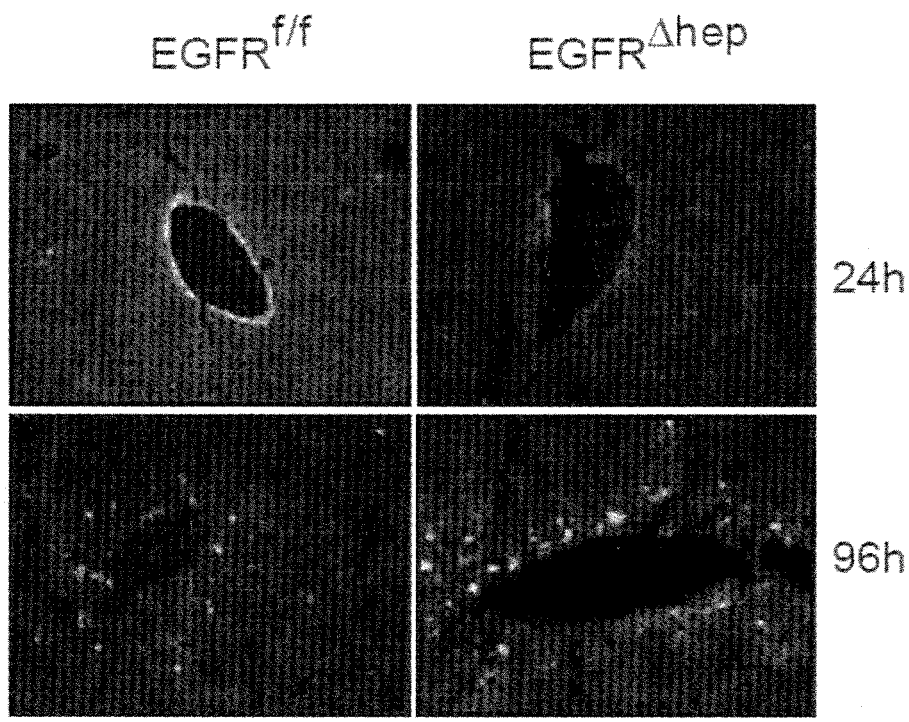
Figure 4:
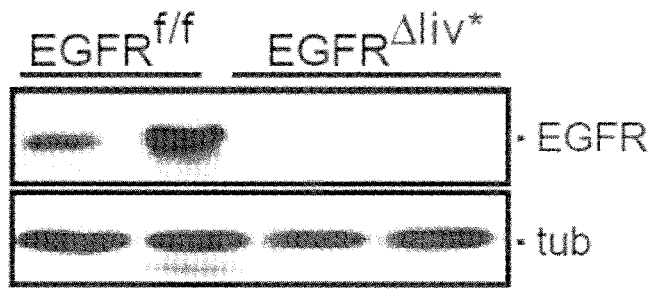
Figure 4:
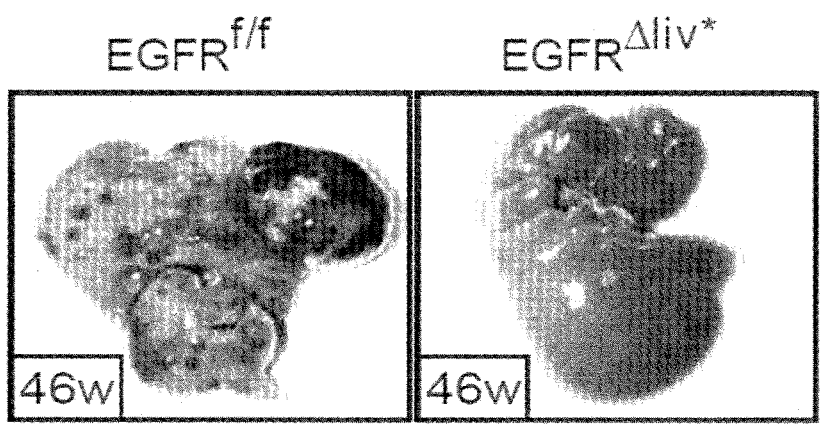
Figure 4:
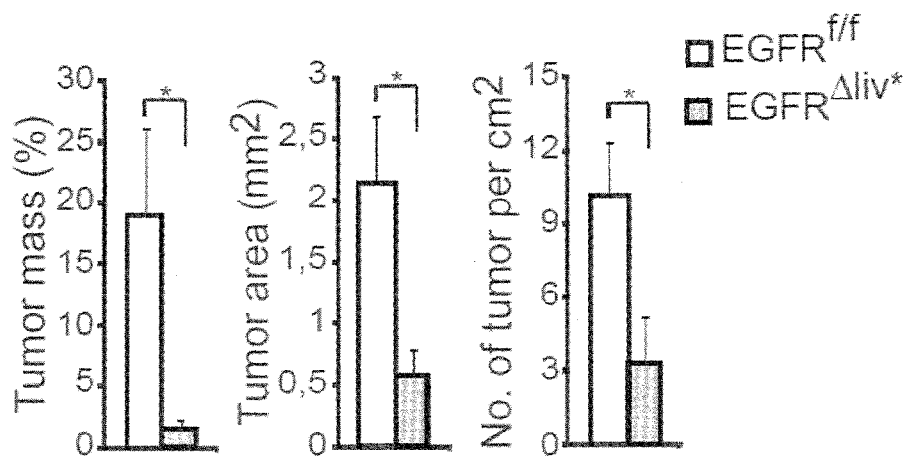

FIG. 4: EGFR deletion in $EGFR^{\Delta hep}$ mice and apoptosis in vivo upon DEN Injection. (A) Southern Blot analysis showing efficient deletion of EGFR in $EGFR^{\Delta hep}$ livers (f: floxed EGFR allele, Δ: Cre-deleted EGFR allele). Since Alfp-Cre is not expressed in non-parenchymal cells, the non-recombined EGFR allele deriving from these cells is visible. (B) Active caspase-3 staining (Alexa 488) and nuclei (DAPI) of $EGFR^{f/f}$ and $EGFR^{\Delta hep}$ liver sections 24 and 96 hours after DEN intoxication, showing increased apoptosis in EGFR-deficient livers after 96 hours. (C) Western Blot analysis showing efficient deletion of EGFR in livers of $EGFR^{\Delta liv*}$ mice. (D) Livers of $EGFR^{f/f}$ (left) and $EGFR^{\Delta liv*}$ (right) mice 46 weeks after tumor initiation. (E) Tumor mass (left), area (middle), and number (right) is significantly decreased in livers of $EGFR^{\Delta liv*}$ mice. Data represent mean±s.e.m. Student's t-test for independent samples and unequal variances was used to assess statistical significance (*p<0.05, p<0.01, *p<0.001).

Figure 5:
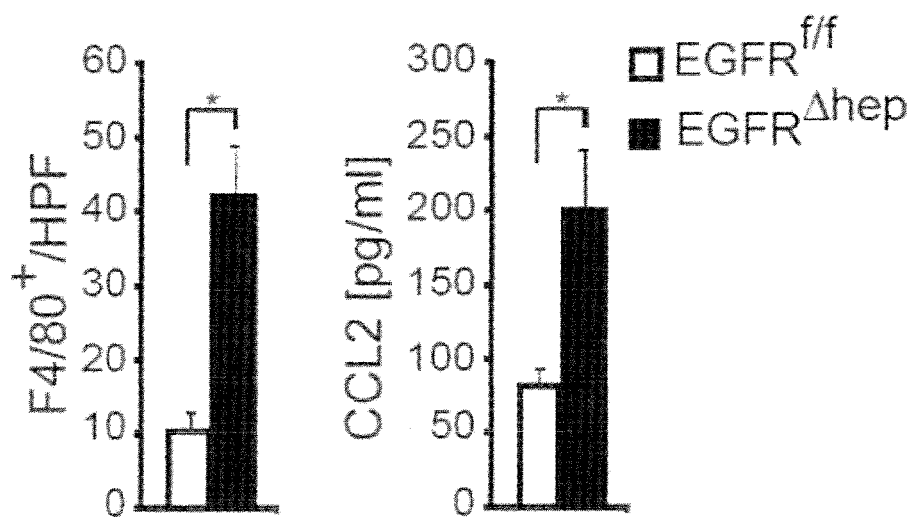
Figure 5:
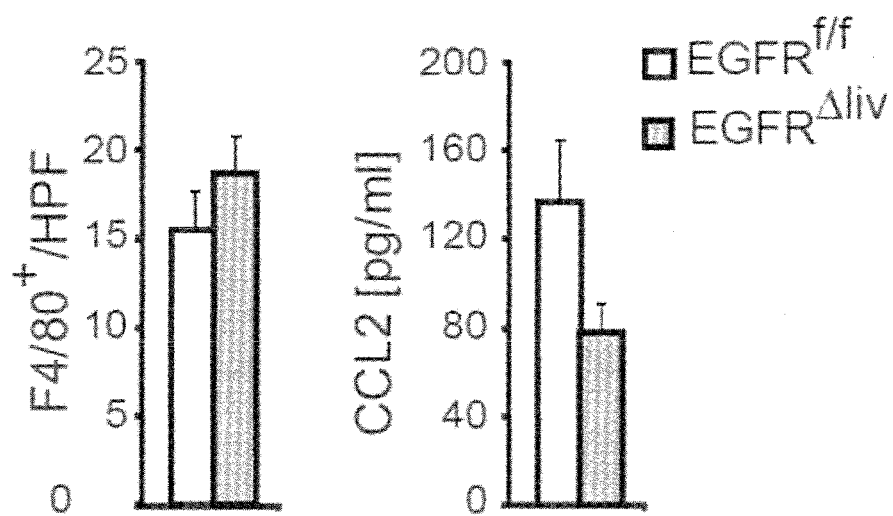
Figure 5:
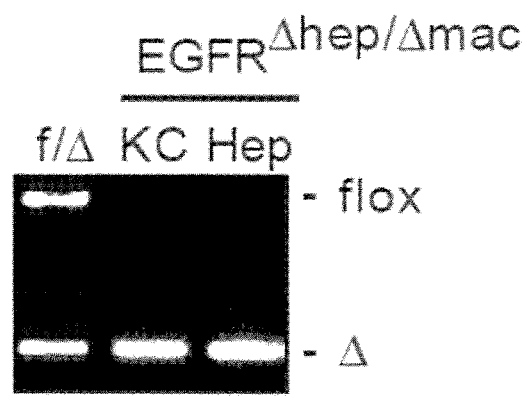
Figure 5:
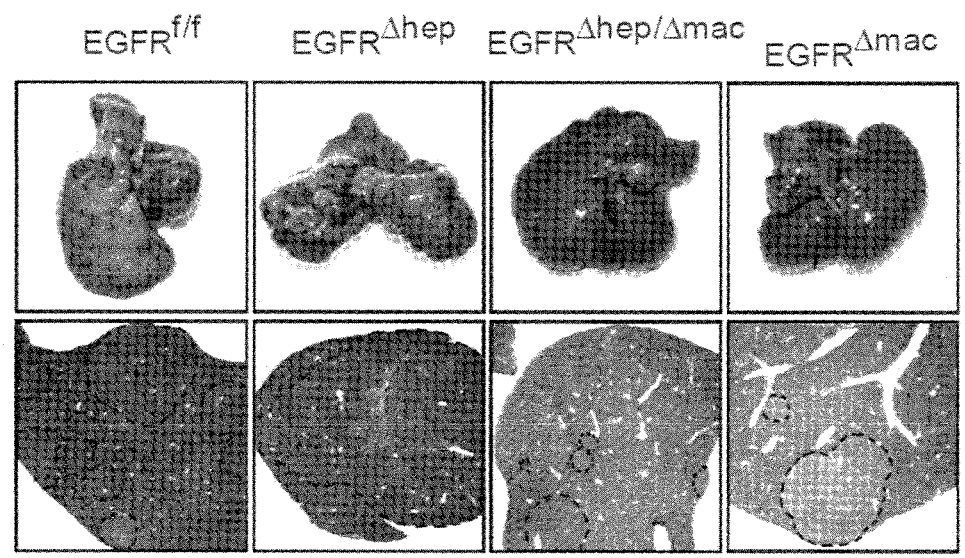
Figure 5:
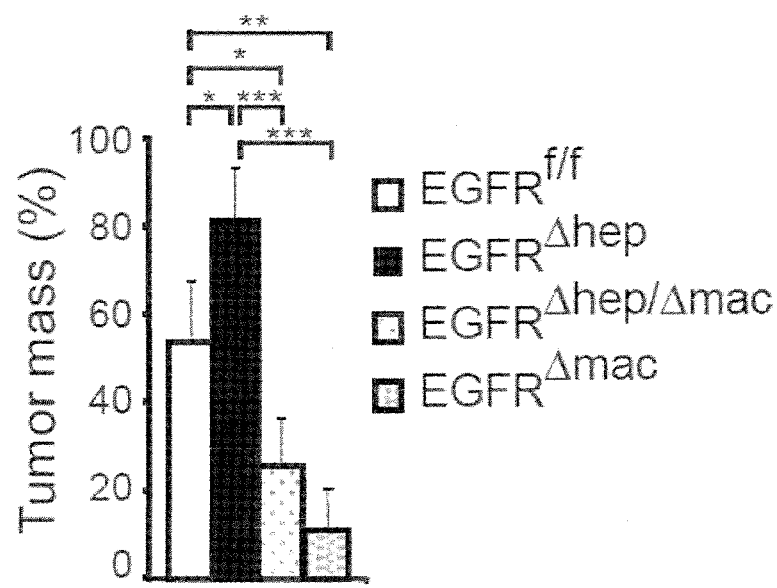
Figure 5:
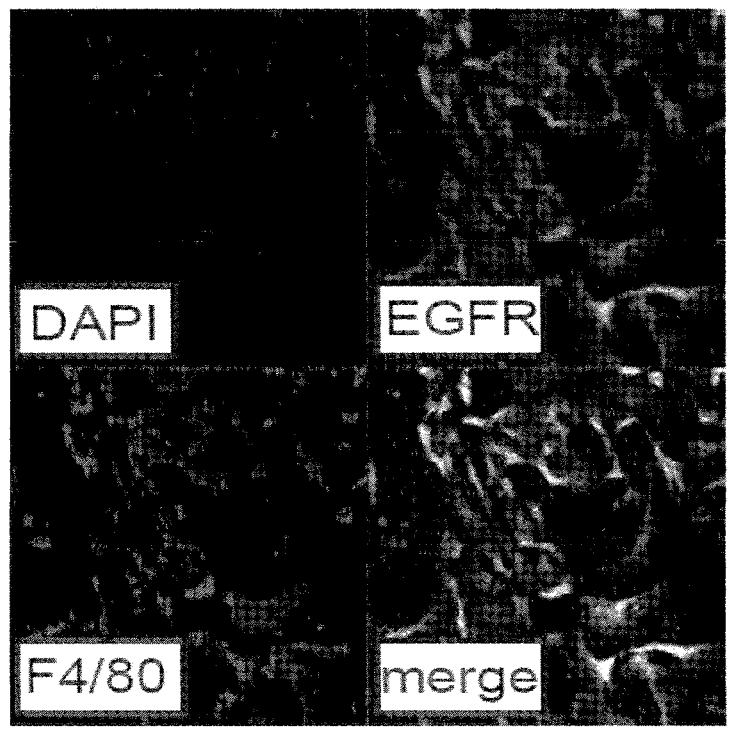
Figure 5:
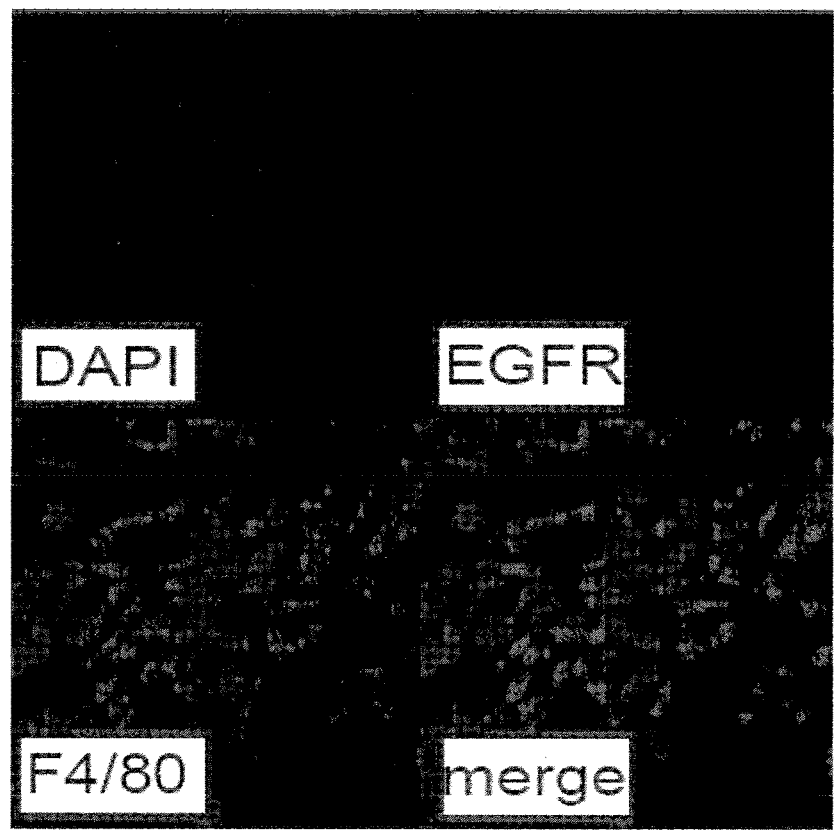
Figure 5:
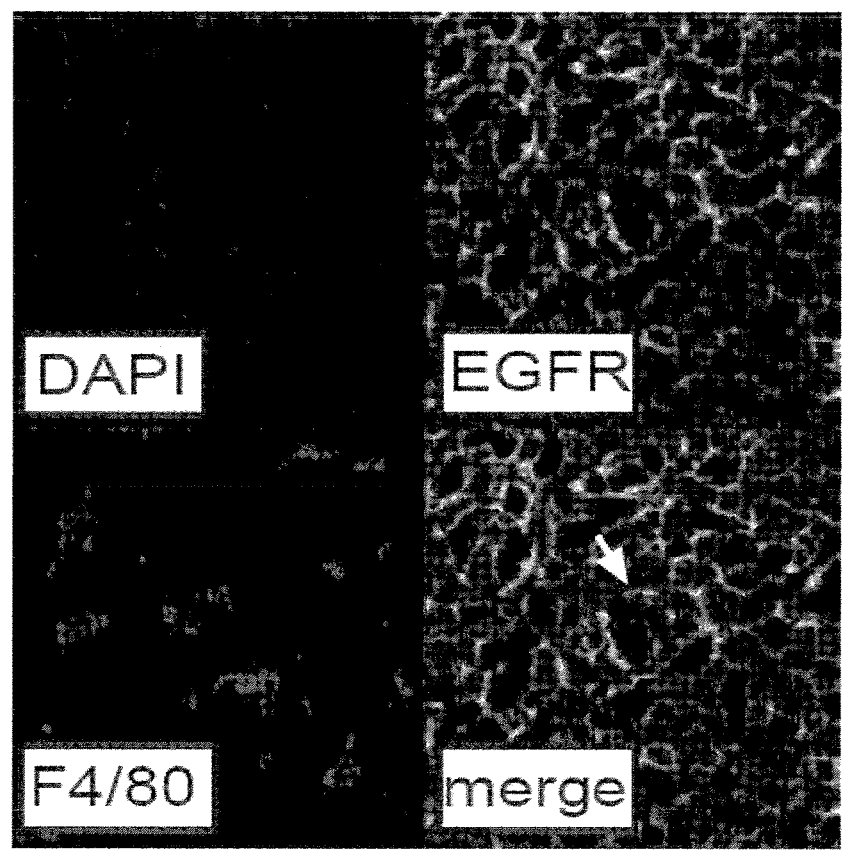
Figure 5:
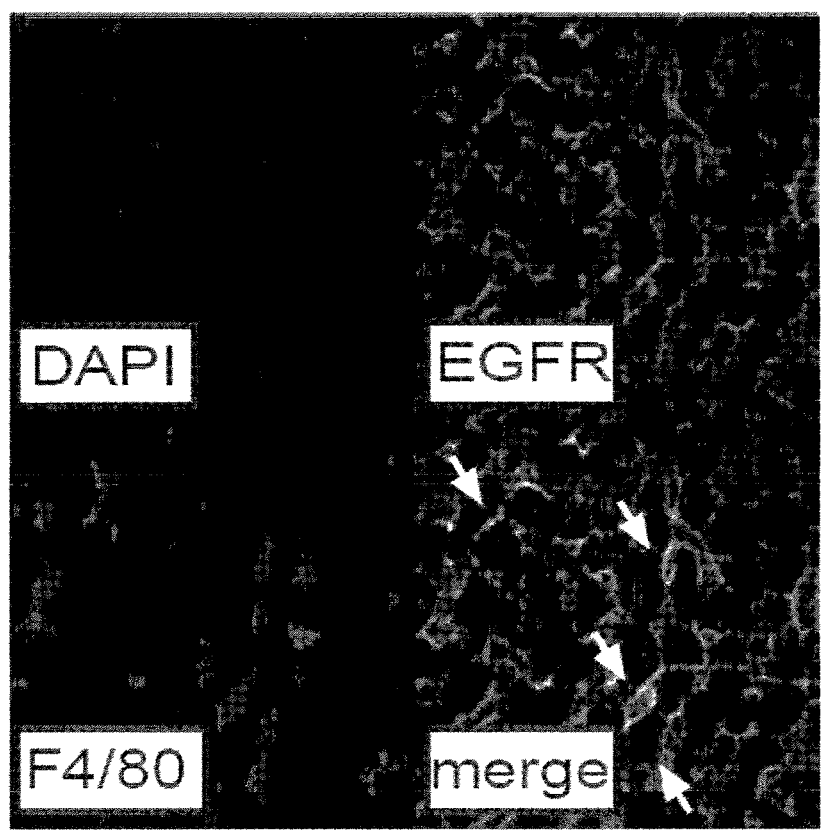
Figure 5:
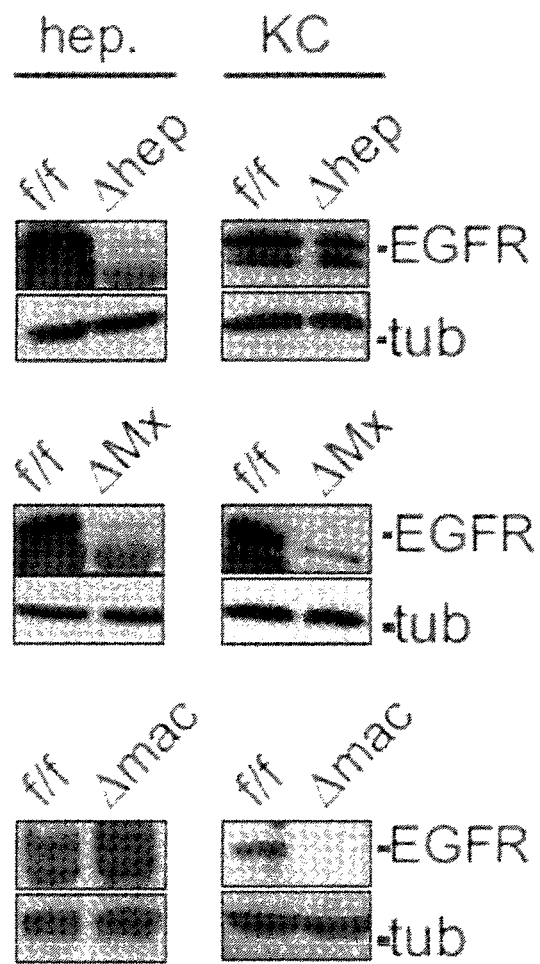
Figure 5:
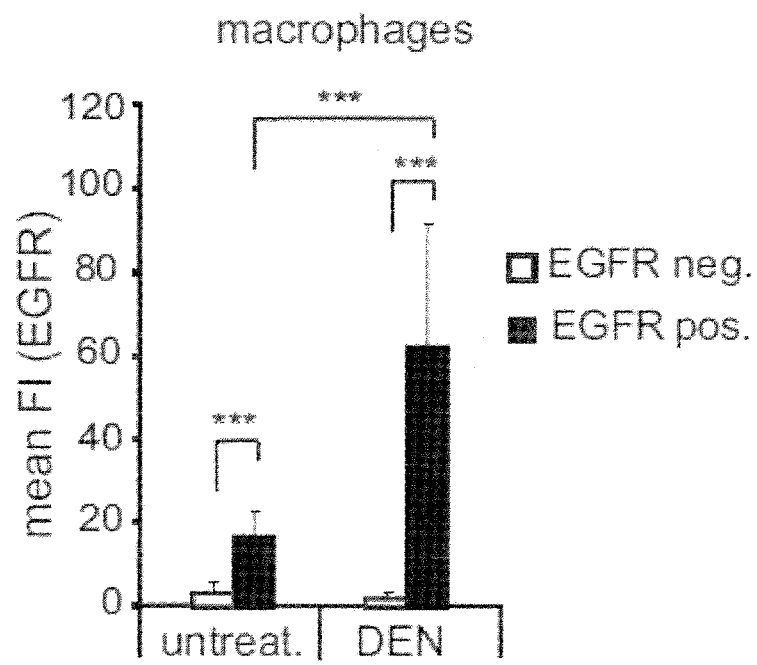
Figure 5:
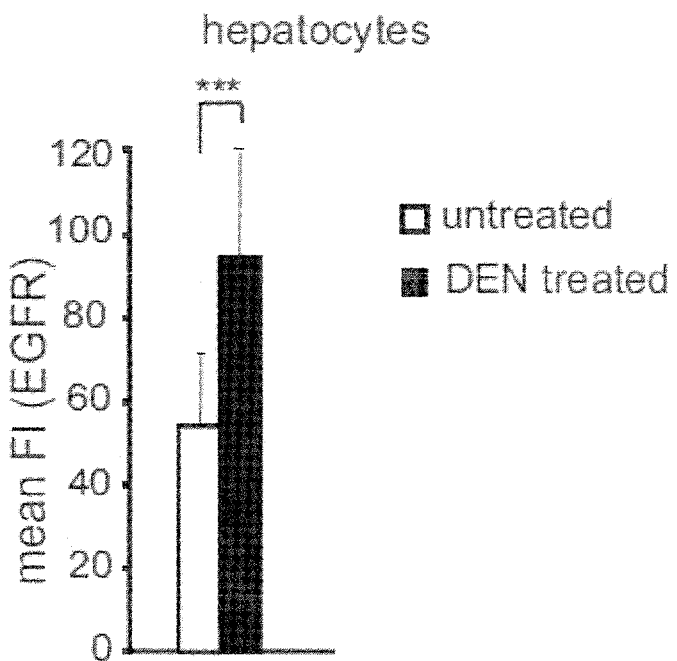
Figure 5:
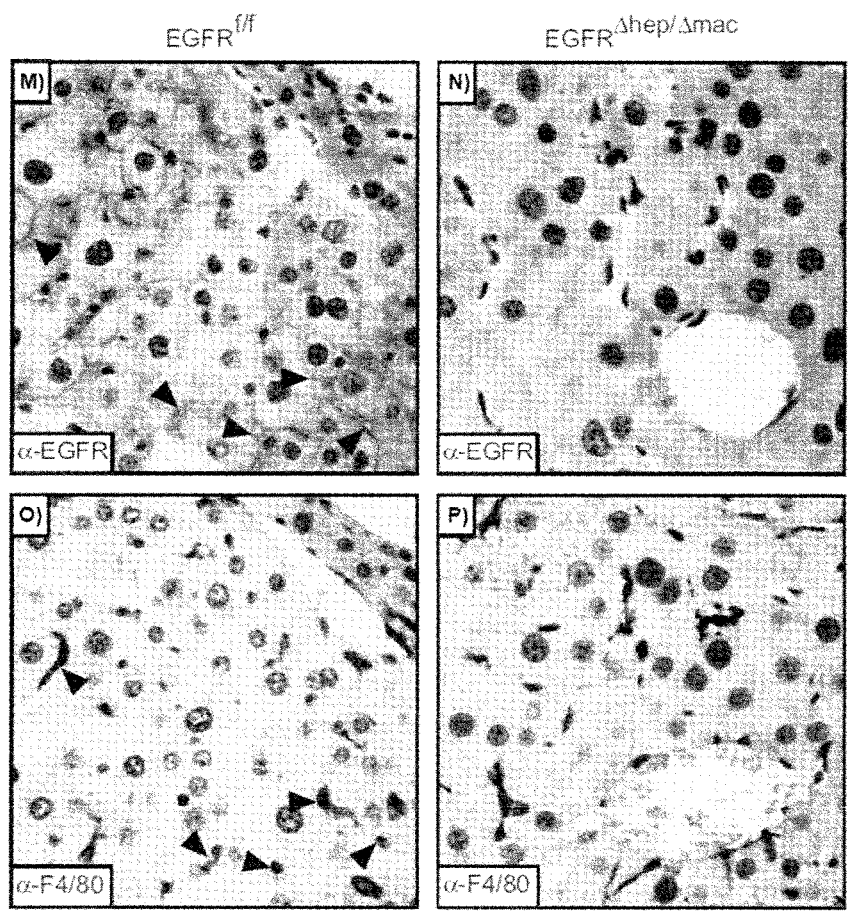

FIG. 5: EGFR expression in Kupffer cells/liver macrophages promotes HCC development (A, B) Numbers of F4/80$^+$ cells (left) in tumors and levels CCL2 serum levels (right) of mice of the indicated genotypes. (C) PCR showing EGFR deletion in isolated hepatocytes (Hep) and Kupffer cells (KC) of control (f/Δ) and EGFR$^{\Delta hep\Delta mac}$ mice. Flox=not deleted and Δ=deleted EGFR. (D) Representative image (top) and H&E staining of sections (bottom) of EGFR$^{f/f}$, EGFR$^{\Delta hep}$ EGFR$^{\Delta hep/\Delta mac}$ and EGFR$^{\Delta mac}$ livers at 63 weeks after tumor initiation. Magnification 10×. Dotted lines show tumor nodules. Note: tumors of EGFR$^{f/f}$ mice are bigger than the ones shown in FIGS. 3C and 3D because the mice were analyzed 27 weeks later. (E) Quantification of tumor mass on H&E stained liver sections of the indicated genotype. Data (A, B, E) represent mean±s.d. Student's t-test for independent samples and unequal variances was used to assess statistical significance (*p<0.05, p<0.01, *p<0.001). (F-G) Confocal images of cultured Kupffer cells/liver macrophages isolated from EGFR$^{f/f}$ (F) and EGFR$^{\Delta mac}$ (G) livers showing EGFR expression in EGFR$^{f/f}$ but not in EGFR$^{\Delta mac}$ Kupffer cells. (H-I) Confocal images showing F4/80 and EGFR expression in liver sections of untreated mice (H), and liver sections of mice after 5 days DEN treatment (I). White arrows (H, I) point to EGFR positive Kupffer cells. Nuclei (DAPI), EGFR (Alexa 488) and F4/80 (Alexa 594) merge (bottom right), Magnification 250×. (J) Western Blot analysis showing EGFR expression in isolated hepatocytes and Kupffer cells of EGFR$^{f/f}$, EGFR$^{\Delta Mx}$, EGFR$^{\Delta hep}$ and EGFR$^{\Delta mac}$ mice. (K-L) Mean fluorescence intensity (FI) showing EGFR (Alexa 488) expression levels in liver macrophages (K) and hepatocytes (L) of immunofluorescent stainings shown in (H) and (I). (M-P) Representative anti-EGFR (M, N) and anti-F4/80 (O, P) staining performed on serial sections of control (M, O) and EGFR$^{\Delta hep/\Delta mac}$ (N, P) HCC showing EGFR expression in tumor cells and co-expression of EGFR and F4/80 in Kupffer cells/liver macrophages of EGFR$^{f/f}$ HCC and no EGFR expression in EGFR$^{\Delta hep/\Delta mac}$ tumors. Magnification 40×.

Figure 6:
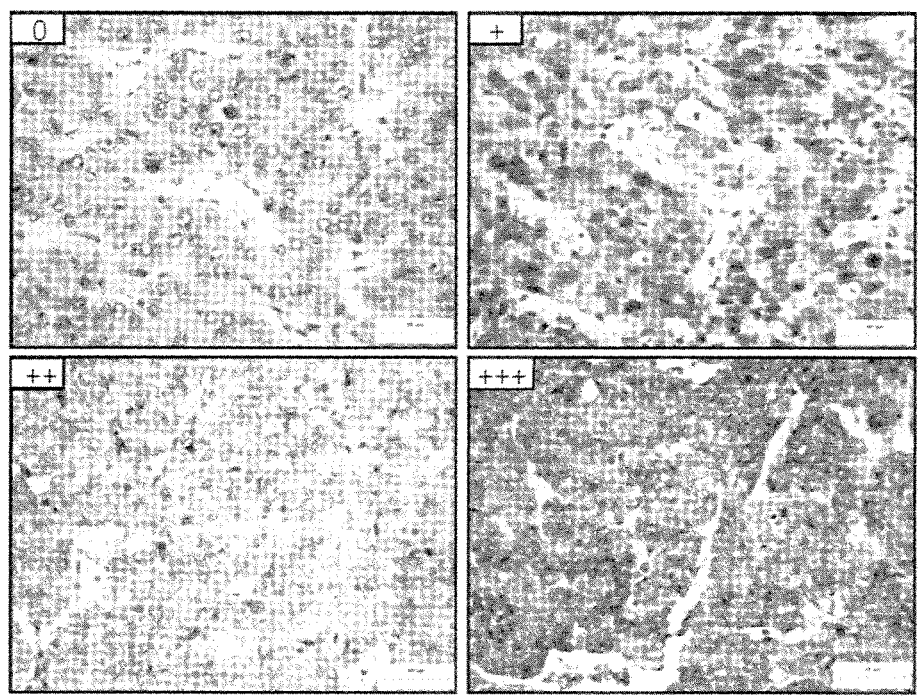
Figure 6:
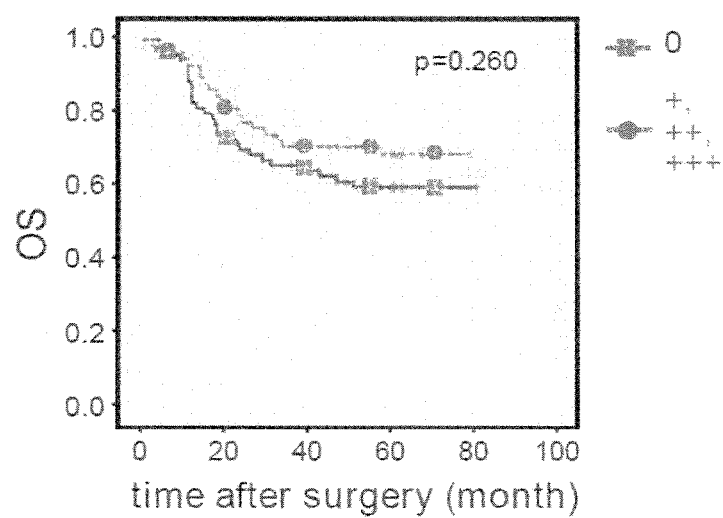
Figure 6:
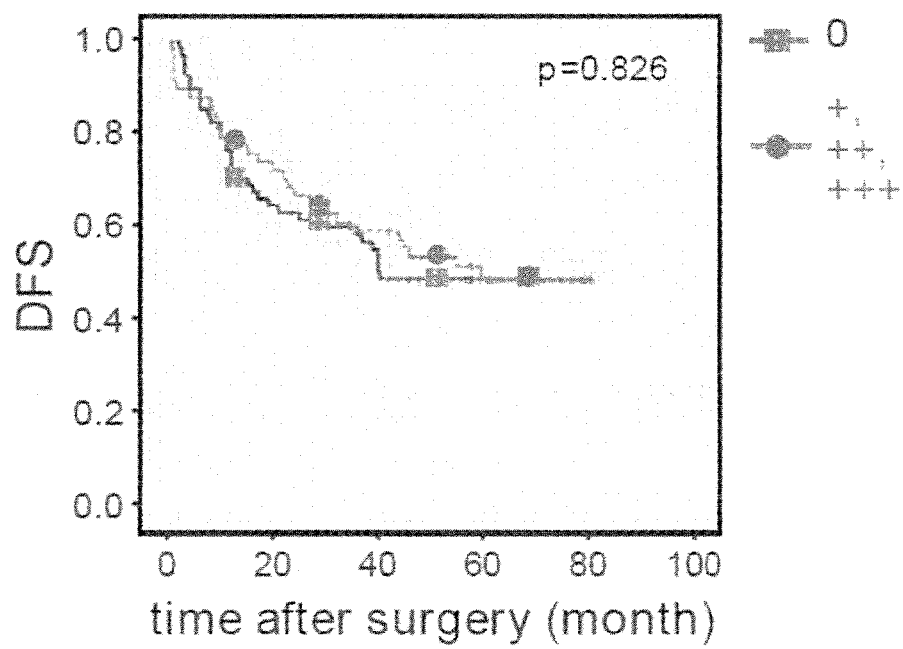
Figure 6:
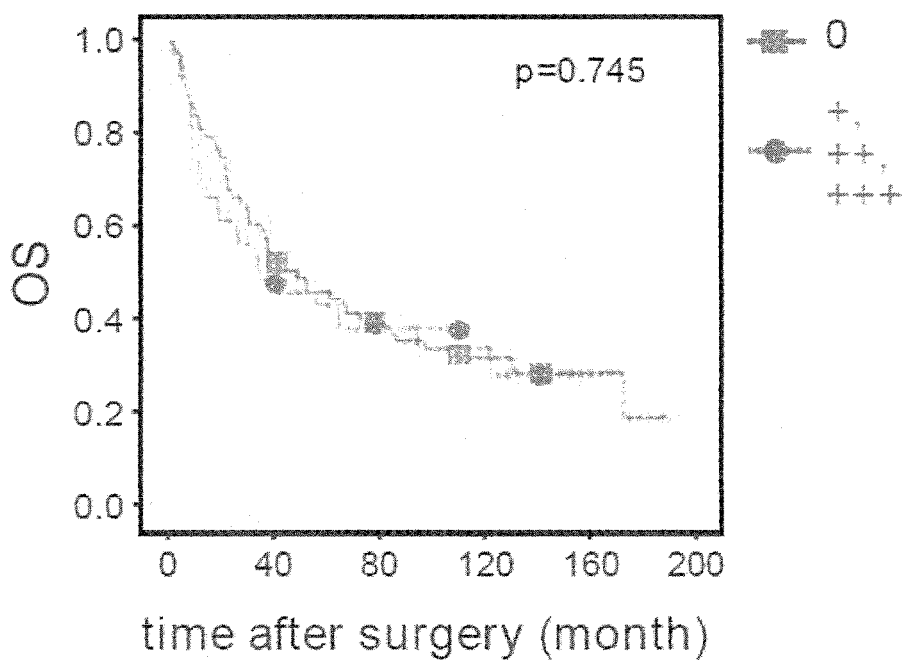
Figure 6:
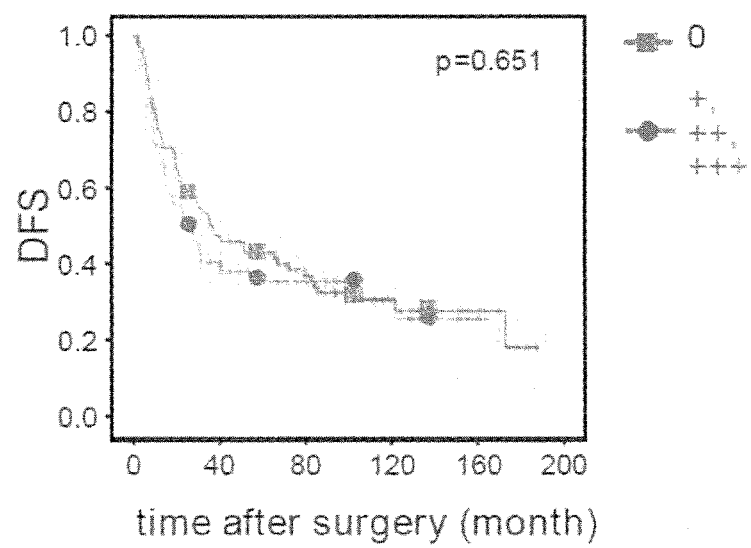
Figure 6:
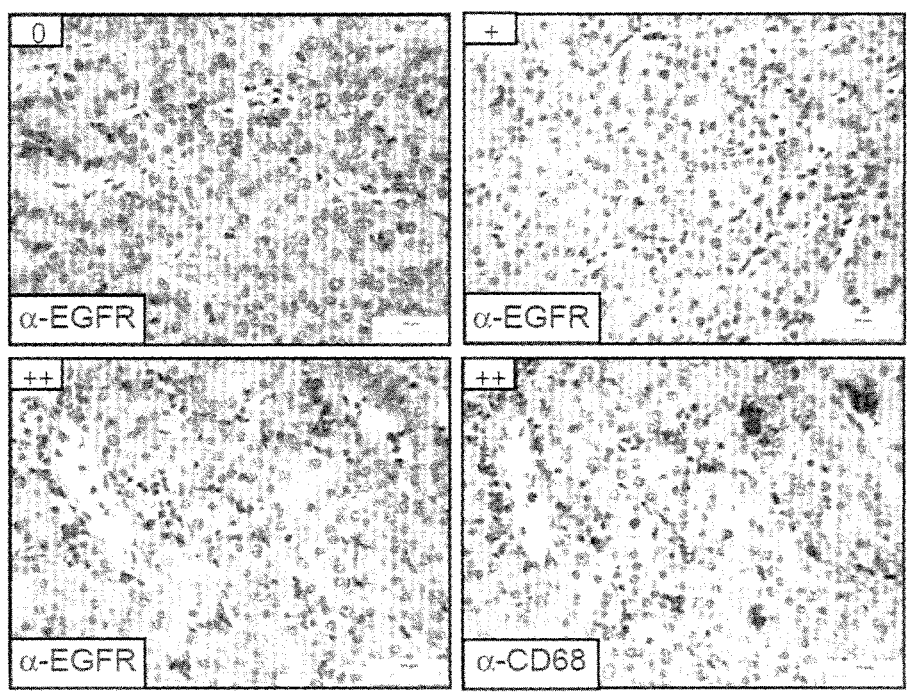
Figure 6:
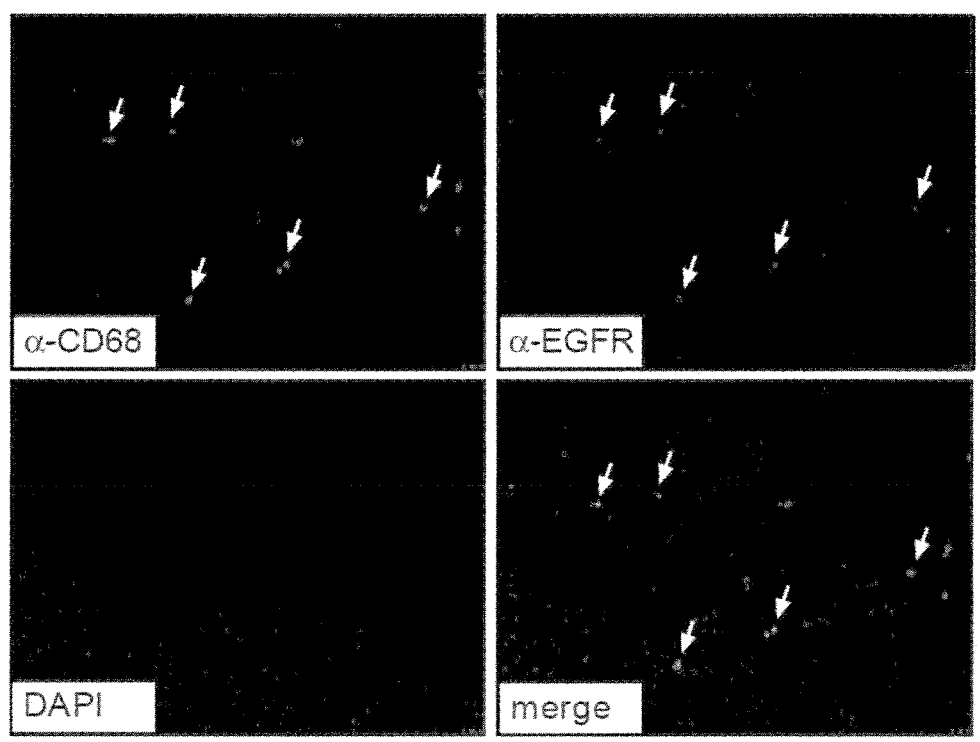

FIG. 6: EGFR expression in tumor cells and Kupffer cells of human HCCs. (A) Representative IHC staining showing EGFR expression in tumor cells/hepatocytes of HCC. Scoring (0, +, ++, +++) was performed according to the scale described in the examples resulting in the generation of Table 1a. (B-E) OS (B, D) and DFS (C, E) of HCC patients of the Chinese (B, C) and European cohorts (D, E) with or without EGFR expression in hepatocytes. (F) IHC showing EGFR and CD68 stainings (0, +, ++) in liver macrophages of human HCC. The scoring system is described in the examples section. This evaluation was employed to generate Table 1b. (G) Representative EGFR and CD68 co-staining in fresh frozen human HCC tissue. White arrows indicate double positive cells. Scoring system: 0=negative staining (0%-10% positive), 1=weak signal (10%-20% positive), 2=intermediate signal (20%-50% positive) and 3=strong signal (>50% positive) as previously described (Wang, K. et al., 2010).

Figure 7:
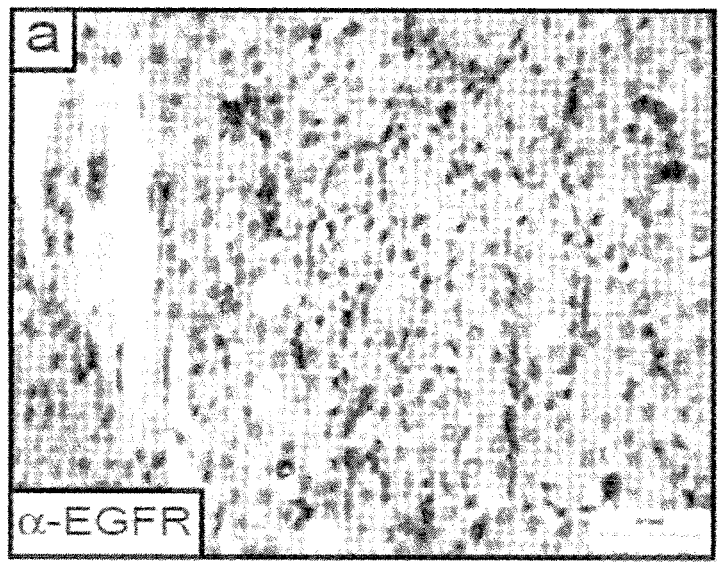
Figure 7:
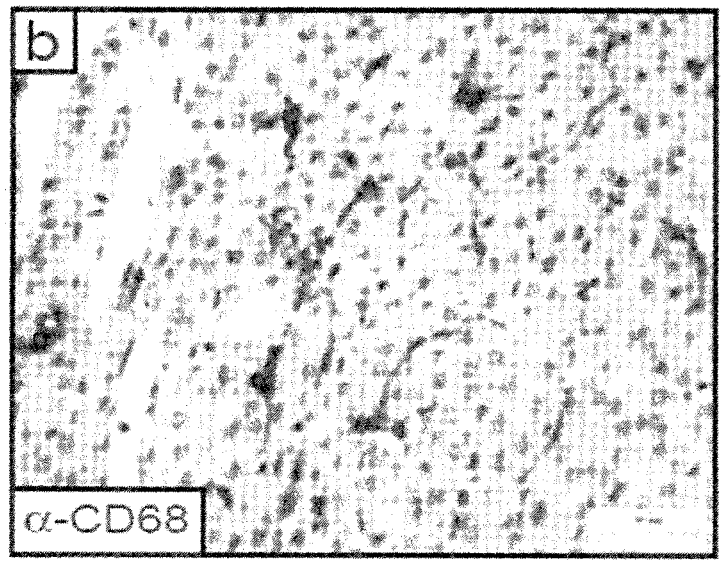
Figure 7:
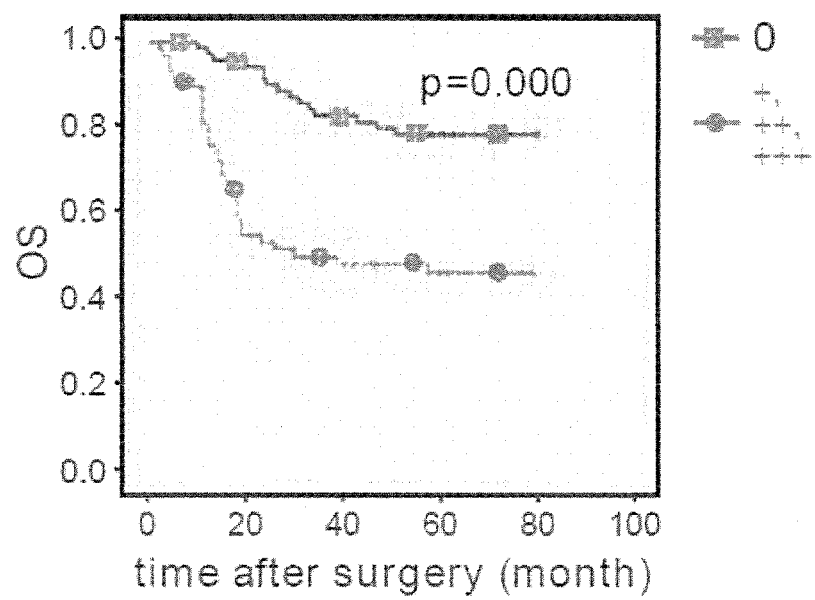
Figure 7:
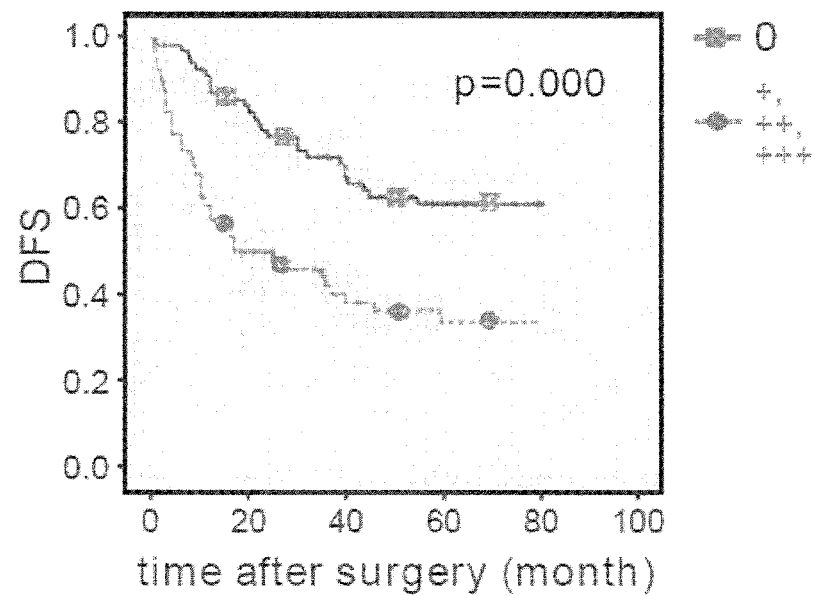
Figure 7:
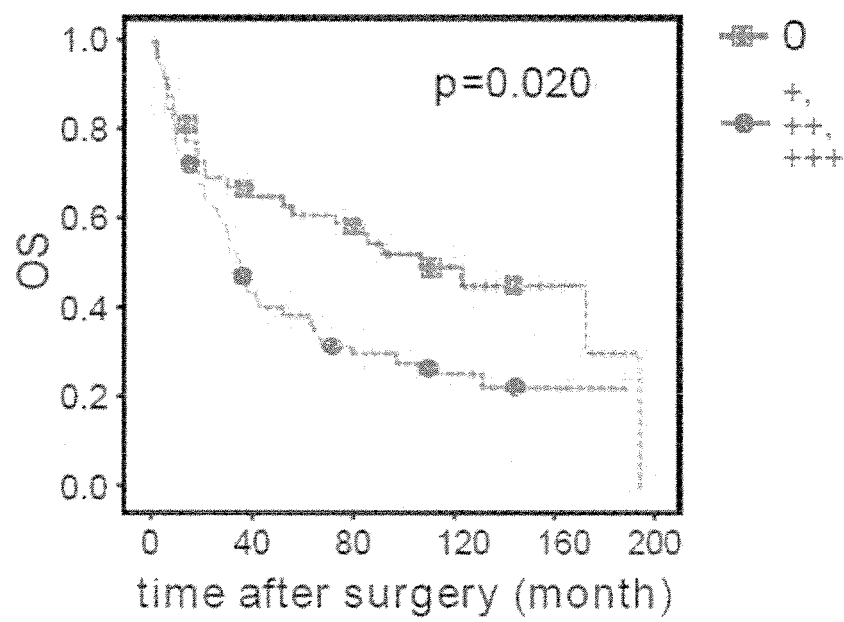
Figure 7:
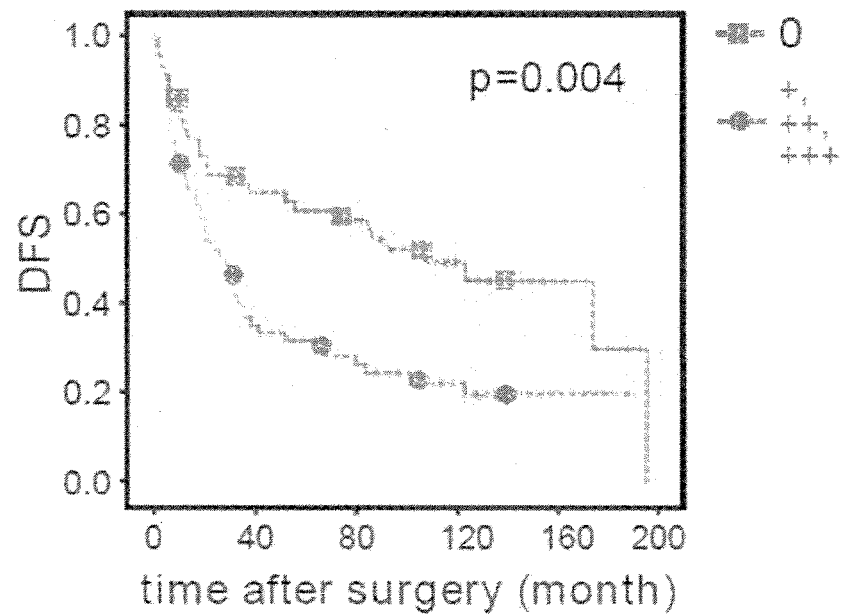
Figure 7:
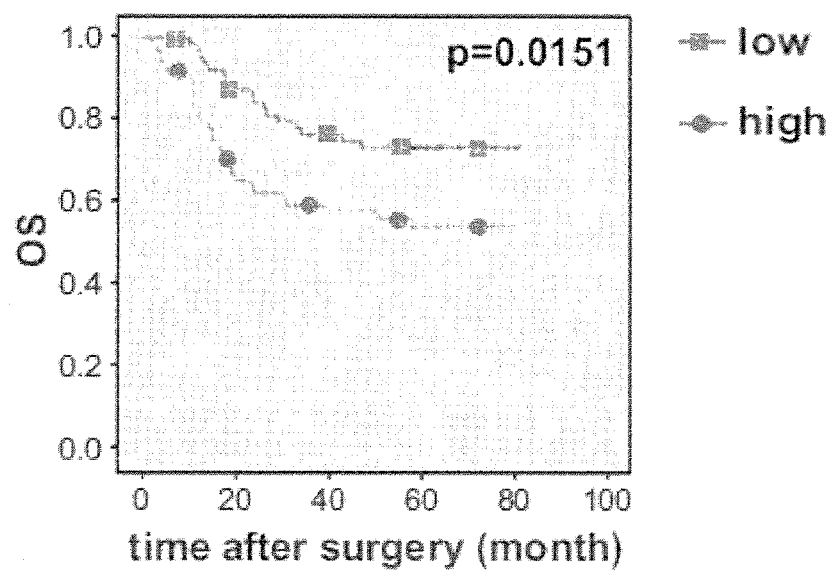
Figure 7:
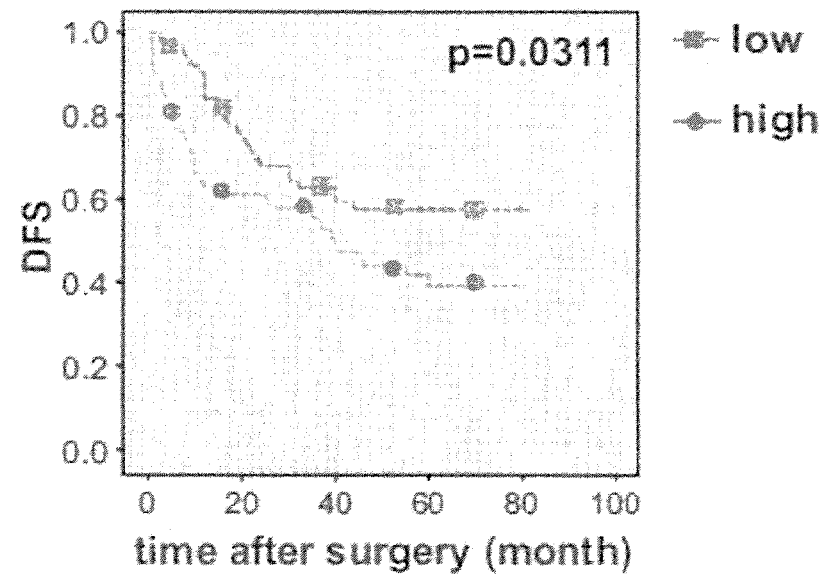
Figure 7:
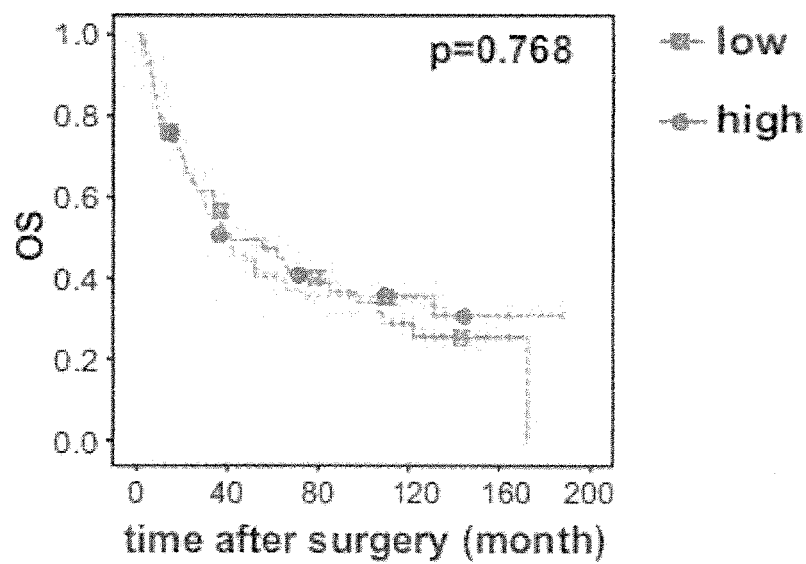
Figure 7:
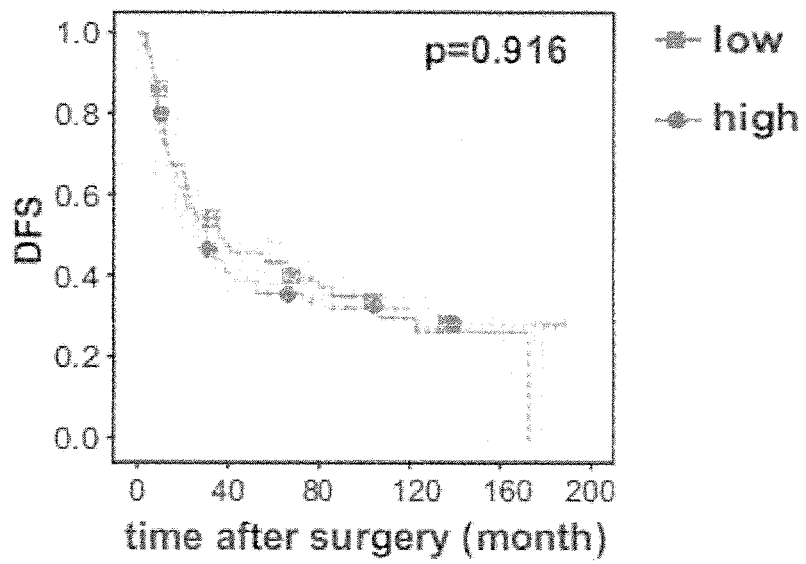

FIG. 7: EGFR expression in Kupffer cells of HCC patients correlates with poor prognosis. (A-B) EGFR and CD68 staining on serial sections revealing Kupffer cells in human HCC samples. (C-F) Overall survival (OS, C, E) and disease free survival (DFS, D, F) of HCC patients with (+, ++, +++) or without (0) EGFR expression in Kupffer cells/liver macrophages in the Chinese (C, D) and European (E, F) cohort. Scoring system: 0=negative staining (0%-10% positive), 1=weak signal (10%-20% positive), 2=intermediate signal (20%-50% positive) and 3=strong signal (>50% positive) as previously described (Wang, K. et al., 2010). (G-J) Overall survival (OS, G, I) and disease free survival (DFS, H, J) of HCC patients of the Chinese (G, H) and European (I, J) cohort with low or high numbers of Kupffer cells/liver macrophages in tumors. The cut-off value for defining high and low was the median. For the respective patient cohorts, low was classified as values below or at the 50th percentile and high was classified as values above the 50th percentile.

Figure 8:
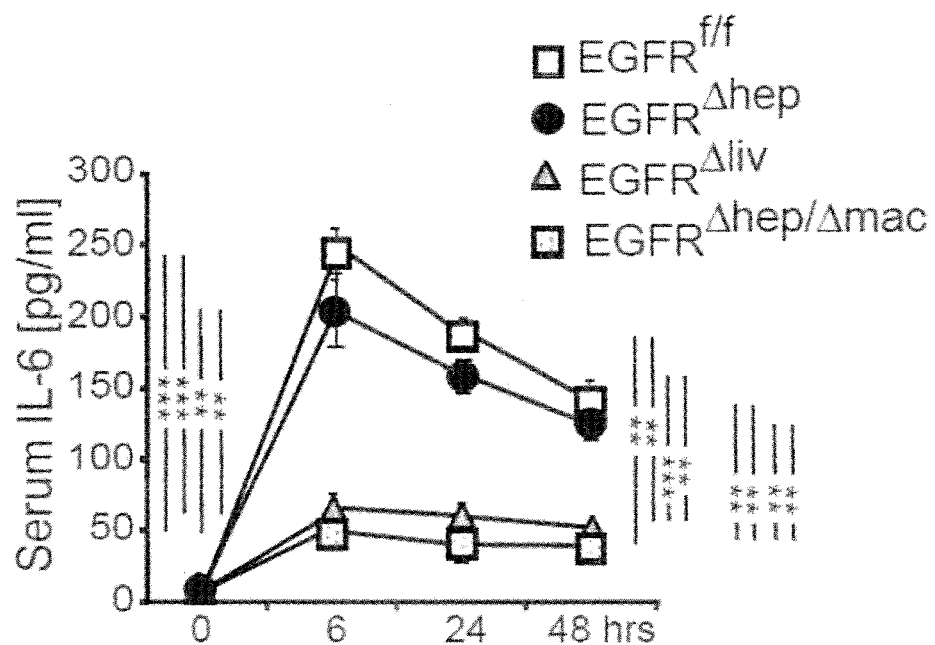
Figure 8:
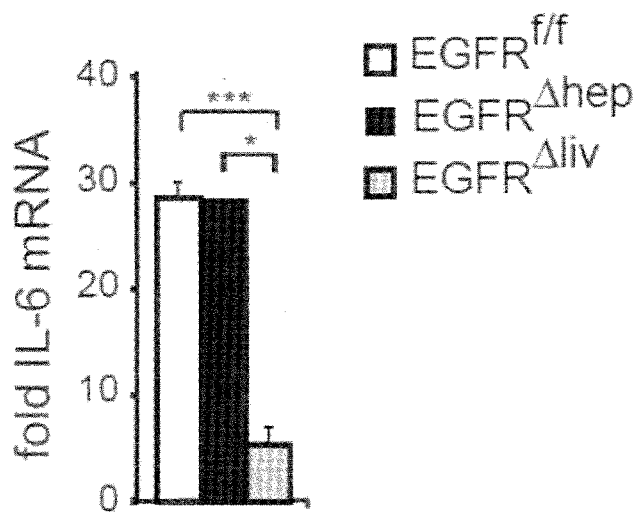
Figure 8:
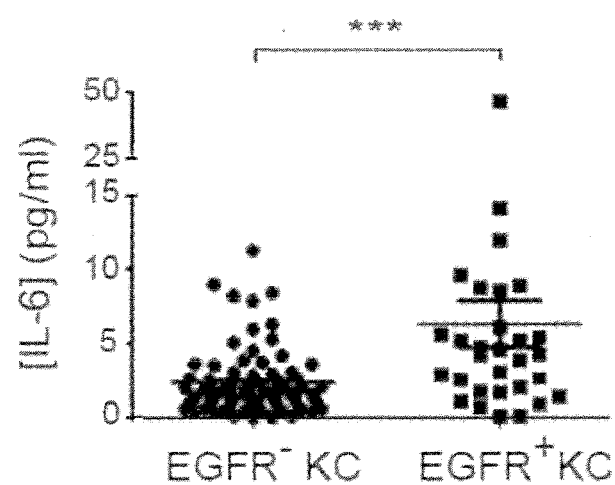
Figure 8:
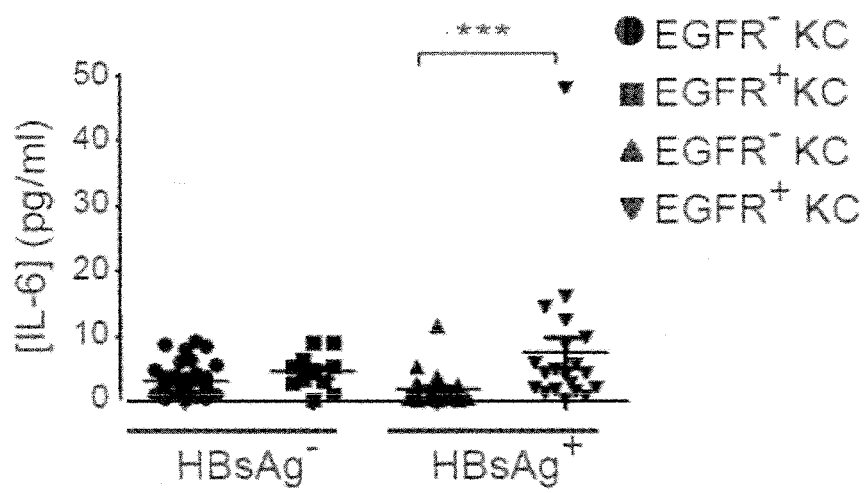
Figure 8:
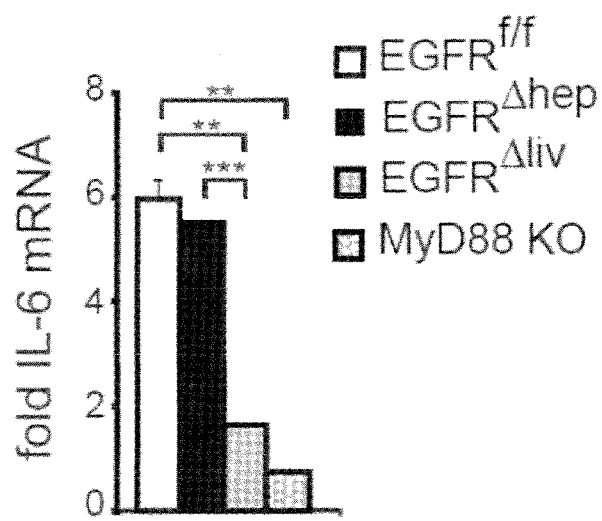
Figure 8:
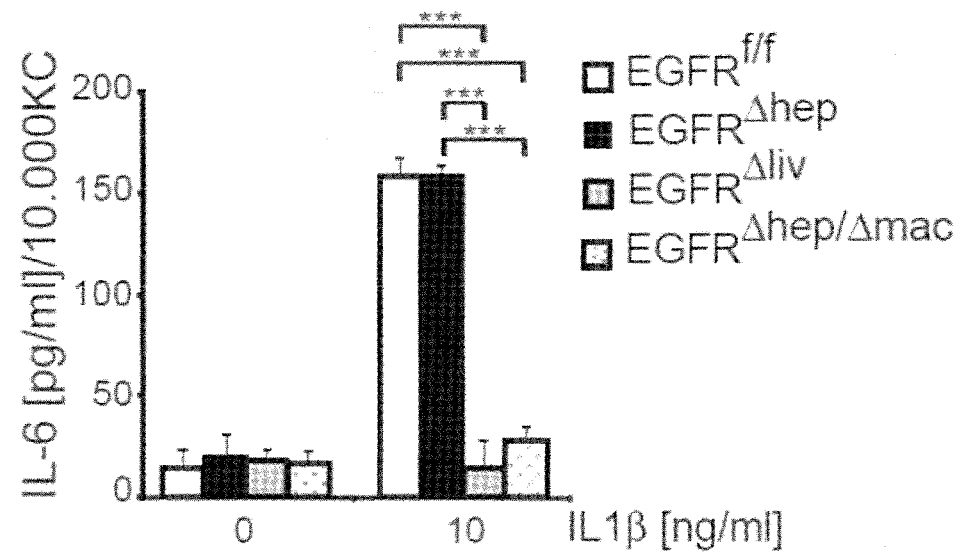
Figure 8:
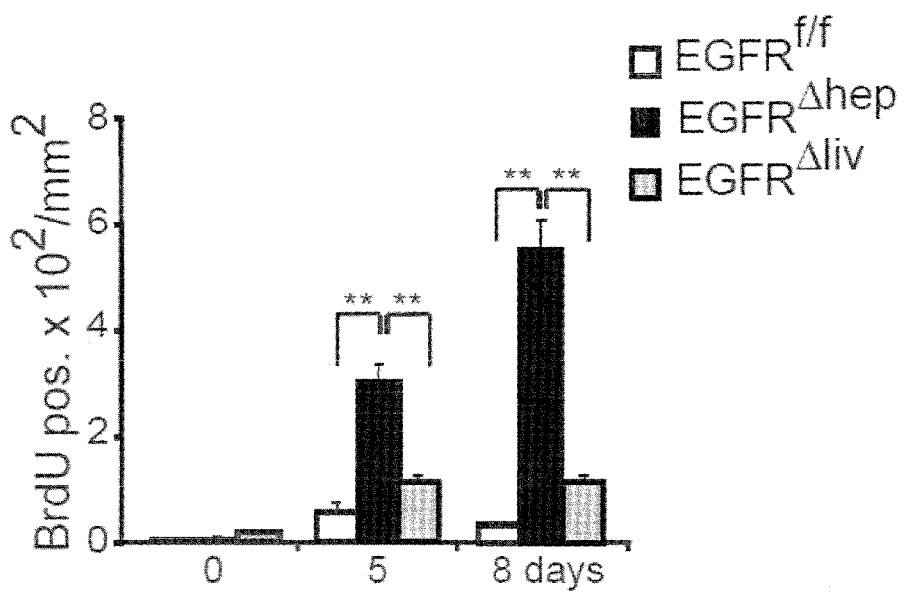

FIG. 8: EGFR-dependent IL-6 production and release. (A) ELISA showing IL-6 serum levels in EGFR$^{f/f}$, EGFR$^{\Delta hep}$, EGFR$^{\Delta liv}$, and EGFR$^{\Delta hep/\Delta mac}$ mice 6, 24, and 48 hours after DEN injection in vivo. (B) qRT-PCR showing IL-6 transcription in isolated Kupffer cells 6 hours after DEN injection in vivo. (C-D) IL-6 plasma levels in HCC patients (n=104) of the Chinese cohort grouped according to the presence of EGFR-positive or EGFR-negative Kupffer cells in tumors (C) or additionally considering positivity for HBsAg (D). (E) qRT-PCR showing IL-6 transcription in isolated Kupffer cells after 6 hours incubation with IL-1β in vitro. IL-6 is strongly reduced in Kupffer cells lacking EGFR (EGFR$^{\Delta liv}$) or deficient for IL-1 signaling (MyD88$^{-/-}$). (F) IL-6 release into the supernatant by cultured Kupffer cells 24 hours after incubation with IL-1β in vitro is dependent on EGFR expression. (G) Quantification of BrdU positive cells in liver sections of mice 5 and 8 days after DEN injection. Data represent mean±s.d. Student's t-test for independent samples and unequal variances was used to assess statistical significance (*p<0.05, p<0.01, *p<0.001).

Figure 9:
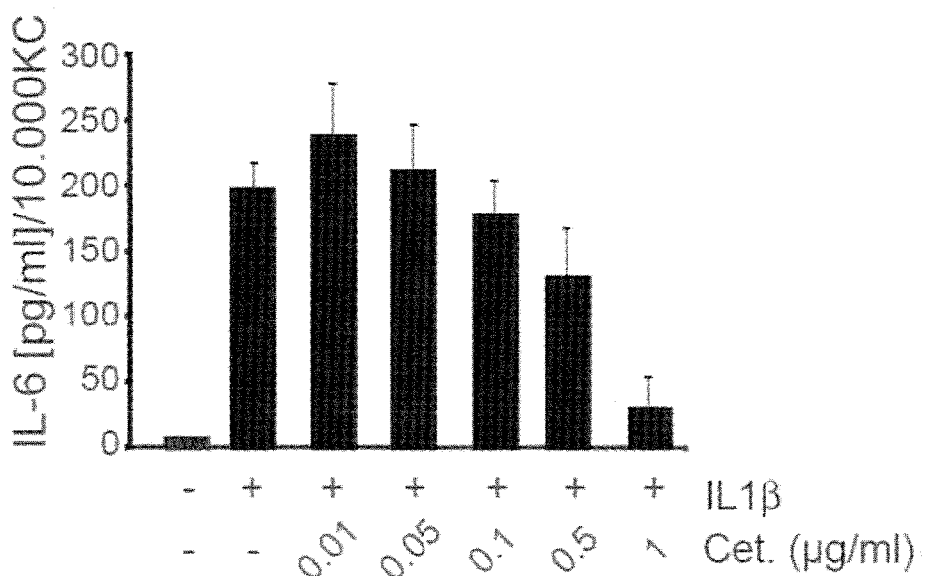
Figure 9:
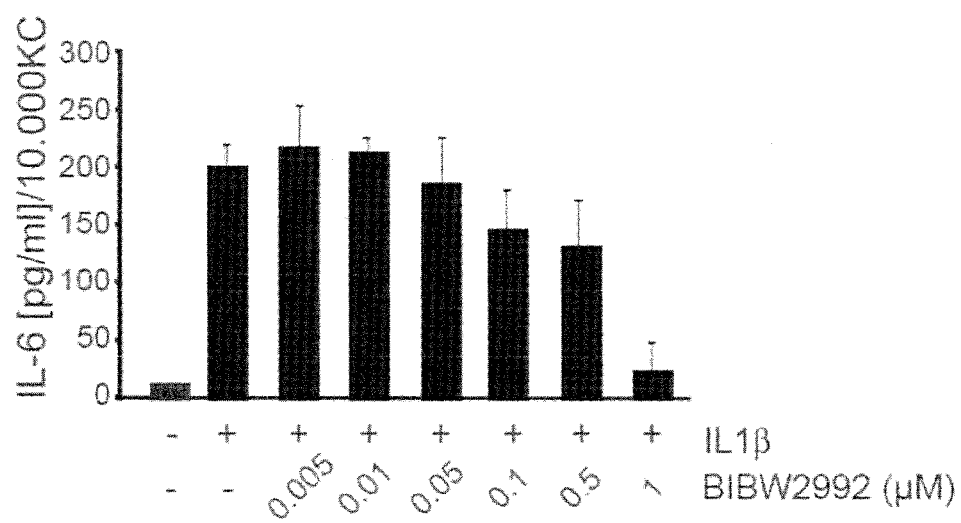
Figure 9:
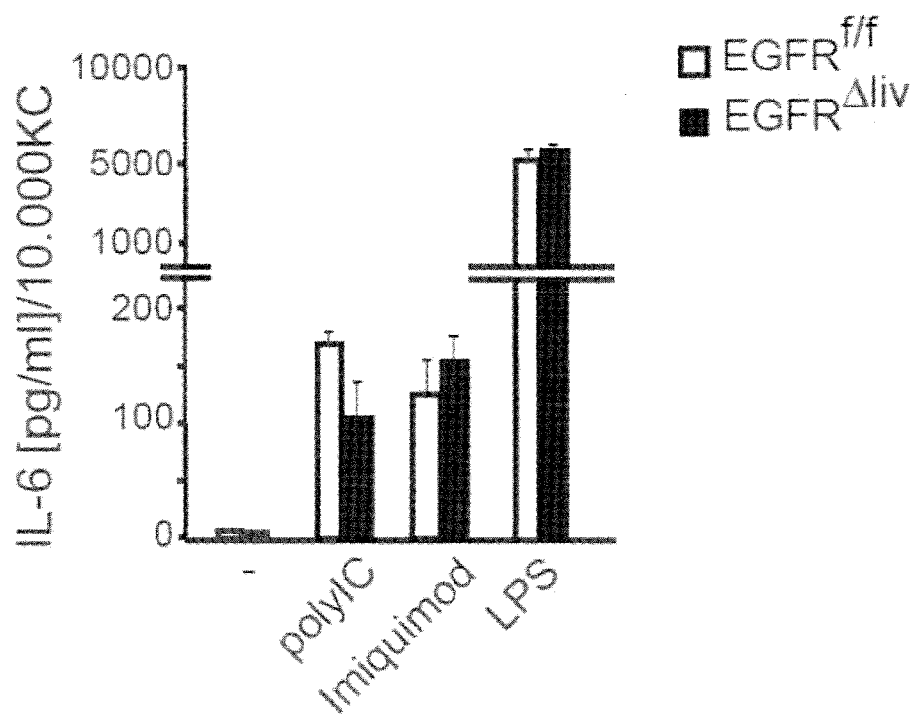

FIG. 9: IL-6 production by Kupffer cells after various stimuli and inhibitor treatments. (A-C) ELISA quantifying IL-1β-induced (10 ng/ml) IL-6 secretion by isolated Kupffer cells after preincubation with increasing amounts of the EGFR inhibitors cetuximab (A) or BIBW2992 (B). (C) IL-6 secretion by isolated Kupffer cells following stimulation with polyIC (20 µg/ml), imiquimod (12 µg/ml) and LPS (10 ng/ml). —=unstimulated.

Figure 10:
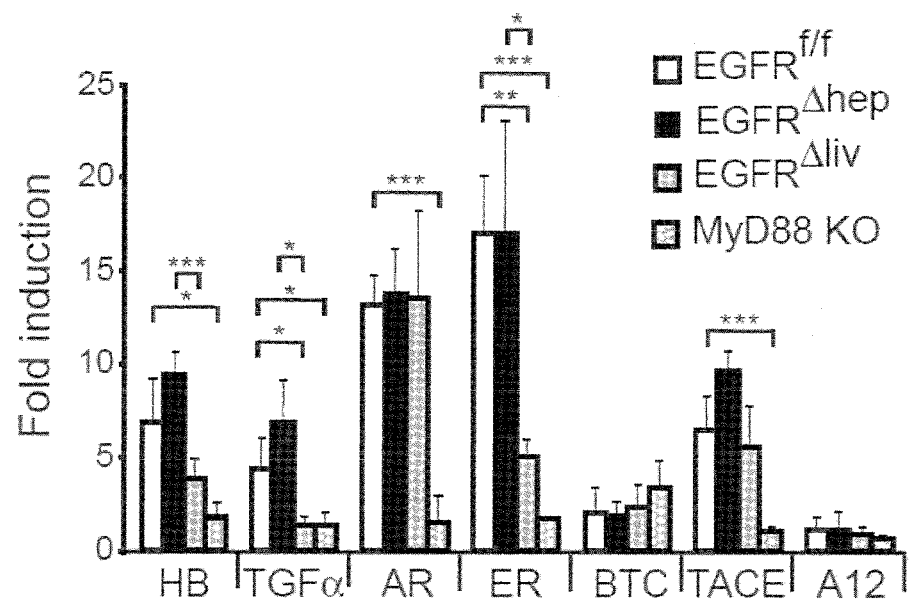
Figure 10:
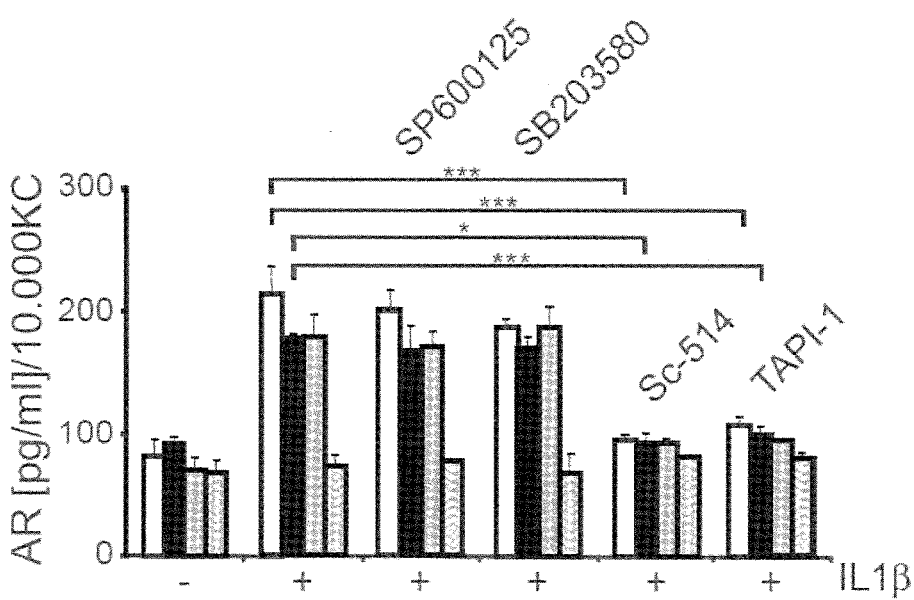
Figure 10:
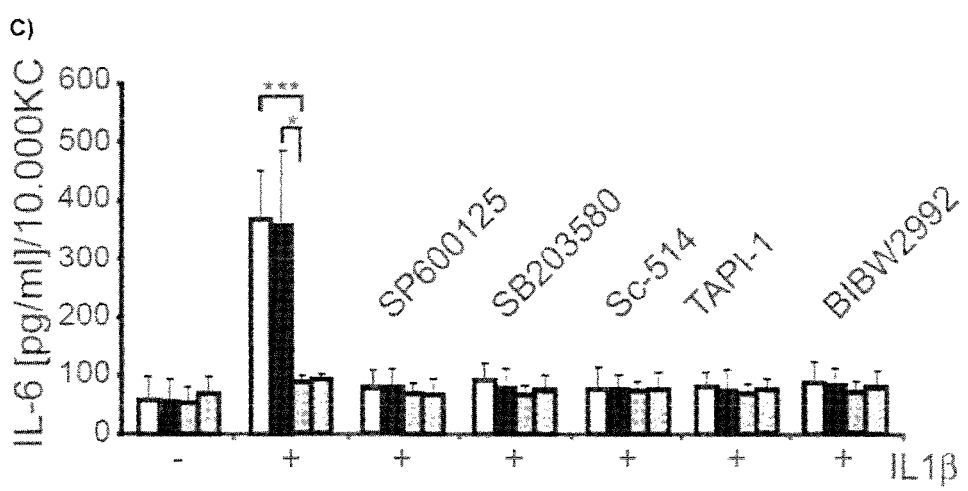
Figure 10:
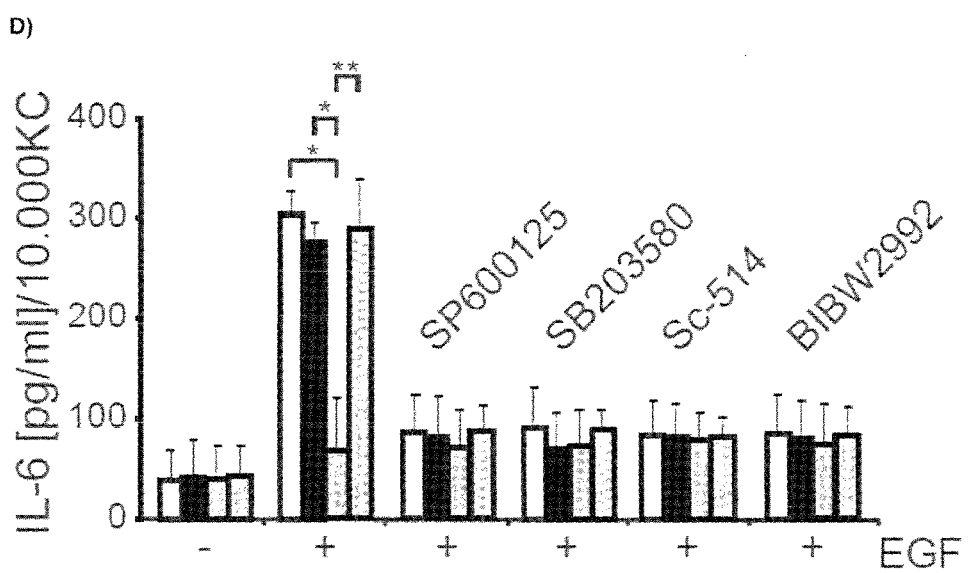
Figure 10:
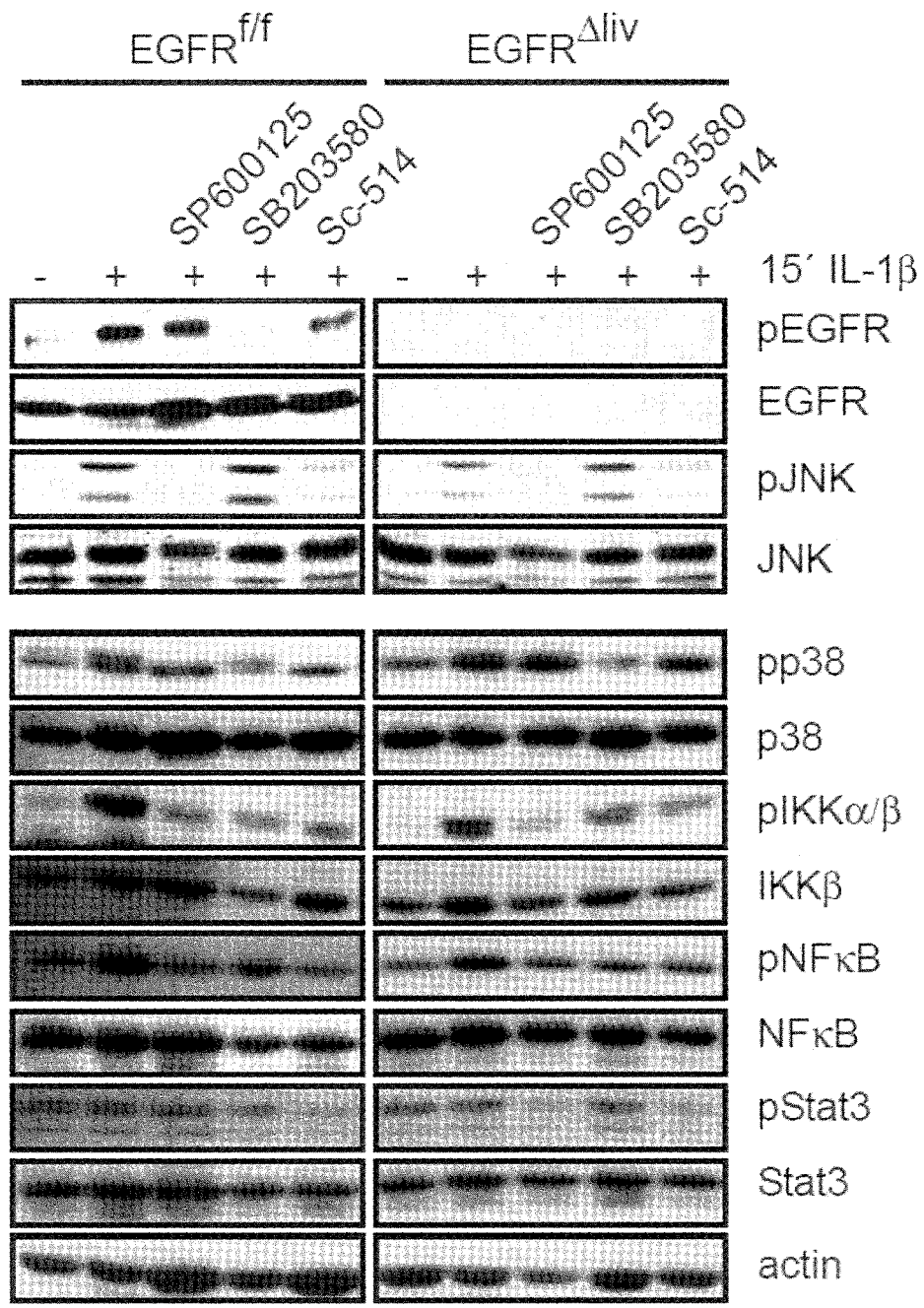
Figure 10:
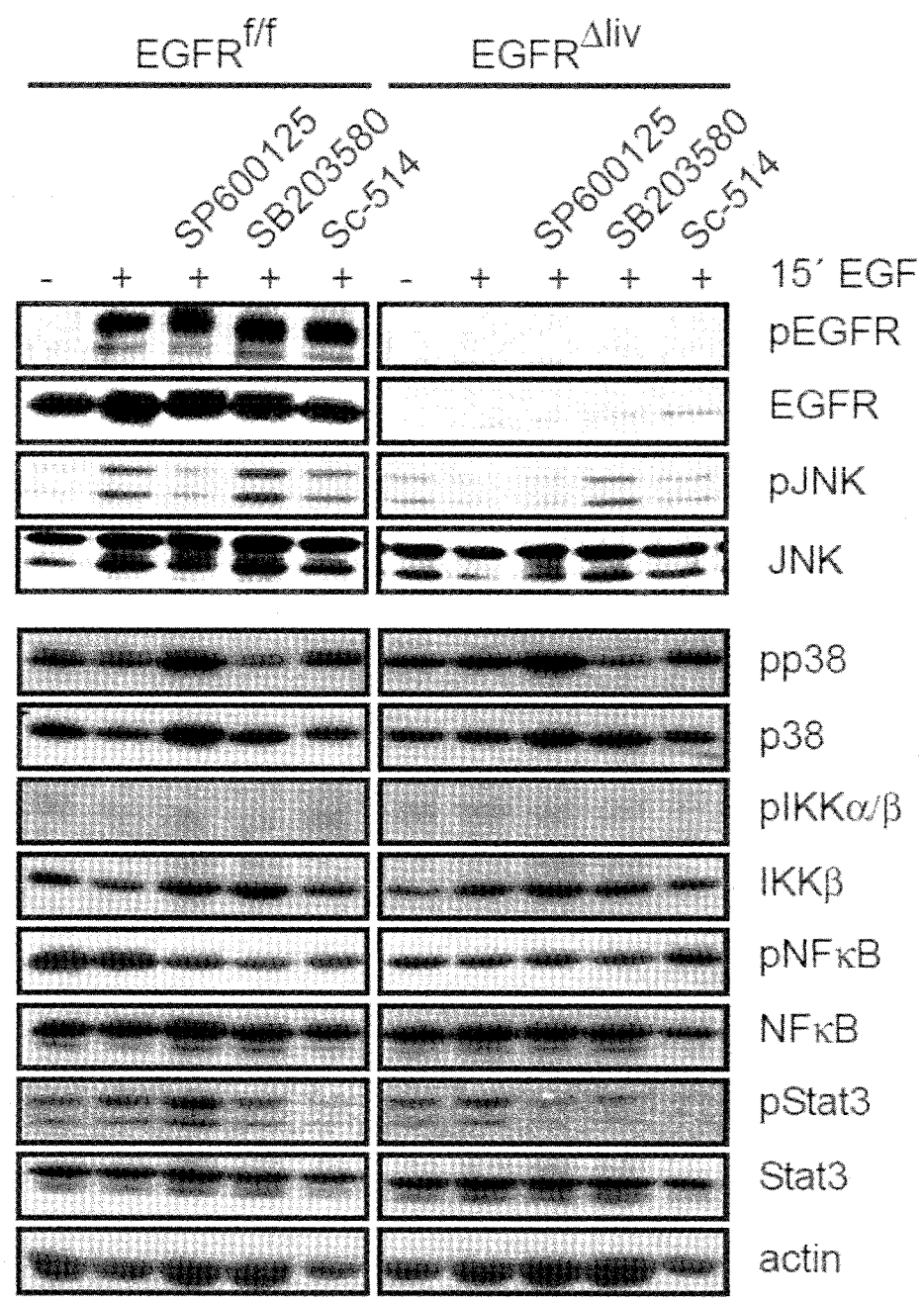

FIG. 10: Mechanism of EGFR-dependent IL-6 production. (A) qRT-PCR showing expression of HB-EGF (HB), TGFα, AR, ER, BTC, ADAM17/TACE, and ADAM12 (A12) in Kupffer cells after IL-1β stimulation in vitro. (B) AR release into the supernatant of cultured Kupffer cells 24 hours after IL-1β stimulation in the presence of JNK (SP600125), p38 (SB203580), IKK2 (Sc-514) and TACE (TAPI-1) inhibitors. (C-D) IL-6 release by cultured Kupffer cells 24 hours after incubation with IL-1β (C) or EGF (D) in the presence of JNK (SP600125), p38 (SB203580), IKK2 (Sc-514), TACE (TAPI-1) or EGFR (BIBW2992) inhibitors. (E-F) Representative Western Blot showing activation of the indicated proteins after 15 minutes stimulation with IL-1β (E) or EGF (F) in the presence of the respective inhibitors. Note: Each lane contains proteins isolated from pooling Kupffer cells of 3 different livers. Because the amount of proteins obtained from Kupffer cells from 3 pooled livers was not sufficient to perform Western blot analysis for all indicated proteins and treatments, 2 different isolates and Western blots for each series of treatment EGF+inhibitors and IL-1β+inhibitors) had to be performed. Blot 1: IL-1β stimulated EGFR$^{f/f}$ and EGFR$^{\Delta liv}$+inhibitors and expression of EGFR and JNK. Blot 2: IL-1β stimulated EGFR$^{f/f}$ and EGFR$^{\Delta liv}$+inhibitors and expression of p38, IKK, NF-kB, Stat3. Blot 3: EGF stimulated EGFR$^{f/f}$ and EGFR$^{\Delta liv}$+inhibitors and expression of EGFR and JNK. Blot 4: EGF stimulated EGFR and EGFR$^{\Delta liv}$+inhibitors and expression of p38, IKK, NF-kB, Stat3. The results were confirmed in a second set of isolates and Westerns. (A-D) Data represent mean±s.d. Student's t-test for independent samples and unequal variances was used to assess statistical significance ($*p<0.05$, $p<0.01$, $*p<0.001$).

Figure 11:
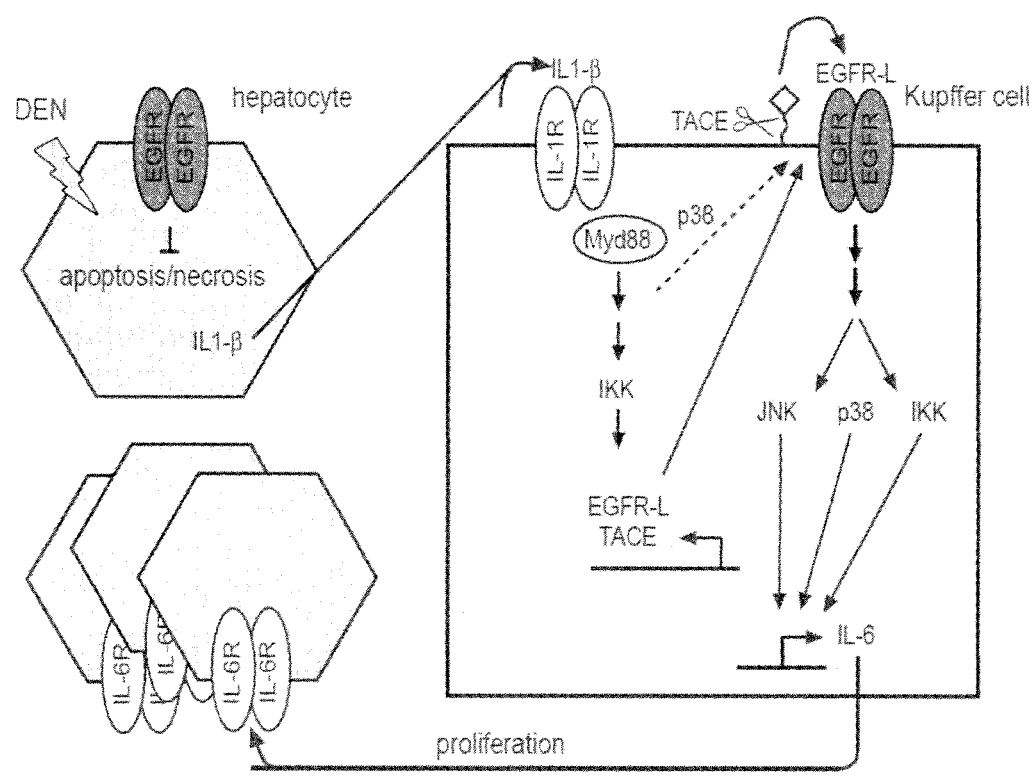

FIG. 11: IL-1β-induced IL-6 production requires EGFR ligand cleavage and functional JNK-, p38-, and IKK2-signaling in Kupffer cells. Model of EGFR signaling in hepatocytes and Kupffer cells during HCC formation.

Figure 12:
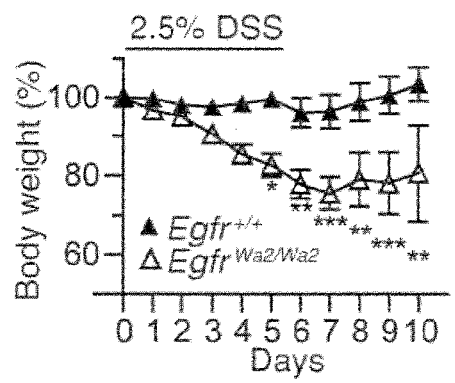
Figure 12:
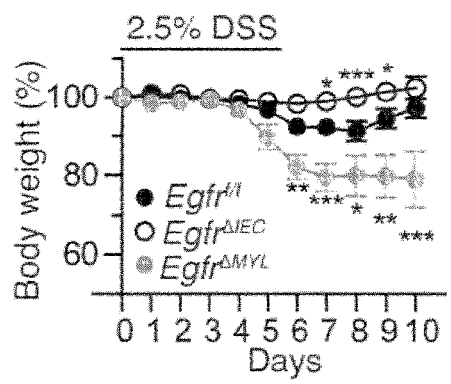
Figure 12:
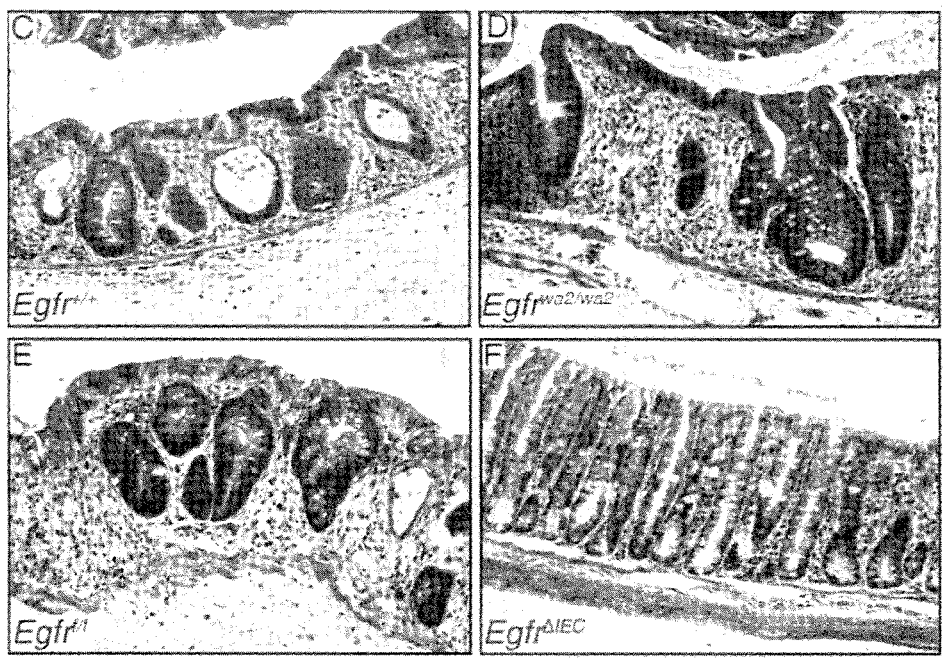
Figure 12:
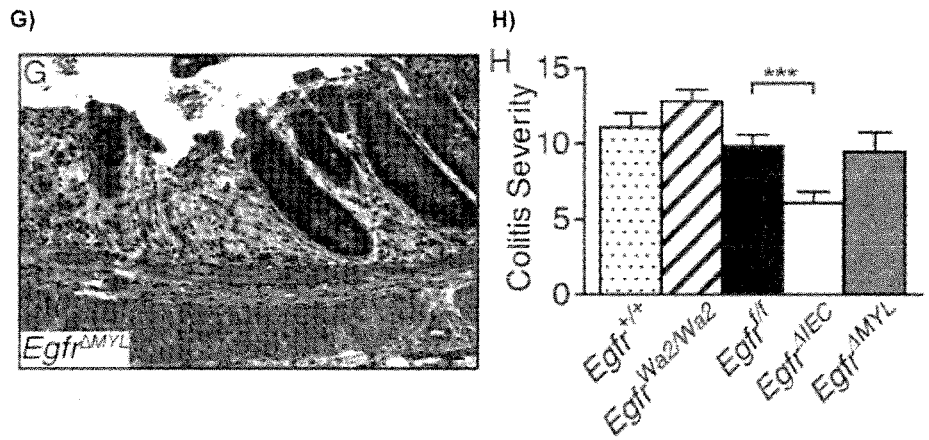

FIG. 12: Deletion of EGFR in stromal cells tends to exacerbate colitis, while its deletion in IEC's is partially protective. Comparison of body weight during DSS treatment (A) WT and waved mice, N=6. (B) Egfr$^{f/f}$, Egfr$^{ΔIEC}$ and Egfr$^{ΔMYL}$ conditional KO mice N≥8. (C-G) Representative histological sections of the DSS treated mice at D10, scale in image represents 20 μm. (H) Histological assessment of colitis severity. Data are mean±SEM ($$ $p<0.01$, $*$ $p<0.001$).

Figure 13:
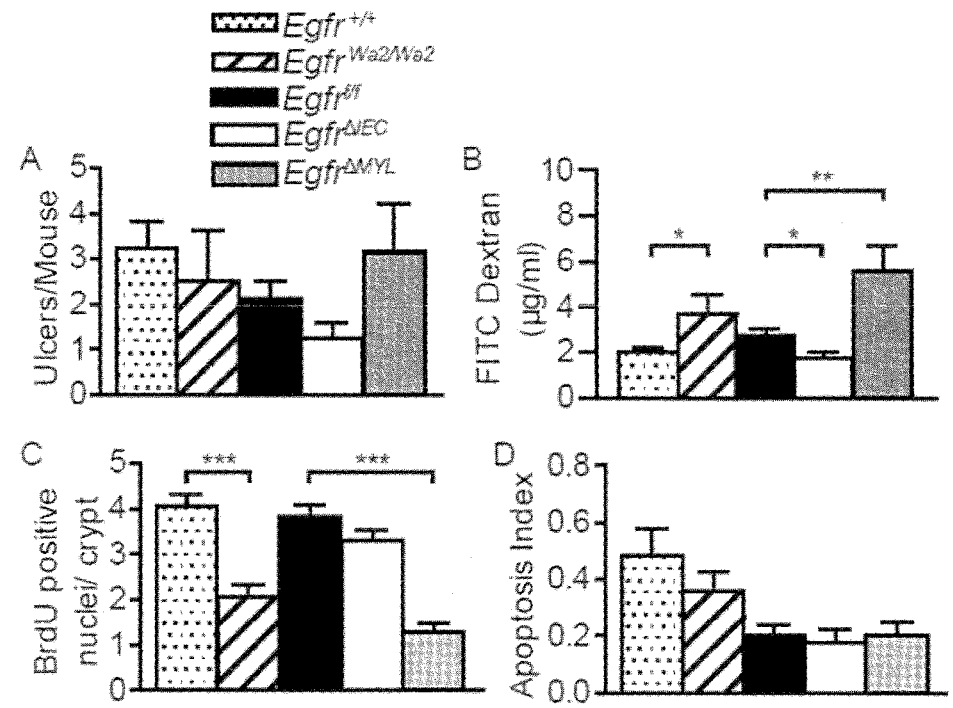

FIG. 13: EGFR expression on myeloid cells is protective during colitis. (A) Histological assessment of ulceration at D10 in DSS treated mice. (B) Measurement of FITC-dextran concentration in serum. Quantifications of BrdU incorporation (C) and cleaved Caspase 3 positive cells (D) in crypts of DSS treated mice. Data are mean±SEM N≥5, $$ $p<0.01$, $*$ $p<0.001$.

Figure 14:
Figure 14:
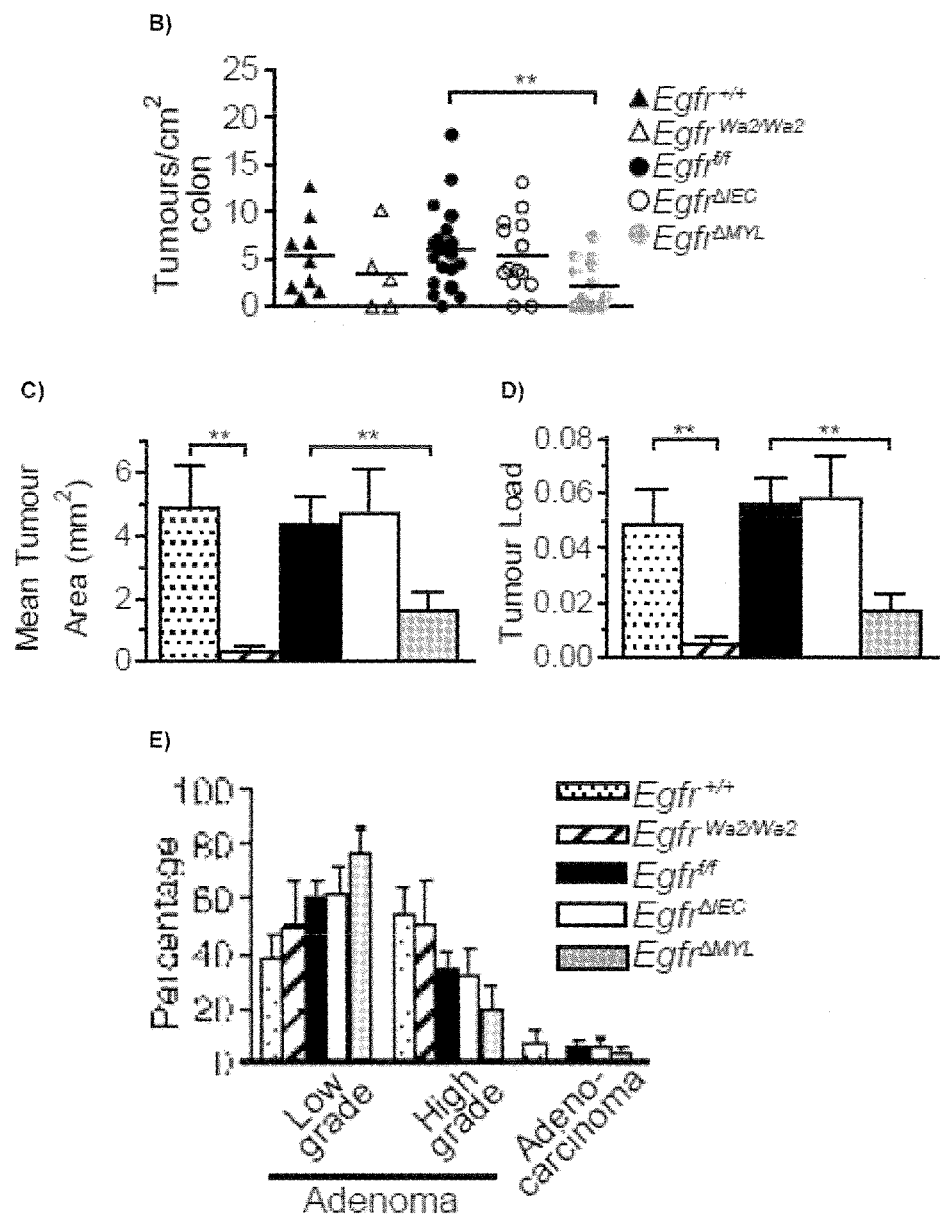
Figure 14:
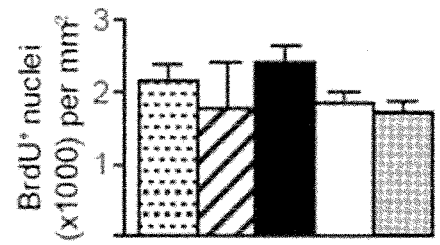
Figure 14:
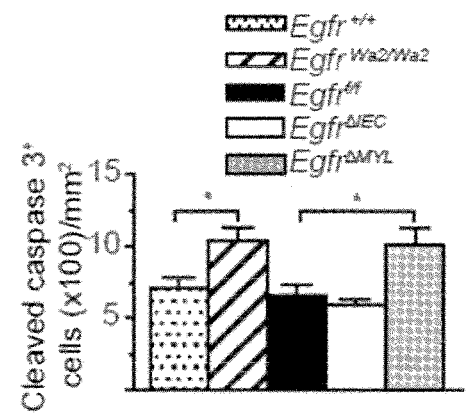

FIG. 14: EGFR conditional deletion in myeloid lineage reduces tumor formation and tumor growth. (A) Representative haematoxylin and eosin stained images of "swiss rolls", arrowheads depict localization of tumors within colon, scale in image represents 1 mm. (B) Tumor multiplicity in mice, a ratio of tumor number and colon area. (C) Average size of tumors. (D) Tumor load, calculated as ratio of total tumor area and colon area, (E) Microscopic gradation of tumors. (F) Quantification of BrdU incorporation and (G) cleaved caspase 3$^+$ cells in tumors, $*$ $p<0.05$, $**p<0.005$.

Figure 15:
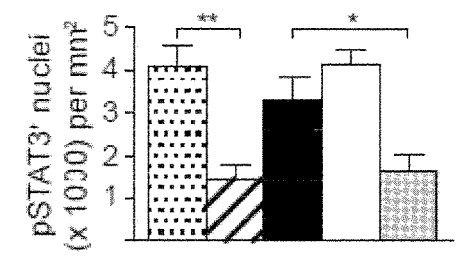
Figure 15:
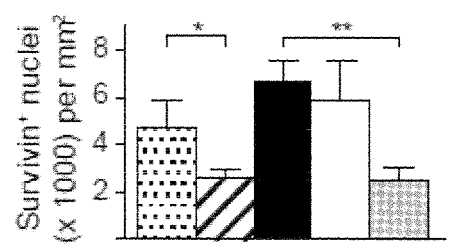
Figure 15:
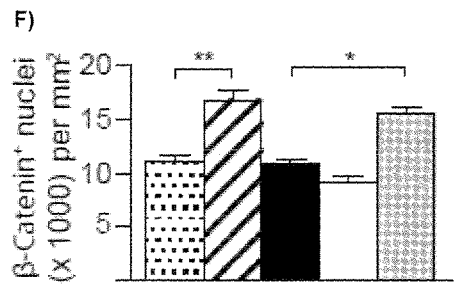
Figure 15:
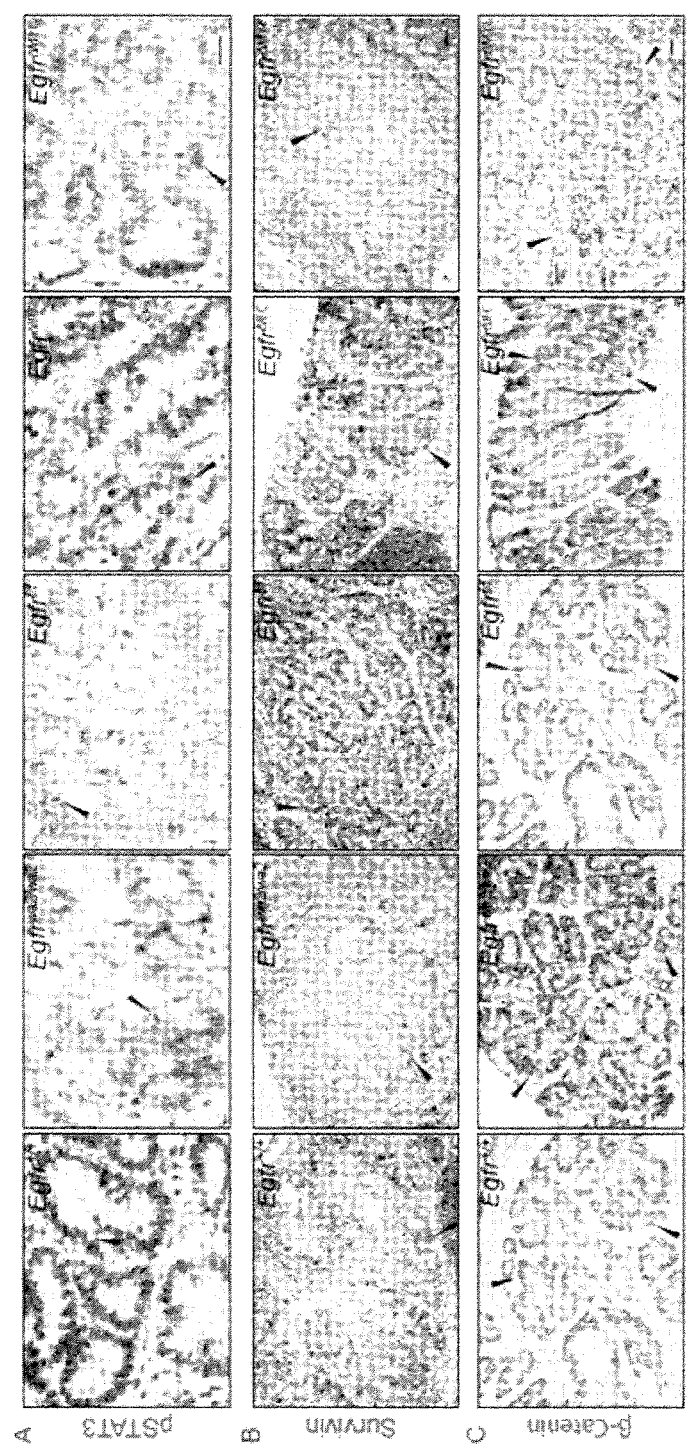

FIG. 15: Tumors in Egfr$^{ΔMYL}$ mice show reduced IL-6 mediated STAT3 signaling. (A) Immunohistochemistry staining reveals decreased nuclear pSTAT3 localization, arrowheads depict pSTAT3$^+$ nuclei. (B) Immunohistochemistry showing reduced Survivin expression, arrowheads depict Survivin nuclei (C) β-Catenin immunohisothemistry showing its increased nuclear localization, arrowheads depict β-Catenin+ nuclei in tumor sections of Egfr$^{wa2/wa2}$ and Egfr$^{ΔMYL}$ mice. (D) Quantification of pSTAT3 positive nuclei (E) quantification of Survivin positive nuclei and (F) quantification of 1-Catenin positive nuclei. Data are mean±SEM (n=3; $*p<0.05$, $**$ $p<0.01$). Scale in images represents 20 μm.

Figure 16:
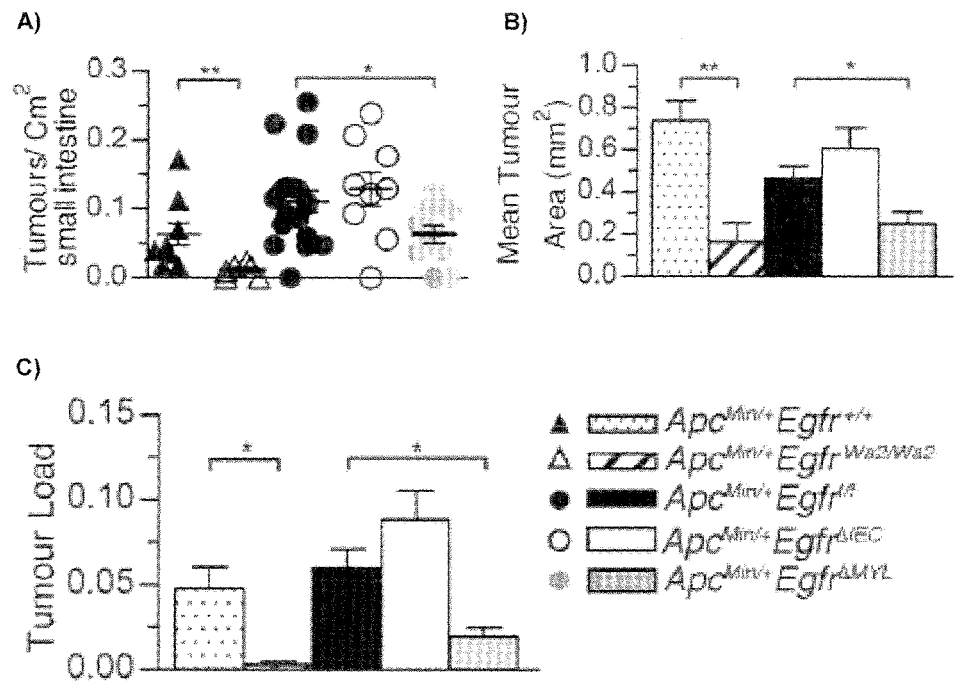

FIG. 16: EGFR conditional deletion in non-epithelial cells reduces tumor growth in ApcMin/+ mice. Analysis of tumor incidence in mice, (A) tumor multiplicity, (B) average size of tumors, (C) tumor load, data are mean±SEM, $*=p<0.05$, $**=p<0.01$.

Figure 17:
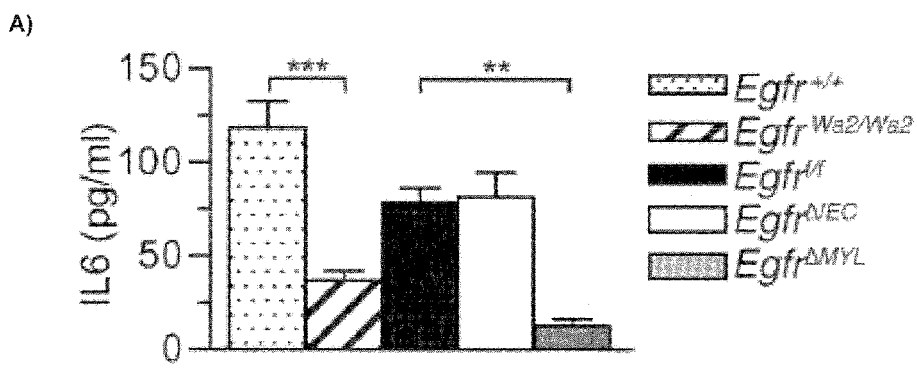
Figure 17:
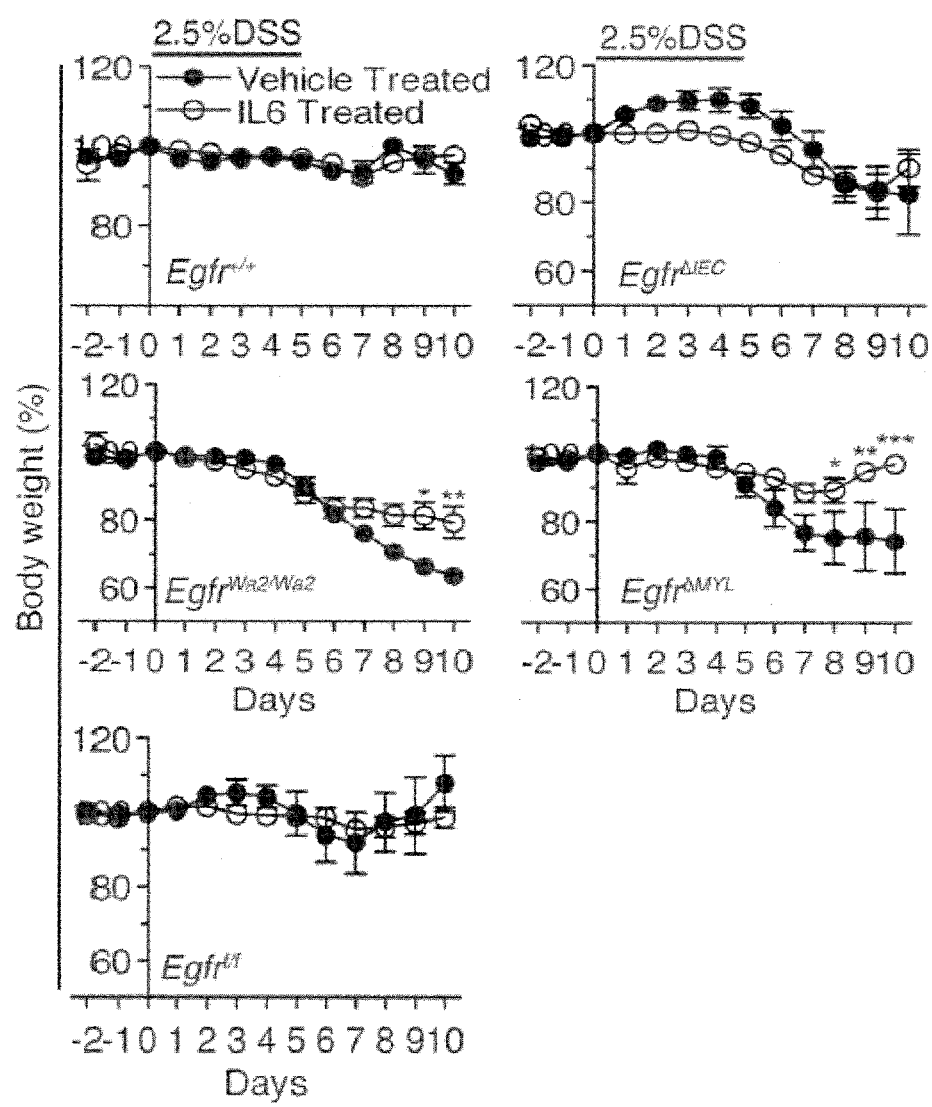
Figure 17:
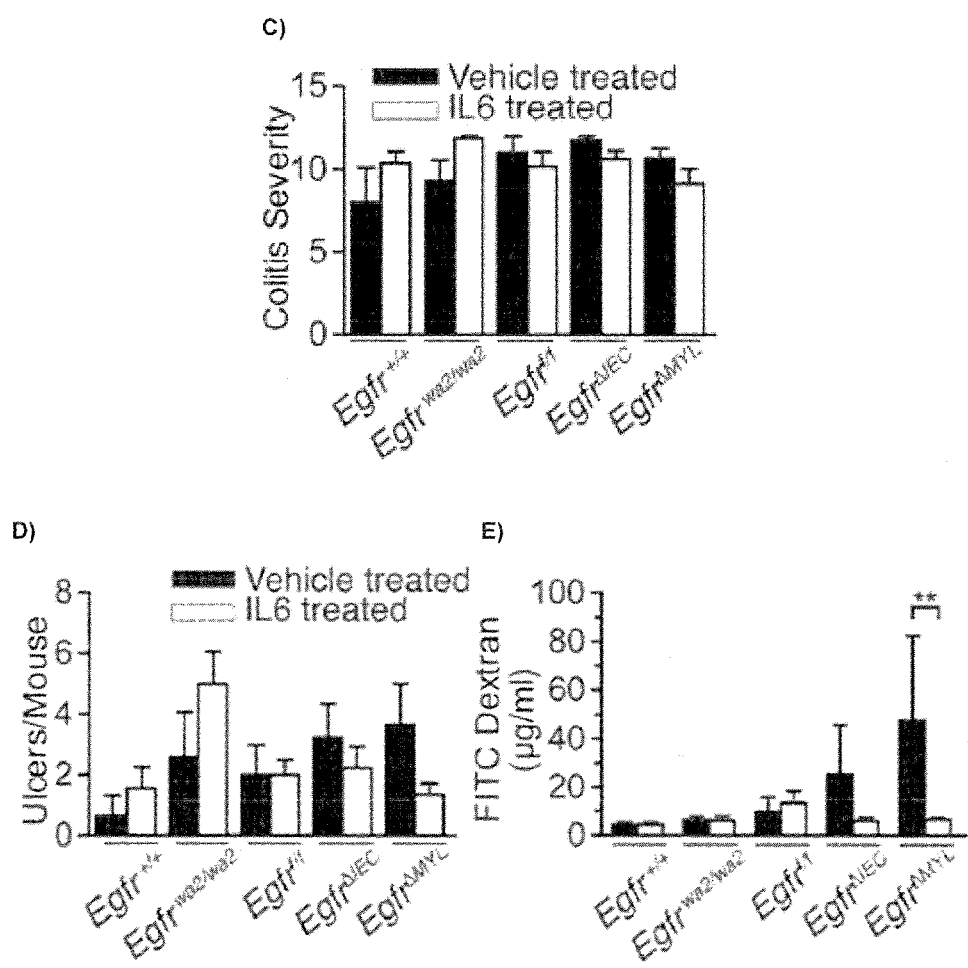

FIG. 17: IL-6 administration during DSS treatment protects against colitis induced weight loss and loss of barrier function. (A) Systemic levels of IL6 measured in serum of mice treated with 2.5% DSS at day 7. (B) Body weights of mice during DSS treatment, mice were administered IL6 orally. (C) Histological assessment of colitis severity and (D) ulceration of DSS treated mice, measurement of FITC-dextran concentration in serum (E) post colitis regimen. ($*$ $p<0.05$, $$ $p<0.01$, $*$ $p<0.001$).

Figure 18:
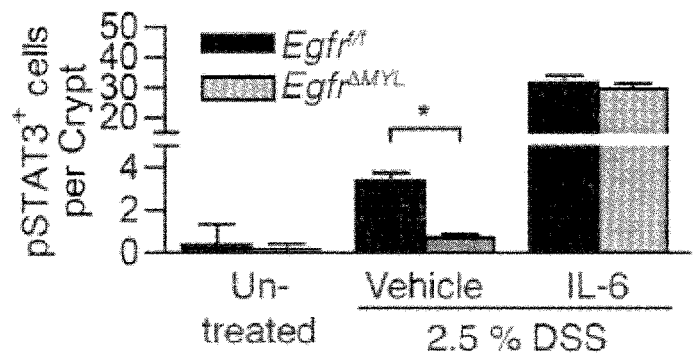

FIG. 18: IL-6 administration restores proliferation and STAT3 signaling in Egfr$^{ΔMYL}$ mice during colitis. (A) Quantification of BrdU incorporation and (B) cleaved Caspase 3 positive nuclei in crypts of mice administered IL-6 during colitis regimen. (C) Representative images of immunohistological staining for pSTAT3 on colon sections, arrowheads depict pSTAT3 positive nuclei (D) quantification of pSTAT3 positive nuclei per crypt ($p<0.0001$), scale in images represents 20 μm.

Figure 19:
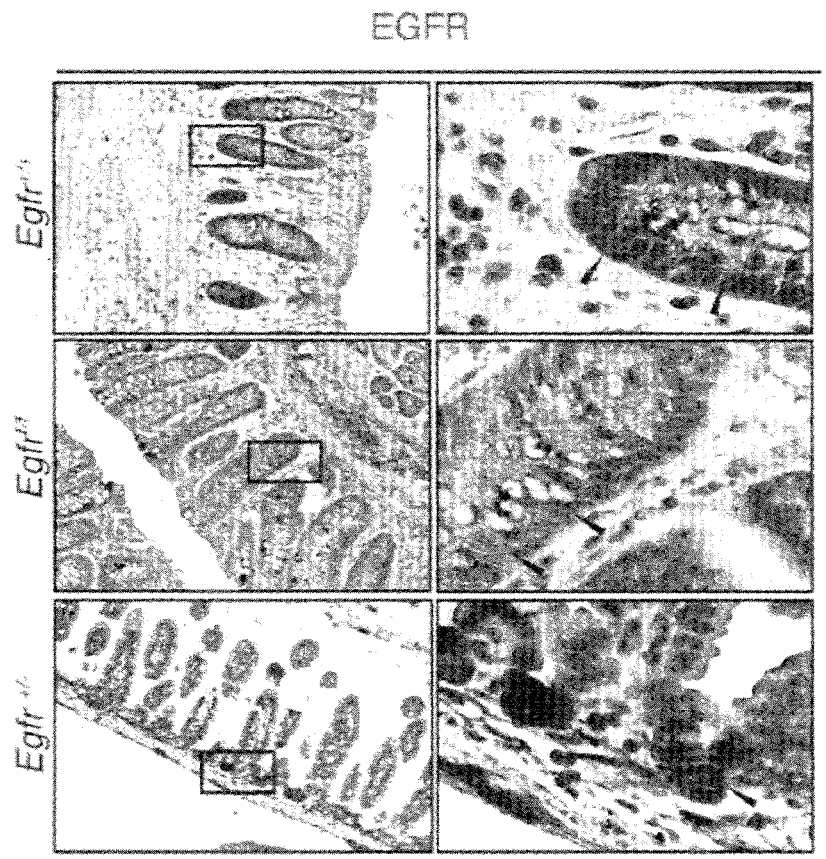
Figure 19:
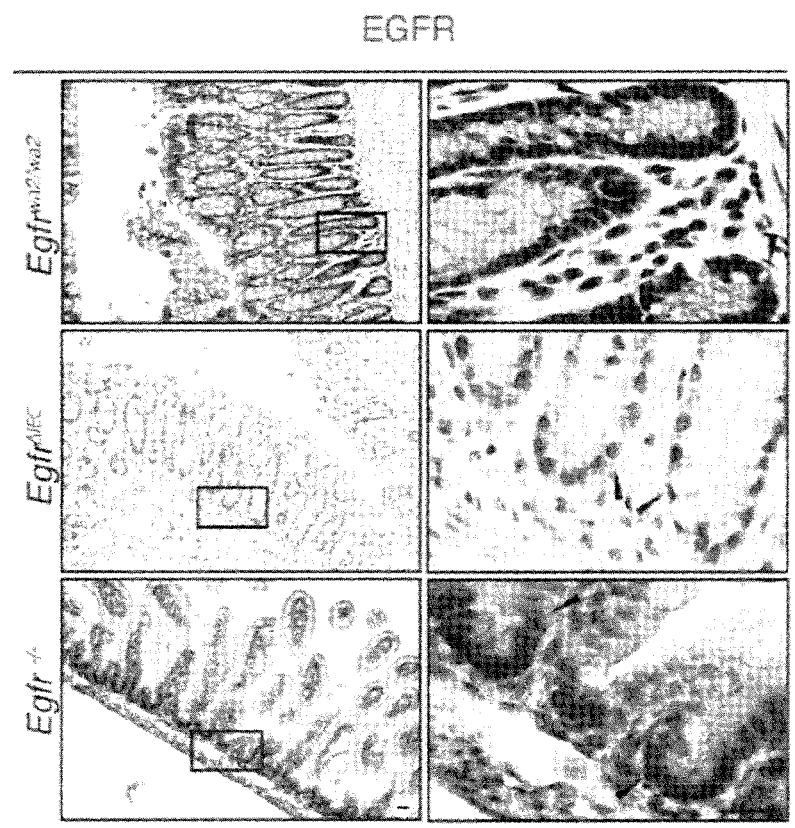

FIG. 19: Successful deletion of egfr in intestinal epithelium. EGFR Immunostaining on histological sections of DSS treated mouse colons, arrowheads depict IECs. Arrowheads depict crypts in EGFR Immunohistological staining on histological sections of small intestine in EGFR heterozygous wild type and total KO littermate. Scale in images represents 20 μm.

Figure 20:
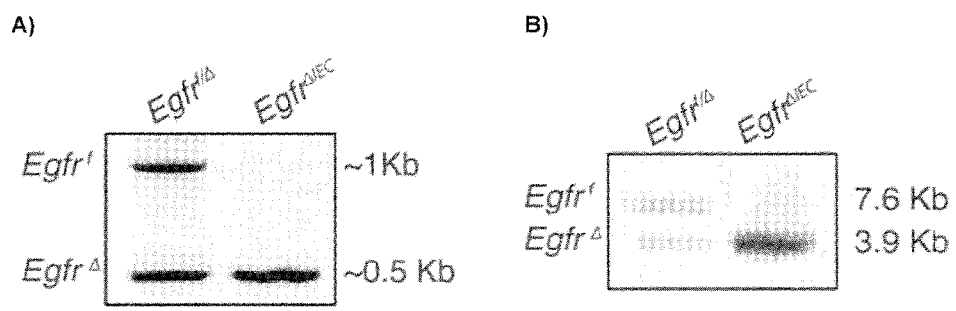
Figure 20:
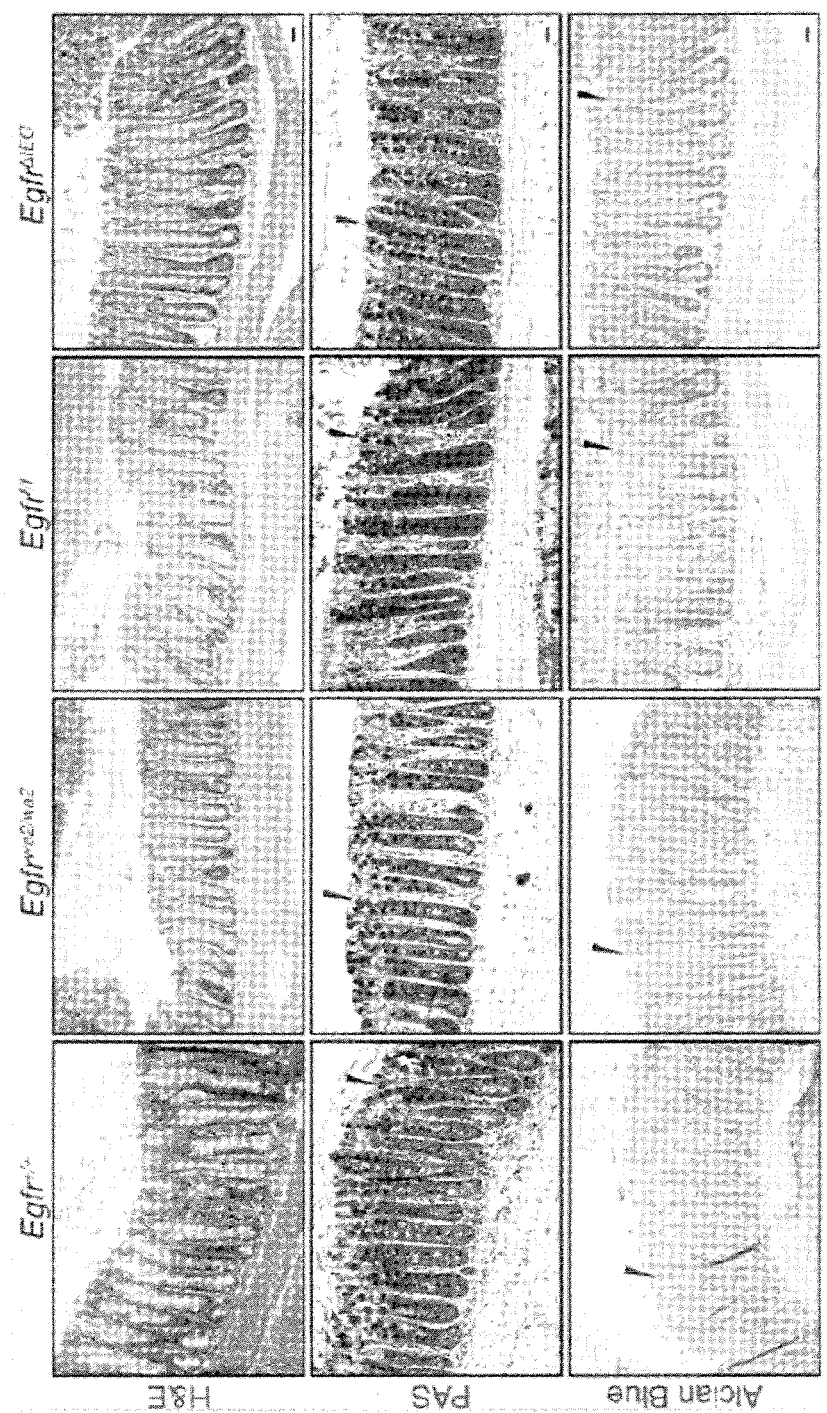
Figure 20:
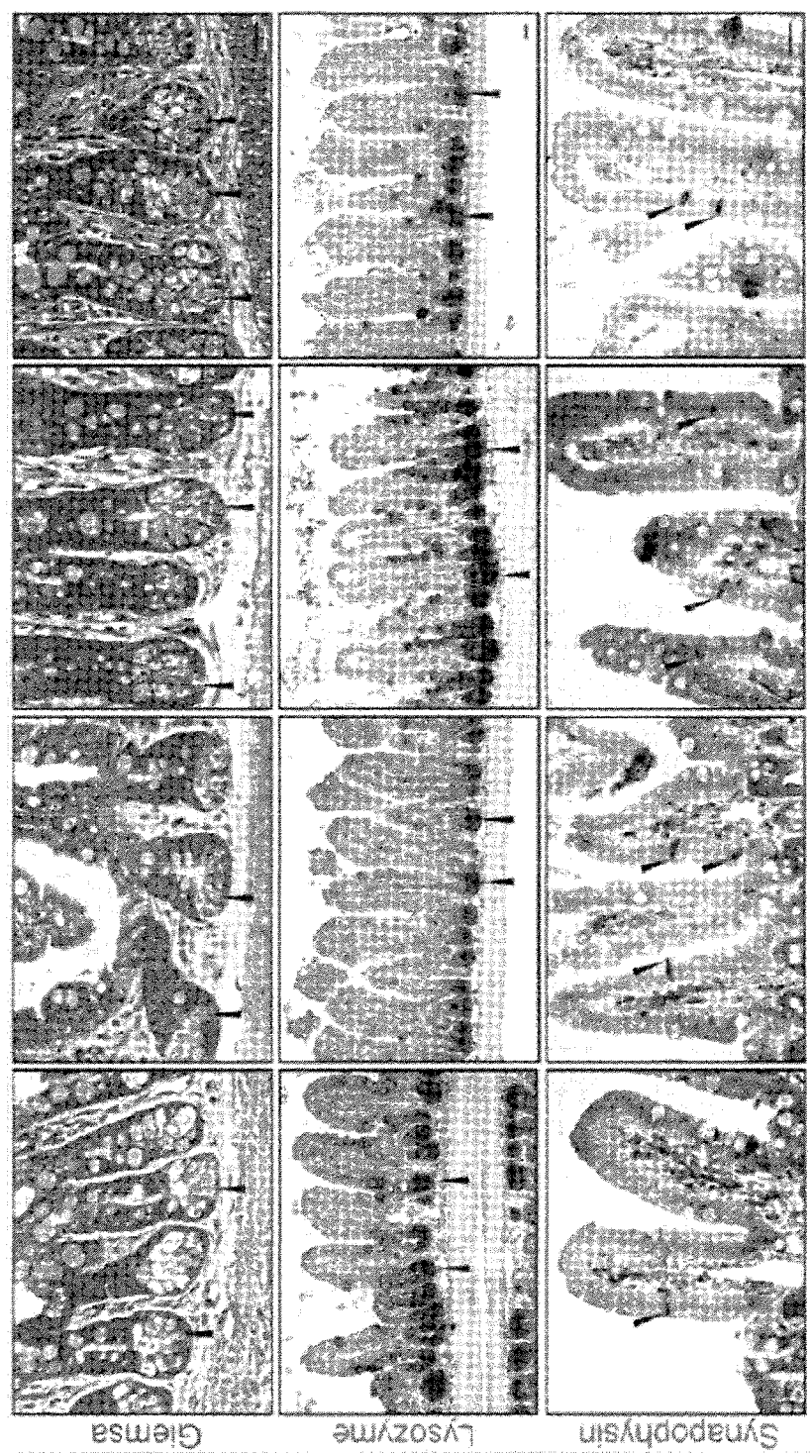

FIG. 20: Loss of EGFR in intestinal epithelium does not perturb intestinal morphology. Confirmation of CRE mediated recombination of "floxed" egfr allele by (A) PCR and (B) Southern blot. (C) H&E, PAS and Alcian blue staining on histological sections of colons showing gross morphology, arrowheads show goblet cells. (D) Giemsa staining on small intestine, arrowheads show refractive eosinophilic granules of paneth cells and immunohistochemistry for Lysozyme and Synaptophysin, arrowheads demonstrate presence of paneth cells and enteroendocrine cells respectively. Scale in images represents 20 μm.

Figure 21:
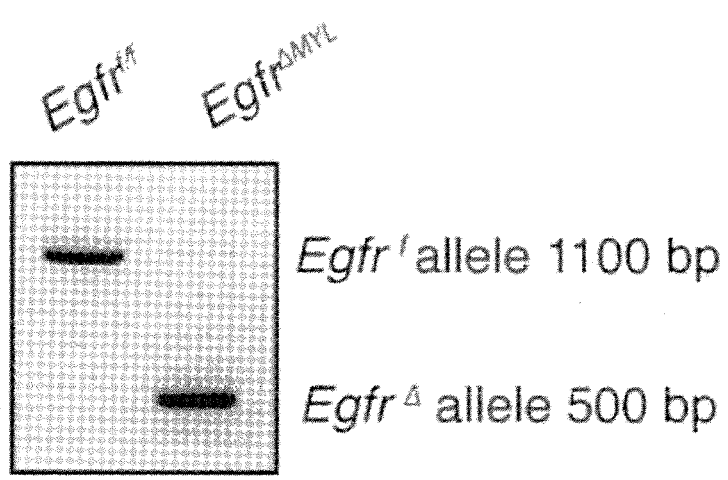
Figure 21:
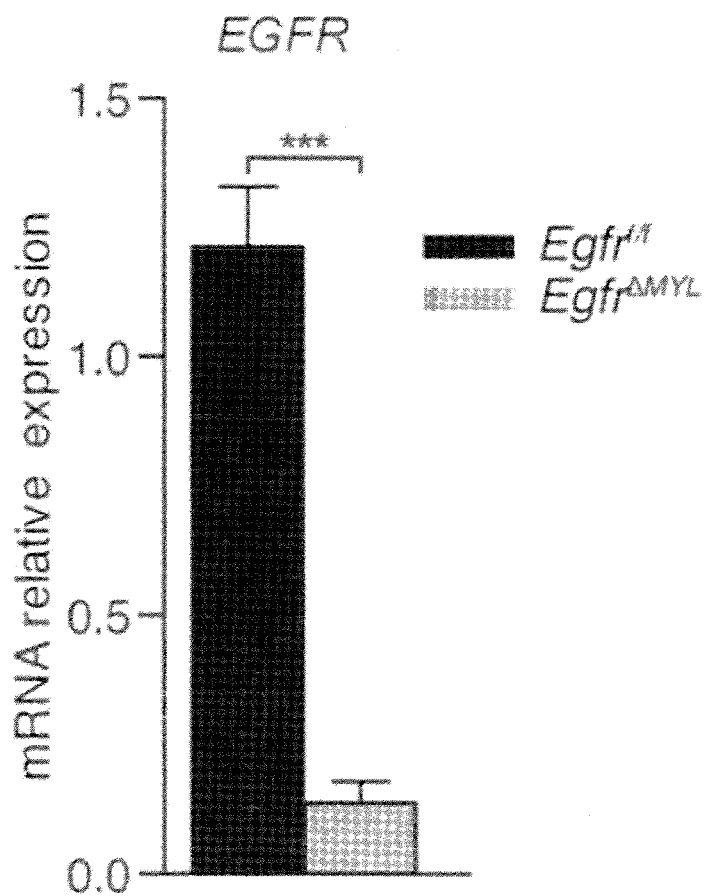
Figure 21:
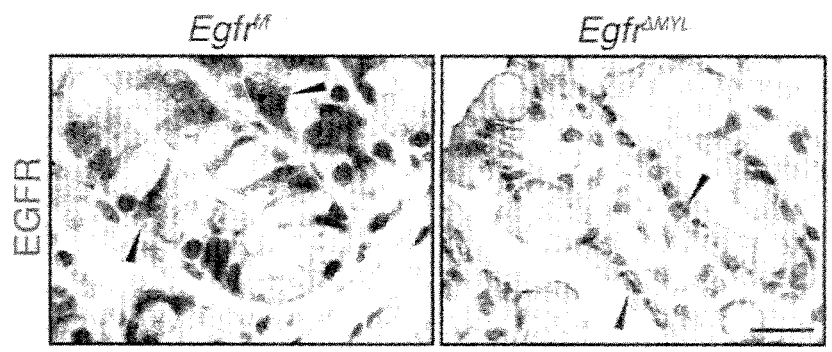
Figure 21:
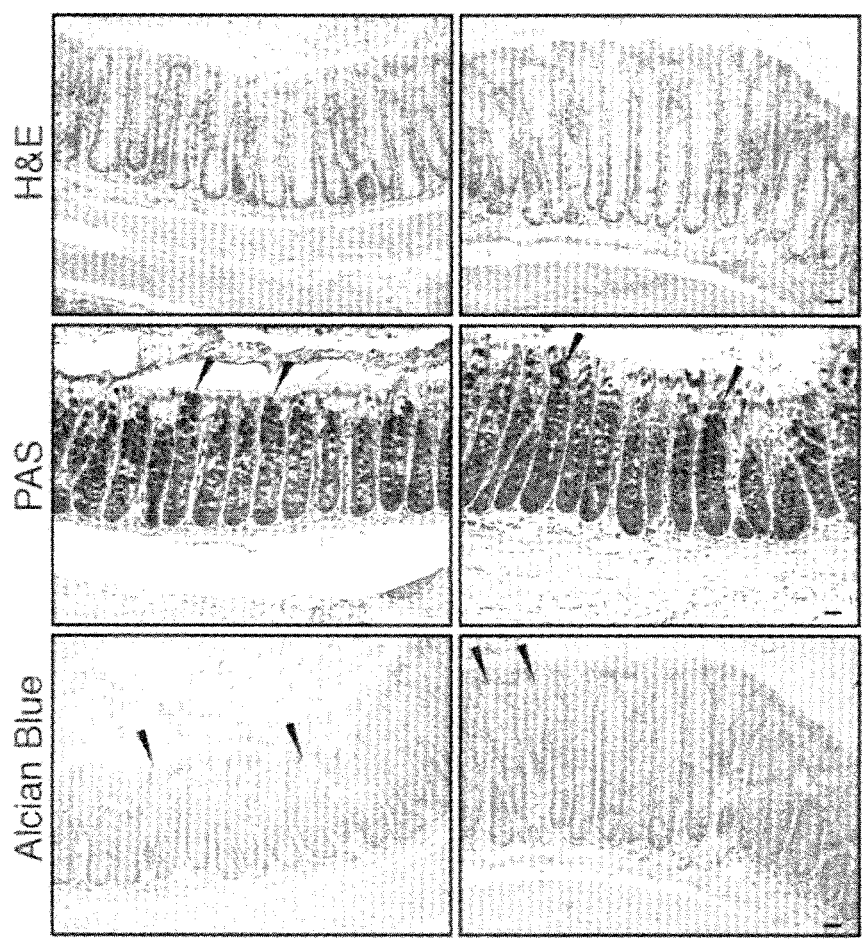
Figure 21:
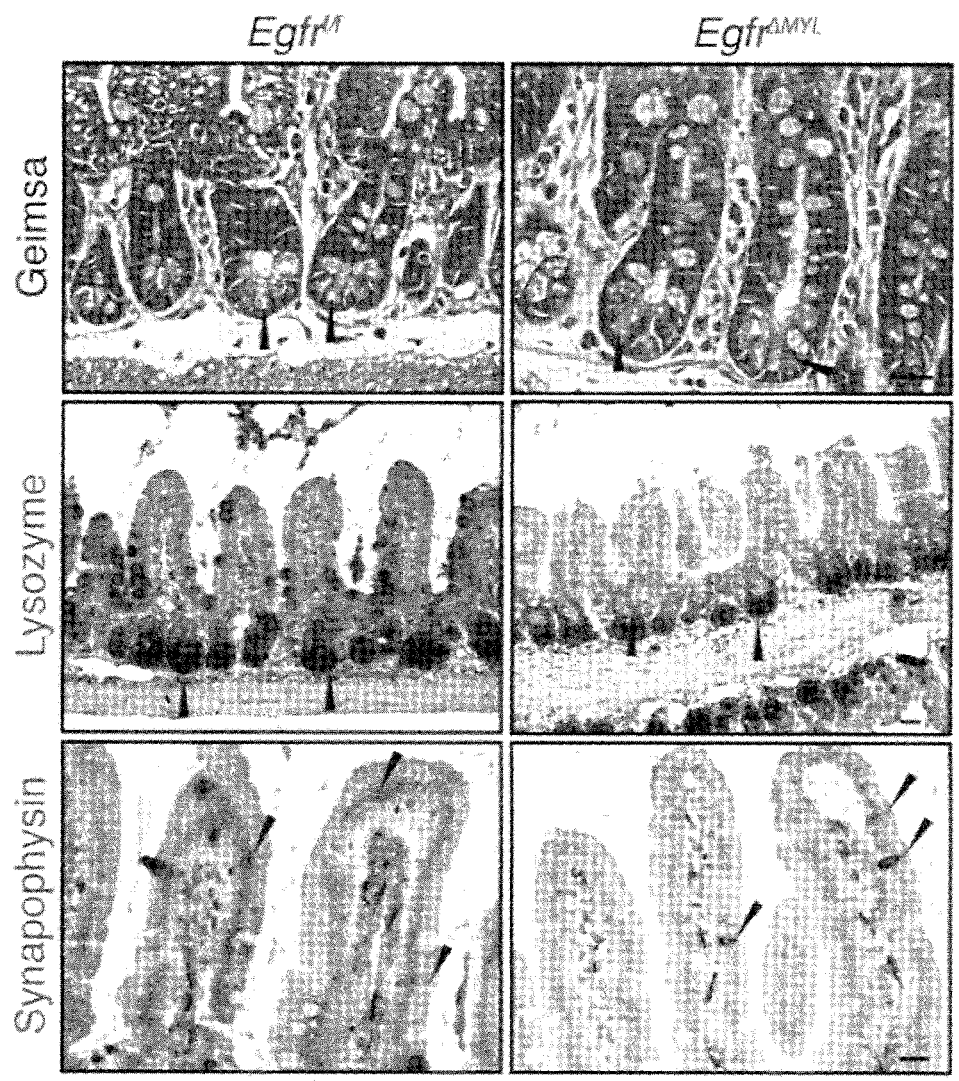

FIG. 21: Mice lacking EGFR in lamina propria cells have no overt gut phenotype. (A) PCR confirmation of egfr deletion in BMDM from Egfr$^{ΔMYL}$ mice, (B) quantification of EGFR expression on RNA from BMDM. (C) Analysis of EGFR expression by immunohistochemistry on DSS treated mouse colon sections, EGFR expression mainly on crypt cells in Egfr$^{ΔMYL}$ mice and absence on lamina propria cells show successful cre mediated deletion of egfr. (D) H&E, PAS and Alcian blue staining on histological sections of colons showing gross morphology, arrowheads show goblet cells. (E) Giemsa staining on small intestine, arrowheads show refractive eosinophilic granules of paneth cells and immunohistochemistry for Lysozyme and Synaptophysin, arrowheads demonstrate presence of paneth cells and enteroendocrine cells respectively, scale in images represents 20 μm.

Figure 22:
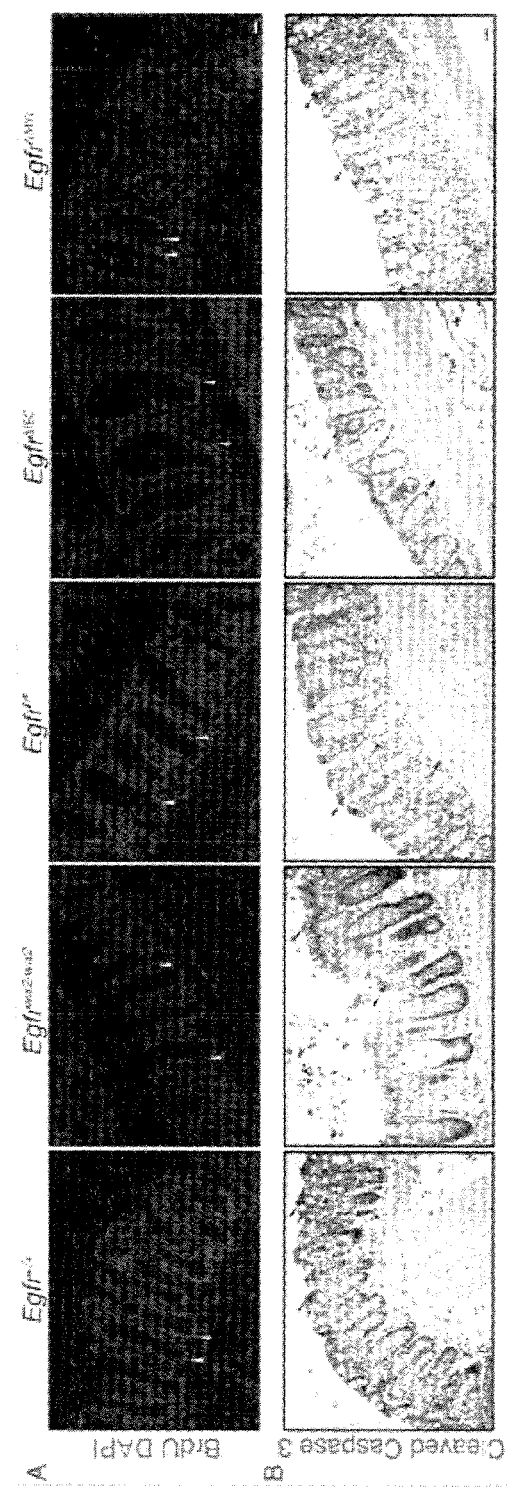
Figure 22:
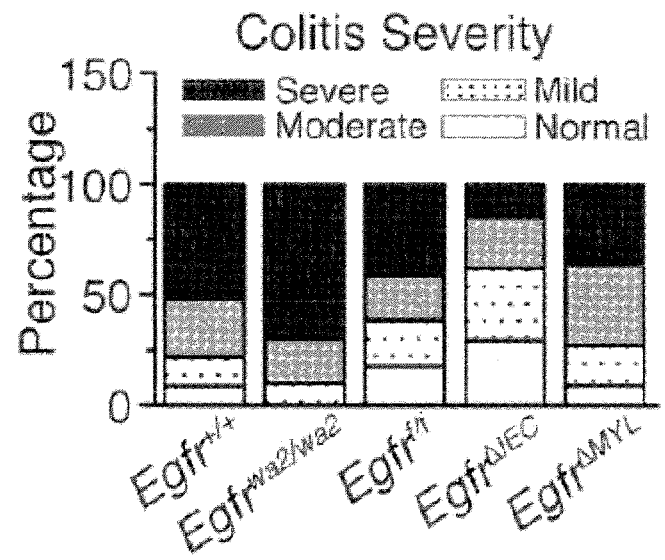

FIG. 22: Loss or reduction in EGFR signaling on myeloid cells leads to epithelial proliferative defects during colitis and increased colitis susceptibility. Representative images of (A) BrdU immunofluoresence staining and (B) cleaved Caspase 3 immunohistological staining on histological sections of DSS treated mice. Scale in images represents 20 μm. (C) Cumulative incidence of colitis severity among the different cohorts. Scale in image represents 20 μm.

Figure 23:
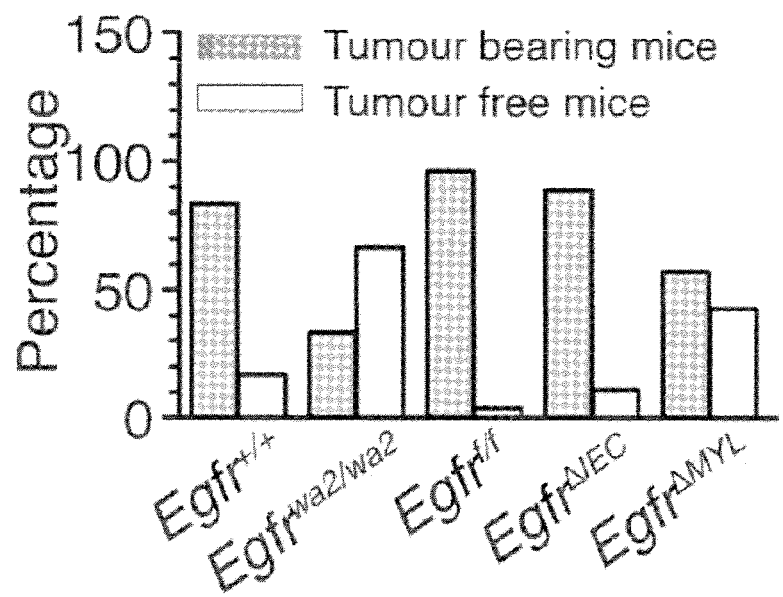
Figure 23:
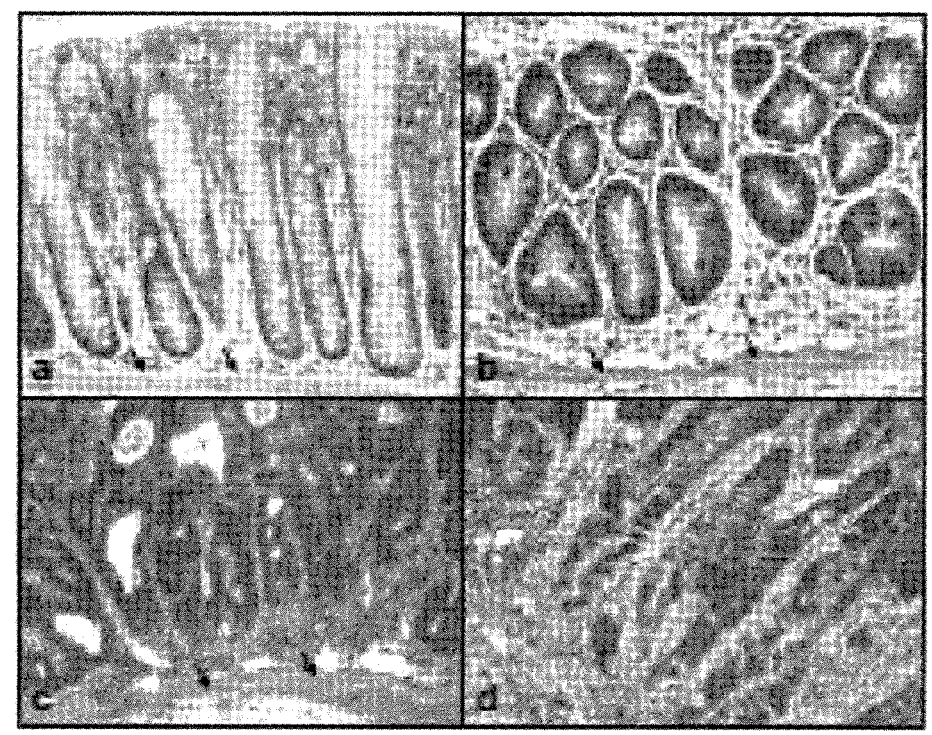

FIG. 23: EGFR expression on myeloid cells is important for colitis associated tumor formation. (A) Tumor formation rate, (B) representative images of tumor gradation, a=normal epithelium, b=low grade adenoma, c=high grade adenoma, d=carcinoma, arrows indicate intact muscularis mucosae.

Figure 24:
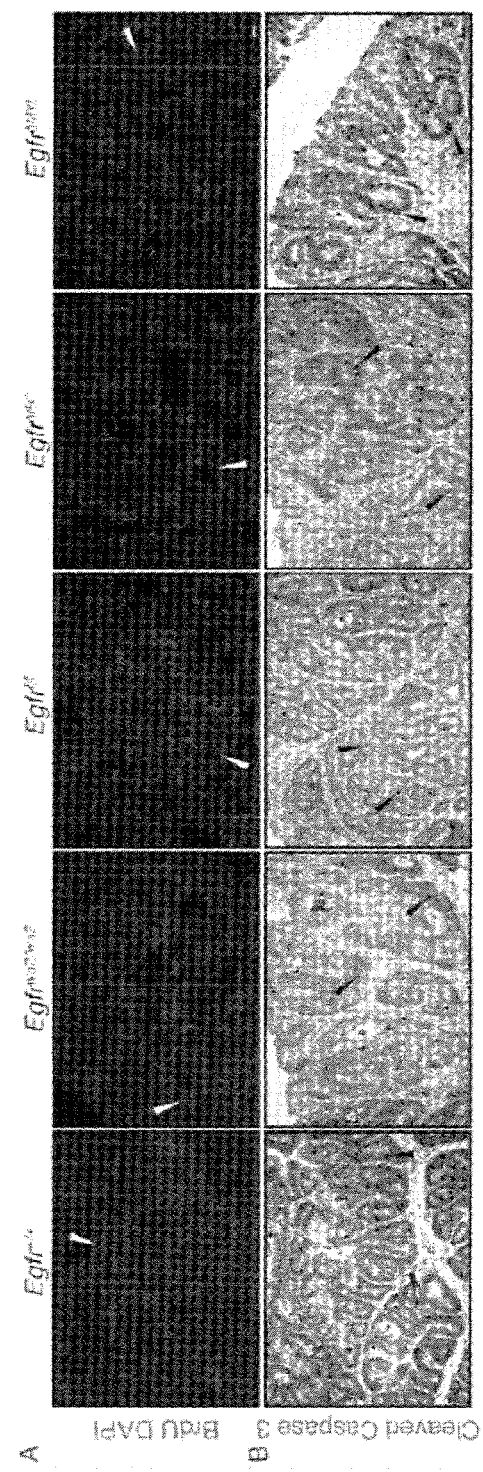

FIG. 24: EGFR expression on myeloid cells prevents apoptosis in tumors. (A) Representative images of BrdU immunofluorescence staining, (B) cleaved Caspase 3 immunohistological staining for apoptosis in histological in tumors of AOM-DSS treated mice, arrowheads depict BrdU+ and cleaved Caspase 3+ nuclei respectively. Scale in images represents 20 μm.

Figure 25:
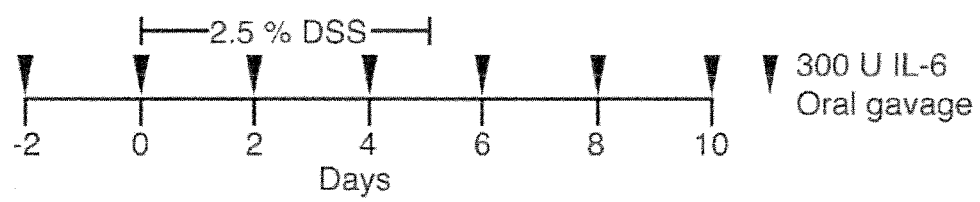
Figure 25:
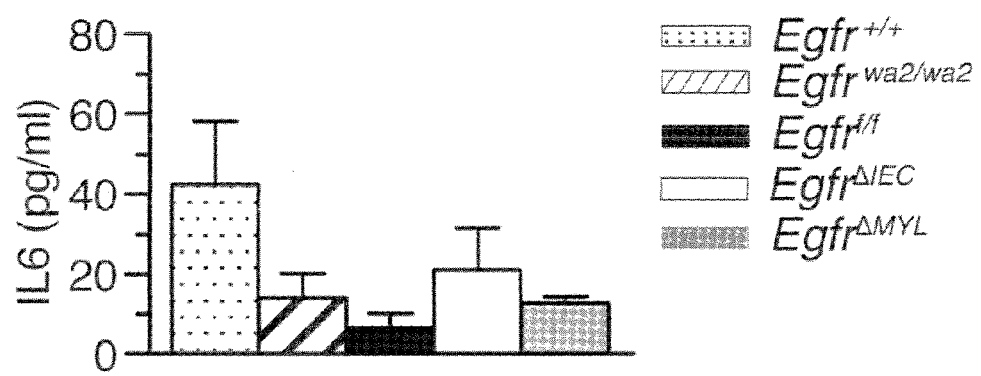

FIG. 25: Administration of IL6 during DSS treatment. (A) Schematic overview of IL6 administration during colitis regimen, on day 10 mice were starved for 4 h post IL6 gavage and further orally administered FITC-Dextran. (B) Serum IL6 levels on day 10 in mice treated with 2.5% DSS.

Figure 26:
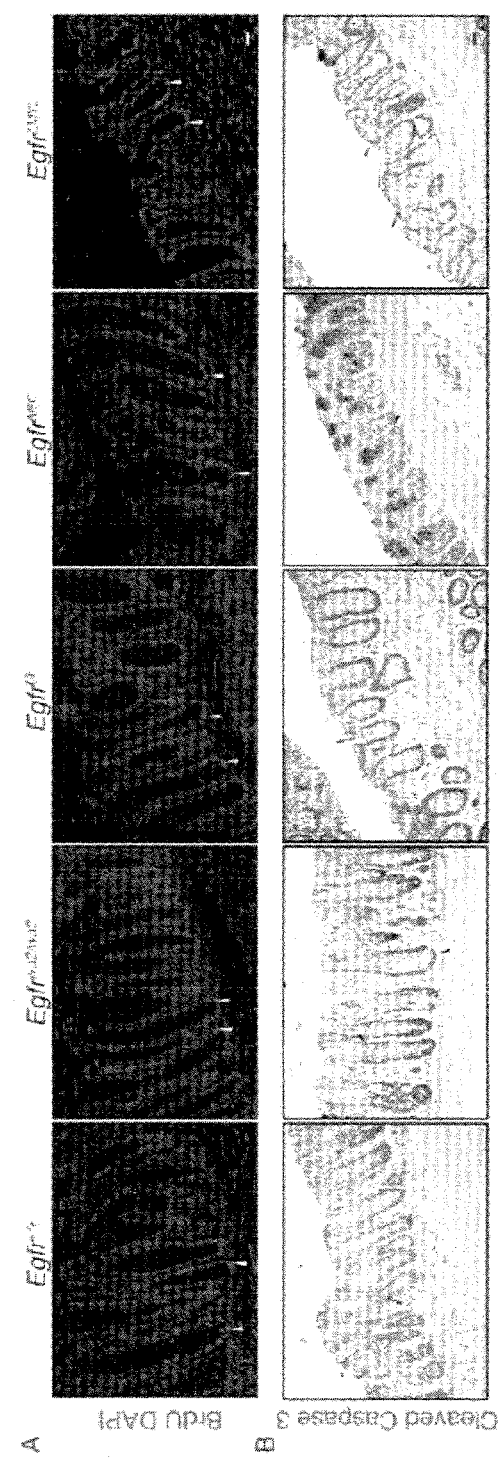

FIG. 26: Administration of IL6 during DSS treatment restores proliferation. Representative images of (A) BrdU immunofluorescence staining and (B) immunohistological staining for cleaved Caspase 3 on histological sections of mice administered IL-6 during DSS treatment. Arrowheads depict BrdU$^+$ and cleaved caspase 3$^+$ nuclei respectively, scale in images represents 20 µm.

The invention will now be described by reference to the following examples which are merely illustrative and are not to be construed as a limitation of the scope of the present invention.

EXAMPLES

Example 1

EGFR is Required in Liver Macrophages for IL-1-Induced IL-6 Production and Hepatocellular Carcinoma Formation Methods
Mice and Genotyping EGFR$^{f/f}$, EGFR$^{\Delta hep}$, and EGFR$^{\Delta liv}$ mice have been previously described (Natarajan, A. et al., 2007). EGFR$^{\Delta mac}$ and EGFR$^{\Delta hep/\Delta mac}$ mice were generated by crossing EGFR$^{f/f}$ or EGFR$^{\Delta hep}$ mice to LysM-Cre (Clausen, B. E. et al., 1999) transgenic mice. Male mice used in this study were kept in the facilities of the Medical University of Vienna in accordance with institutional policies and federal guidelines. Inducible EGFR deletion was achieved by 3 consecutive intraperitoneal (i.p.) injections with pIpC (400 µg) every third day in adult mice or by 3 consecutive i.p. injections with pIpC (150 µg) at day 9, 11, and 13 after birth. The genotyping of EGFR$^{\Delta hep}$ and EGFR$^{\Delta liv}$ has been previously described (Natarajan, A. et al., 2007). To genotype Alfp-Cre; LysM-Cre double transgenic mice a reverse primer situated in the Cre transgene (Cre-R (5'-CCCA-GAAATGCCAGATTACG-3') was combined with promoter specific primers for the particular transgene: Alb (5'-GCAAACATACGCAAGGGATT-3'), LysM (5'-GAGGGATGAAATTCCTGCAA-3'). The primers Δ-EGFR-F (5'-GCCTGTGTCCGGGTCTCGTCG-3') and Δ-EGFR-R (5'-CAACCAGTGCACCTAGCCTGGC-3') were used to detect deletion of EGFR (Δ-EGFR). The mice were of mixed 129/Sv×C57BL/6×CBA/J) genetic background and in all experiments EGFR expressing littermates (EGFR$^{f/f}$ or Cre+ or EGFR$^{+/+}$) served as controls to the respective EGFR deleted mice.

Liver Tumor Induction in Mice by DEN/PB

Liver tumors were induced by chemical carcinogenesis in male mice according to the scheme shown in FIG. 1A and quantification of liver tumors was performed as previously described (Eferl, R. et al., 2003). Mice were sacrificed when liver tumors were visible in EGFR$^{f/f}$, EGFR$^{f/+}$ or Cre+ littermate control mice, which occurred around 36 weeks in the Alfp-Cre, around 46 weeks in the Mx-Cre and around 63 weeks in the Alfp-Cre; LysM-Cre double transgenic background. The genetic background of the mice was mixed C57BL/6×129/Sv×CBA/J) but varied between the different Cre lines thus explaining the difference in the timing of tumor development. Littermates were used in all experiments. Tumor incidence was also controlled in EGFR$^{f/+}$ or EGFR$^{+/+}$ Alfp-Cre, Mx-Cre, LysM-Cre mice to exclude cre-mediated effects. Liver injury after DEN injection (100 mg/kg body weight) was determined by measuring the circulating transaminases AST/ALT (Reflotron, Roche) and by quantifying necrotic areas using H&E stained sections at the time points indicated.

Immunoblotting and Immunofluorescence

Protocols for Ki67 staining, BrdU in situ detection, TUNEL and immunoblotting have been previously described (Natarajan, A. et al., 2007; Lichtenberger, B. M. et al., 2010; Sibilia, M. et al., 2000; Drobits, B. et al., 2012). The following antibodies were used: EGFR (CST #4267), α-tubulin (sigma T9026), pEGFR (Tyr1068 CST #3777; Tyr1173 CST#4407), pJNK (CST #9255), JNK (CST #9252), pp38 (CST #4631), p38 (CST #9212), pIKKα/β (CST #2697), IKKβ(CST #2370), pNF-κB (CST #3033), NF-κB (CST #3034), Stat3 (sc-7179), pStat3 (CST#9145), actin (sigma A2066), F4/80 (serotec CI:A3-1 and eBioscience BM8), Ki67 (Novo Castra NCL-Ki67p), CD68 (ab-CAM, ab955), HMGB1 (CST #3935). Confocal images were taken with a Zeiss-LSM 700 microscope.

ELISA and MTT Assay

Protocols for ELISA have been previously described (Natarajan, A. et al., 2007; Lichtenberger, B. M. et al., 2010; Sibilia, M. et al., 2000; Drobits, B. et al., 2012). ELISA for IL-6, IL17A, IL22, IL23 (eBioscience), amphiregulin (R&D Systems), CCL2, IL-1β and IL-1α (BD Biosciences-Pharmigen) were performed following the manufacturer's instructions. MTT assay (EZ4U, Biomedica) was performed to quantify the number of viable Kupffer cells in the wells. The cytokine value was normalized to the number of viable Kupffer cells.

RT-PCR qRT-PCR analyses were performed as previously described (Natarajan, A. et al., 2007; Lichtenberger, B. M. et al., 2010; Sibilia, M. et al., 2000; Drobits, B. et al., 2012). The following primers were used: IL-1β-F (GGGCCT-CAAAGGAAAGAATC), IL-1β-R (TACCAGT-TGGGGAACTCTGC), IL-1α-F (CACCTTACACCTAC-CAGAGTGATTTG), IL-1α-R (TGTTGCAGGTC ATTTAACCAAGTG), IL-6-F (TTCCATCCAGTTGCCT-TCTTGG), IL-6-R (TTCTCATTTCCACGATTTCCCAG), HB-EGF-F (ACCAGTGGAGAATCCCCTATAC), HB-EGF-R (GCCAAGACTGTAGTGTGGTCA), TGFα-F (TCTGGGTACGTGGGTGTTC), TGFα-R (ACAGGTGA-TAATGAGGACAGCC), AR-F (GGTCTTAGGCTCAG-GCCATTA), AR-R (CGCTTATGGTGGAAACCTCTC), ER-F (CACCGAGAAAGAAGGATGGA), ER-R (TCACGGTTGTGCTGATAACTG), BTC-F (GACGAG-CAAACTCCCTCCT), BCT-R (ATCAAGCAGACCAC-CAGGAT), TACE-F (ACCACTTTGGTGCCTTTCGT), TACE-R (GTCGCAGACTGTAGATCCCT), ADAM12-F (AGACGTGCTGACTGTGCAAC), ADAM12-R (CCGT-GTGATTTCGAGTGAGAGA), EGF-F (CCCAG-GCAACGTATCAAAGT), EGF-R (GGTCATACCCAG-GAAAGCAA), Tubulin-F (AGAAGCATGGGGAGG ACTACA), Tubulin-R (GTCGTTGTTCATCACTGGCG).

Hepatocyte and Kupffer Cell Culture

Hepatocytes and Kupffer cells were isolated after liver perfusion according to previously published protocols (Smedsrod, B. et al., 1985) and either directly used for further analysis or cultured as follows. Hepatocytes were plated onto collagen pre-coated cell culture dishes and cultured in HepatoZyme-SFM (Gibco) supplemented with 2 mM glutamine and 1% penicillin-streptomycin (P/S). Hepatocytes were either treated with the indicated amounts of DEN for 24 hours or with 10 ng/ml TNFα (eBioscience) in the presence of cycloheximide (100 µg/ml, Sigma) for 12 hours to study the hepatoprotective role of EGFR. Kupffer cells were isolated and plated in RPMI 1640 with 10% FCS, 2 mM glutamine, 1% P/S for at least 24 hours followed by overnight starvation (in 0.5% FCS containing medium for cytokine induction; serum-free medium for signaling experiments). Kupffer cells were stimulated with IL-1β (10 ng/ml, eBioscience), EGF (10 ng/ml, Lonza), polyIC (20 μg/ml, GE Healthcare), imiquimod (12 μg/ml, Invivogen) and LPS (10 ng/ml, Invivogen) for the time period indicated. Whenever indicated, Kupffer cells were pre-incubated for 5 hours (for cytokine secretion) or 1 hour (for signaling experiments) prior to stimulation with the following inhibitors: BIBW2992 (0.005-20 μM, Selleck), cetuximab (0.01-1 μg/ml, Merck), TAPI-1 (10 μM, Peptides International), SP600125 (25 μM, Calbiochem), SB203580 (10 μM, Cell Signaling), and SC-514 (100 μM, Calbiochem). Since the number of Kupffer cells which can be recovered from one mouse is very low, it was technically impossible to perform Western Blot analysis for all indicated signaling molecules on one single batch of Kupffer cells. Usually Kupffer cells from 2 livers of the same genotype were pooled together to obtain around 20-30 μg of protein lysate.

Patient Material and Immunohistochemistry

Human samples were collected following informed consent according to the established protocol approved by the Ethic Committee of the Eastern Hepatobiliary Surgery Hospital and the Medical University of Vienna.

The 129 HCC patients of the Chinese cohort were randomly taken from the pool of HCC patients undergoing curative resection in the Eastern Hepatobiliary Surgery Hospital (Shanghai, China) between January 2002 and June 2006. None of these HCC patients received preoperative anticancer treatment. The normal liver tissues were collected from the distal normal liver sections of patients undergoing surgery for liver hemangioma, who did not show any evidence of chronic liver disease.

The 108 HCC patients of the European cohort were randomly taken from a pool of patients who underwent orthotopic liver transplantation for HCC at the Medical University of Vienna as previously published (Sieghart, W. et al., 2011). None of these HCC patients received preoperative anticancer treatment.

Immunohistochemistry and quantitative analyses (scoring) on all human tissues (Chinese and European cohorts) were performed by the same laboratory (China) in a blinded manner following standard procedures. The slides were incubated with the following primary antibodies: anti-EGFR (CST: #4267, 1:50); anti-CD68 (macrophage marker; abCAM: ab955, 1:200). Staining for EGFR in hepatocytes or Kupffer cells for both the European and Chinese patient cohort was semi-quantitatively examined and blindly scored by 2 independent observers using the following scale: 0=negative staining (0%-10% positive), +=weak signal (10%-20% positive), ++=intermediate signal (20%-50% positive) and +++=strong signal (>50% positive) as previously described (Wang, K. et al., 2010). There were only slight variations between the scoring results of the 2 pathologists and in such cases, the lower scoring was taken to generate Table 1 (see below).

Statistical Analysis

Mouse Experiments

Sample size calculation: For tumor studies 10 mice per group were considered to detect a relevant difference in means of 1.5 within-group standard deviations at a two-sided significance level of 0.05 and a power of 90%, which ensures 80% power in case of a 20% drop-out rate. For the EGFR$^{\Delta hep \Delta mac}$ experiment 6 mice per group were considered, which ensures a 90% power to detect a difference in means of 2 standard deviations at the same significance level of 0.05. Unless otherwise indicated, experiments in mice (various injections, ex vivo cell and tissue isolations etc.) were performed at least 3 times with 3 biological replicates. Quantifications on histological samples were performed by counting/measuring at least 10 microscopic fields (HPF where indicated) on at least 3 independent tissue samples.

Data are presented as mean±s.d or mean±s.e.m. Student's t-test for independent samples and unequal variances was used to assess statistical significance (*p<0.05, p<0.01, *p<0.001). Each tumor measurement contributed by one animal is the mean value over several liver sections. Based on the central limit theorem, a normal distribution of these animal-specific means can be assumed even if the underlying variable is not perfectly normally distributed. All statistical analyses were performed with the SPSS18.0 software. A two-sided P<0.05 was considered statistically significant.

Human Material

The statistical analyses were performed by the respective Chinese and Viennese laboratories.

Overall survival (OS) in both patient cohorts was defined as the time between the dates of surgery and death. Disease-free survival (DFS) was defined as the time between the dates of surgery and recurrence or death. Survival curves were calculated using the Kaplan-Meier method. Median survival times (OS) and their 95% confidence intervals (CIs) were reported. The survival in the European cohort is low for a current transplant population because many patients were transplanted with tumors that were too large (outside the now accepted Milan criteria) as previously described (Sieghart, W. et al., 2011). The log-rank test was used to assess the effects of patient variables on OS.

Results

HCC Formation in Mice Lacking EGFR in all Liver Cells

To investigate the function of EGFR during HCC formation in vivo, pIpC-inducible Mx-Cre transgenic mice (EGFR$^{f/f}$; Mx-Cre=EGFR$^{\Delta liv}$=EGFR$^{\Delta Mx}$) were employed, which delete the EGFR in parenchymal and non-parenchymal liver cells as well as several other organs (Natarajan, A. et al., 2007). In this, and subsequent transgenic mice, the chemical carcinogen diethylnitrosamine/phenobarbital (DEN/PB) (Eferl, R. et al., 2003) was used to induce HCC, as also shown in FIG. 1A, which occurs in a multistep process similar to the disease in humans. DEN-damaged hepatocytes undergo apoptosis and are replaced via compensatory proliferation of surviving hepatocytes, which can give rise to HCC if mutated by DEN (He, G. et al., 2011). For each experiment that follows, EGFR$^{f/f}$ are shown as control mice. They were littermates to the respective Cre positive mice resulting from EGFR$^{f/f}$×EGFR$^{f/f}$ Cre positive breedings and received the same treatment. However, to exclude Cre-mediated effects early on it was always confirmed that all the EGFR$^{+/+}$ Cre positive DEN-treated mice developed the same defects as the EGFR$^{f/f}$ DEN-treated controls. Complete EGFR deletion and lack of expression in EGFR$^{\Delta liv}$ mice was confirmed by Southern blot in livers (see FIG. 1B), and by immunohistochemistry (IHC) as well as Western blot analysis in tumors (see FIGS. 2A and 2B). By 46 weeks, control EGFR expressing mice had all developed tumors whereas in EGFR$^{\Delta liv}$ littermates there was a dramatic and significant decrease in tumor mass, area, and number, as also shown in FIGS. 2C and 2D. Analysis of EGFR$^{\Delta liv}$ tumors by Ki67 and TUNEL staining revealed a significant decrease in proliferation and an increase in apoptosis (see FIG. 2E), whereas proliferation and apoptosis in non-tumor tissue adjacent to HCCs were comparable between control EGFR expressing EGFR$^{f/f}$ mice and EGFR$^{\Delta liv}$ mice (see FIG. 1C). These results suggest that EGFR in liver cells promotes HCC formation by protecting them from DEN-induced apoptosis.

HCC Formation in Mice Lacking EGFR in Parenchymal Cells

In the EGFR$^{\Delta liv}$ mice (also referred to as EGFR$^{\Delta Mx}$ mice), EGFR was deleted in all liver cells (i.e., hepatocytes, Kupffer cells, endothelial cells and hepatic stellate cells). Given the known complexity of HCC and the likely involvement of different cell types HCC formation was also induced in mice lacking EGFR specifically in hepatocytes and bile duct cells (EGFR$^{f/f}$; Alfp-Cre=EGFR$^{\Delta hep}$) (Natarajan, A. et al., 2007). Absence of EGFR in parenchymal cells was confirmed by immunohistochemistry and Western blot analysis (see FIGS. 3A and 3B). In EGFR$^{\Delta hep}$ tumors, EGFR was detectable in the relatively low numbers of non-parenchymal cells where Alfp-Cre is not expressed (see FIG. 3A), which explains the presence of the unrecombined flox allele in the Southern blot of EGFR$^{\Delta hep}$ livers (see FIG. 4A). In direct contrast to EGFR$^{\Delta liv}$ mice, upon HCC induction by DEN (see FIG. 1A), EGFR$^{\Delta hep}$ mice developed significantly larger tumors, which were histological indistinguishable, compared to littermate control mice (see FIGS. 3C and 3D). This result was unexpected given EGFR was expected to play only a tumor promoting role. Proliferation in tumors was increased, which is contrary to that observed with EGFR$^{\Delta liv}$ tumors (see FIG. 3E). However, similar to EGFR$^{\Delta liv}$ mice, EGFR$^{\Delta hep}$ tumors also showed increased apoptosis (see FIG. 3E) suggesting that EGFR protects hepatocytes against DEN-induced apoptosis. To investigate this in more detail, DEN was injected into EGFR$^{f/f}$, EGFR$^{\Delta Mx}$ and EGFR$^{\Delta hep}$ mice and liver damage was monitored after 36, 48 and 72 hours by measuring the percentage of necrosis on H&E-stained sections. Already 36 hours after DEN injection, damaged areas were significantly increased in EGFR$^{\Delta Mx}$ and EGFR$^{\Delta hep}$ livers compared to littermate controls (see FIGS. 2F and 1D). In addition, aspartate transaminase (AST) and alanine transaminase (ALT) levels, markers of acute liver toxicity, were significantly increased in the serum (see FIGS. 1E and 1F).

To investigate further the nature of this hepatocyte damage, hepatocytes were isolated from EGFR$^{\Delta Mx}$ and control mice, were stimulated for 12 hours with DEN, and immunofluorescent staining for the necrotic marker high-mobility group box 1 (HMGB1) (Degryse, B. et al., 2001) was performed, which revealed a strong necrotic response specifically in EGFR-deficient hepatocytes (see FIG. 1G). EGFR-deficient hepatocytes were also more sensitive to apoptosis after TNFα/cyclohexamide (CHX) treatment, as indicated by the increase of cleaved caspase 3 (see FIG. 1H). Furthermore, in EGFR$^{\Delta Mx}$ and EGFR$^{\Delta hep}$ livers, cleaved caspase 3 was significantly increased in Zone III of the liver lobule, where DEN is mainly metabolized (Sell, S., 2002) (see FIG. 2G). Thus, apoptosis and necrosis are responsible for increased DEN-induced liver damage in EGFR$^{\Delta Mx}$ and EGFR$^{\Delta hep}$ mice, revealing that EGFR fulfills an important death-protecting function in hepatocytes.

During toxic hepatic injury, pro-inflammatory cytokines such as IL-1, IL-6 and TNFα activate an inflammatory repair process (Sakurai, T. et al., 2008). qRT-PCR analysis of hepatocytes isolated 6 and 48 hours after DEN injection revealed a significant increase in IL-1β expression in EGFR$^{\Delta Mx}$ and EGFR$^{\Delta hep}$ mice, whereas IL-1α expression was low and unchanged (see FIG. 2H). In contrast, when IL-1α/β levels were measured in total livers 24 hours after DEN treatment, it was observed that IL-1α expression was higher than IL-1β (see FIG. 2I), which confirms previous results (Sakurai, T. et al., 2008). Together, these results suggest that IL-1α is mainly released by non-parenchymal cells, possibly Kupffer cells/liver macrophages, and not by damaged hepatocytes. Increased IL-1β expression was also detected in EGFR$^{\Delta Mx}$ and EGFR$^{\Delta hep}$ tumors (see FIG. 2J). Moreover, a significantly stronger increase of IL-1β release was observed when EGFR-deficient hepatocytes were treated in vitro with DEN or TNFα (see FIGS. 3F and 11). Thus, hepatoprotection via EGFR signaling prevents continuous hepatocyte death and IL-1β release in HCC.

In both EGFR$^{\Delta Mx}$ and EGFR$^{\Delta hep}$ mice, EGFR protects cells from DEN-induced damage, but still EGFR plays opposing roles in promoting HCC formation illustrating the complex role of EGFR in tumorigenesis. To exclude that timing of EGFR deletion (late gestation in EGFR$^{\Delta hep}$ mice versus 7-week old mice in EGFR$^{\Delta Mx}$ mice) is responsible for the differences in HCC development between the two models, EGFR was deleted shortly after birth in EGFR$^{f/f}$; Mx-Cre mice (EGFR$^{\Delta liv*}$; also referred to as EGFR$^{\Delta Mx*}$) (see FIGS. 1A and 4C). Similar to EGFR$^{\Delta Mx}$ mice, also EGFR$^{\Delta Mx*}$ mice developed significantly less tumors of lower mass and area than their EGFR$^{f/f}$ littermate controls (see FIGS. 4D and 4E), indicating that not the timing of deletion, but rather the cell type, in which EGFR is deleted, accounts for the differences in HCC development between EGFR$^{\Delta Mx}$ and EGFR$^{\Delta hep}$ mice.

EGFR Expression in Kupffer Cells/Liver Macrophages Promotes HCC Development

It was hypothesized that the difference in HCC formation between EGFR$^{\Delta hep}$ and EGFR$^{\Delta liv}$ mice was caused by EGFR function in non-parenchymal cell types. To test this, IHC was performed for non-parenchymal cell markers in tumors of EGFR$^{\Delta hep}$ and EGFR$^{\Delta liv}$ mice compared to controls. There was no difference in the number of endothelial cells between the two mice (data not shown). However, specifically in tumors from EGFR$^{\Delta hep}$ mice, a 4-fold increase of F4/80-positive cells was observed, which could be liver-resident macrophages (known as Kupffer cells) or infiltrating macrophages (see FIGS. 5A and 5B). There was also a significant upregulation of serum CCL2 levels, a chemokine known to attract F4/80-positive cells, in EGFR$^{\Delta hep}$ but not in EGFR$^{\Delta liv}$ tumors (see FIGS. 5A and 5B). These results indicate that increased numbers of Kupffer cells and/or infiltrating macrophages expressing EGFR could contribute to increased HCC formation in EGFR$^{\Delta hep}$ mice. To test this directly, LysM-Cre transgenic mice were employed to generate EGFR$^{\Delta hep/\Delta mac}$ (EGFR$^{f/f}$; Alfp-Cre; LysM-Cre) mice, which lack EGFR in both hepatocytes and Kupffer cells/macrophages (see FIG. 5C). Similar to the EGFR$^{\Delta liv}$ and EGFR$^{\Delta mac}$ mice, EGFR$^{\Delta hep/\Delta mac}$ showed significantly fewer and smaller tumors when compared to littermate controls and EGFR$^{\Delta hep}$ mice (see FIGS. 5D and 5E). Thus, the increased HCC formation in mice lacking EGFR specifically in parenchymal cells (EGFR$^{\Delta hep}$) is caused by increased numbers of EGFR-expressing Kupffer cells/infiltrating macrophages. Finally, to test whether EGFR-expressing macrophages are responsible for HCC formation, HCC was induced in mice lacking EGFR only in macrophages (EGFR$^{f/f}$; LysM-Cre=EGFR$^{\Delta mac}$). Similar to EGFR$^{\Delta Mx}$ and EGFR$^{\Delta hep/\Delta mac}$ mice, EGFR$^{\Delta mac}$ mice displayed significantly smaller tumors when compared to the respective controls (see FIGS. 5D and 5E). These results thus reveal an unexpected tumor-promoting role for EGFR in Kupffer cells/liver macrophages during HCC formation.

EGFR Expression is Induced in Activated Kupffer Cells/Liver Macrophages Under Pathological Conditions Next it was confirmed that EGFR was expressed in Kupffer cells/liver macrophages isolated from untreated control, EGFR$^{\Delta hep}$ and EGFR$^{\Delta liv}$ livers. Cultures contained ≥98% Kupffer cells/macrophages (as confirmed by F4/80 staining, see FIG. 5F). Immunofluorescence and Western blotting revealed that EGFR was indeed expressed in Kupffer cells/macrophages isolated from EGFR$^{f/f}$ livers (see FIGS. 5F and 5J), a finding that has not been reported before. As expected, no EGFR expression was detected in Kupffer cells isolated from EGFR$^{\Delta mac}$ (see FIGS. 5G and 5J) and EGFR$^{\Delta Mx}$ mice (see FIG. 5J). EGFR levels in Kupffer cells/macrophages were similar in EGFR$^{\Delta mac}$ and control mice (see FIG. 5J) whereas EGFR protein was not present in hepatocytes isolated from EGFR$^{\Delta hep}$ and EGFR$^{\Delta liv}$ mice (see FIG. 5J). liver sections contained only very few EGFR positive Kupffer cells/macrophages (see FIG. 5H). However, 5 days after DEN injection, prominent EGFR expression was detected in F4/80 positive cells, indicating that EGFR expression is induced in activated Kupffer cells/liver macrophages under pathological conditions (see FIG. 5I).

In vivo, healthy and untreated EGFR$^{f/f}$ livers contained only very few EGFR-positive Kupffer cells/macrophages (see FIGS. 5H and 5K). However, 5 days after DEN injection, prominent EGFR expression was detected in F4/80-positive cells (see FIGS. 5I and 5K). Interestingly, increased levels of EGFR were also present in hepatocytes following DEN treatment (see FIG. 5L). Next it was investigated whether EGFR was induced in Kupffer cells/liver macrophages of HCCs. Immunohistochemistry on serial sections of EGFR$^{f/f}$ and EGFR$^{\Delta hep/\Delta mac}$ tumors revealed co-expression of EGFR and F4/80 in tumor tissue and adjacent tissue of EGFR$^{f/f}$ mice (see FIGS. 5M and 5O), but not in EGFR$^{\Delta hep/\Delta mac}$ tumors (see FIGS. 5N and 5P). Taken together, this finding indicates that EGFR expression is induced in activated Kupffer cells/liver macrophages under pathological conditions, a finding that has not been reported before.

The Presence of EGFR-Expressing Kupffer Cells/Liver Macrophages in Human HCC Correlates with Poor Prognosis As EGFR expression in Kupffer cells/liver macrophages had not been previously reported, it was hypothesized that this may be relevant for human HCC. Therefore, the expression of EGFR was analyzed by immunohistochemistry in 129 surgically resected HCC patient samples, predominantly Hepatitis B (HBV)-positive from China, in adjacent non-cancerous tissue, and in 15 "normal" livers (distal normal liver sections of patients undergoing surgery for liver hemangioma) (see Tables 1a and 1b below). Since chronic HBV is a less common cause of HCC in Europe and the US, EGFR expression was additionally investigated in an independent validation cohort of 108 European HCC patients who underwent liver transplantation for HCC (see Table 1a). This cohort of HCC patients had predominantly alcohol-, NASH- and HCV-induced liver cirrhosis (see Table 1b). EGFR staining for both cohorts was examined and blindly scored by two independent pathologists using the previously published scale (Wang, K. et al., 2010) described in the methods section above.

TABLE 1a

EGFR expression in hepatocytes and Kupffer cells of the Chinese cohort and the European cohort (in brackets).

| EGFR expression | Hepatocytes | | | Kupffer cells | | |
|---|---|---|---|---|---|---|
| | HCC | Tissue adjacent to carcinoma | Normal liver | HCC | Tissue adjacent to carcinoma | Normal liver |
| 0 | 70/129 (69/108) | 83/129 (57/108) | 11/15 | 71/129 (71/108) | 114/129 (76/104*) | 15/15 |
| + | 35/129 (31/108) | 30/129 (40/108) | 3/15 | 33/129 (36/108) | 8/129 (27/104*) | 0/15 |
| ++ | 18/129 (6/108) | 13/129 (7/108) | 1/15 | 20/129 (1/108) | 5/129 (1/104*) | 0/15 |
| +++ | 6/129 (2/108) | 3/129 (0/108) | 0/15 | 5/129 (0/108) | 2/129 (0/104*) | 0/15 |

*In 4 patients, no adjacent tissue was available.

TABLE 1b

Relationship between EGFR positivity in Kupffer cells and the clinicopathological characteristics.

| | EGFR expression in Kupffer cells | | |
|---|---|---|---|
| Variable | 0<br>China: n = 71<br>EU: n = 49* | +, ++, +++<br>n = 58<br>n = 59** | P value |
| Age | | | |
| China: median years (range) | 49 (30-78) | 49 (21-68) | 0.8646# |
| EU: median years (range) | 57 (33-68) | 55 (28-67) | 0.349# |
| Sex | | | |
| China: , M:F | 65:6 | 51:7 | 0.4971 |
| EU: M:F | 40:9 | 50:9 | 0.666 |
| AFP | | | |
| China: (µg/L), <20:≥20 | 42:29 | 16:42 | 0.0004 |
| EU: | n.d. | n.d. | n.d. |
| Etiology: | | | |
| China: HBsAg, positive:negative | 55:16 | 53:5 | 0.0332 |
| EU: alc:viral:other | 15:25:9 | 18:28:13 | 0.884 |
| Diameter | | | |
| China: <3 cm:3-5 cm:>5 cm | 31:14:26 | 13:21:24 | 0.0222 |
| EU: median cm (range) | 2.5 (1-13) | 4.5 (1-24) | <0.001# |
| Microvascular Invasion | | | |
| China: yes:no | 11:60 | 18:40 | 0.0354 |
| EU: yes:no | 7:42 | 19:40 | 0.030 |
| TNM staging | | | |
| China: I:II:III:(IV) | 60:8:3 | 38:12:8 | 0.0339 |
| EU: I:II:III:(IV) | 11:12:26:0 | 2:12:44:1 | 0.008 |
| Recurrence of HCC, | | | |
| China: no:yes | 45:26 | 22:36 | 0.0040 |
| EU: no:yes | 49:0 | 29:30 | <0.001 |

AFP: alpha-Fetoprotein, TNM: classification of malignant tumors (Tumor, Node, Metastasis).
Mann-Whitney test.
*includes samples where tumor and tissue adjacent to carcinoma were negative for EGFR in Kupffer cells,
**includes samples where either tumor or tissue adjacent to carcinoma (or both) were positive for EGFR in Kupffer cells.

In the Chinese patient cohort, more than 73% of "normal" liver tissue adjacent to the tumor showed no detectable EGFR expression (see Table 1a). However, EGFR expression was found in tumor cells of 45.7% HCC samples, and in 35.7% of hepatocytes of adjacent tissue (see Table 1a and FIG. 6A). High expression of EGFR (++, +++) was more prevalent in HCC compared to non-cancerous lesions or normal tissue (see Table 1a and FIG. 6A), which confirms previous reports (Buckley, A. F. et al., 2008). Similar results were observed for EGFR expression in hepatocytes analyzed in cancerous and non-cancerous liver tissue of the European HCC cohort (see Table 1a). For both cohorts, EGFR expression in hepatocytes of tumors did not show significant prognostic value for patient's overall survival or disease free survival after surgery (see FIGS. 6B-6E and Table 1a) and no significant relationship between EGFR expression in hepatocytes and clinico-pathological characteristics was found (data not shown).

To analyze the expression of EGFR specifically in liver macrophages adjacent tissue sections were stained with anti-EGFR and the macrophage marker CD68. In "normal" liver tissue, almost all cells positive for the macrophage marker CD68 did not express detectable levels of EGFR (see Table 1a). In contrast, 45% of the Chinese and 34% of the European samples harbored EGFR-expressing CD68-positive cells in the tumors ranging from + to +++(see FIGS. 7A and 7B, FIG. 6F, and Table 1a). EGFR-positive macrophages in HCCs were mostly observed together with EGFR positive tumor cells (data not shown). EGFR-expressing macrophages were also present within the non-cancerous tissue adjacent to the carcinoma: 12% for the Chinese and 27% for the European cohort. It is interesting to note that in the European cohort there were more EGFR positive macrophages in the adjacent tissue, which might be due to the cirrhotic condition present in the liver of these patients. The specificity of EGFR expression on CD68 positive cells was confirmed by co-staining for EGFR and CD68 in a few available fresh frozen human HCC tissue samples (see FIG. 6G). EGFR-expressing Kupffer cells in HCCs were associated with poor clinical outcome of Chinese patients after surgical tumor resection and European patients after liver transplantation mirrored by significantly reduced overall survival and disease free survival (see FIGS. 7C-7F). α-Fetoprotein (AFP), a marker that may be increased in liver inflammation and HCC, was significantly higher in HCC patients with EGFR-positive macrophages (see Table 1b). In the European cohort, EGFR-positive liver macrophages were associated with more aggressive tumors and patients suffering from HCC recurrence after liver transplantation had EGFR-positive macrophages in their tumors (see Table 1b). Multivariate analysis of the European and Chinese cohort confirmed EGFR-positive liver macrophages as significant predictor of overall survival and disease free survival (data not shown) (Mazzaferro, V. et al., 1996).

To analyze whether total numbers of CD68-positive cells—regardless of EGFR expression—had an impact on HCC prognosis, the patient samples were grouped into low and high macrophage counts considering the median of the respective patient cohorts as a cut-off. For the European cohort, the number of Kupffer cells/liver macrophages alone was not predictive for overall and disease-free survival (see FIGS. 7I and 7J). However, total numbers of macrophages negatively correlated with overall survival and disease-free survival of Chinese patients (see FIGS. 7G and 7H). When the total number of macrophages were further subjected to multivariate Cox proportional hazards analysis, it was not an independent and significant factor for the survival of patients with HCC in contrast to the presence of EGFR-positive Kupffer cells/liver macrophages (data not shown). Collectively, these data demonstrate that it is not the overall number of liver macrophages, but the number of EGFR-positive liver macrophages present in HCC, which is predictive for overall and disease-free survival.

EGFR Deficient Kupffer Cells Fall to Produce IL-6

Next the mechanism was analysed whereby EGFR promotes tumorigenesis in liver macrophages. IL-6, a major HCC promoting cytokine (Naugler, W. E. et al., 2007), is produced at high levels by Kupffer cells in response to IL-1 derived from damaged hepatocytes, and stimulates compensatory hepatocyte proliferation through IL-6R activation (Grivennikov, S. I. et al., 2010; Sakurai, T. et al., 2008). Thus, IL-6 production was analyzed in mice lacking EGFR in different liver cells. IL-6 serum levels were strongly induced upon DEN injection already after 6 hours only in control (EGFR$^{f/f}$) and EGFR$^{\Delta hep}$ mice (which have EGFR expressing Kupffer cells/liver macrophages), but not in EGFR$^{\Delta liv}$ and EGFR$^{\Delta hep/\Delta mac}$ mice, which lack EGFR in liver macrophages (see FIG. 8A). Next IL-6 mRNA levels were analyzed in liver macrophages isolated from EGFR$^{f/f}$, EGFR$^{\Delta hep}$ and EGFR$^{\Delta liv}$ mice 6 hours after DEN injection. IL-6 expression levels in EGFR-expressing Kupffer cells (EGFR$^{f/f}$ and EGFR$^{\Delta hep}$) were significantly higher than in EGFR-deficient Kupffer cells (EGFR$^{\Delta liv}$) (see FIG. 8B). Importantly, significantly higher IL-6 levels were also found in the plasma of Chinese HCC patients displaying EGFR positive Kupffer cells in their tumors (see FIG. 8C). Interestingly, this occurred in association with HBV infection (see FIG. 8D), indicating that infections and inflammatory conditions lead to upregulation of EGFR in Kupffer cells with consequent increased IL-6 production. For the European cohort, patient plasma was not available. Thus, upon DEN-induced liver damage, EGFR in Kupffer cells/liver macrophages is required to induce expression of IL-6, which promotes HCC formation.

To further investigate whether IL-1 can induce IL-6 production in liver macrophages in an EGFR-dependent manner, IL-6 levels were quantified after incubation of isolated Kupffer cells/liver macrophages with IL-1β in vitro for 6 hours. IL-6 transcripts and IL-6 protein in the culture medium were induced by IL-1β in Kupffer cells expressing EGFR, but not in EGFR-deficient liver macrophages (see FIGS. 8E and 8F). The levels of IL-6 mRNA detected in EGFR-deficient liver macrophages were almost as low as those seen in liver macrophages isolated from MyD88$^{-/-}$ mice, which are deficient in IL-1R signaling (see FIG. 8E). IL-6 production in Kupffer cells could also be prevented by BIBW2992 (EGFR kinase inhibitor) and cetuximab (EGFR-inhibiting antibody) in a dose-dependent manner (see FIGS. 9A and 9B). Other inflammatory cytokines such as IL-17A, IL-22 and IL-23 were not detectable in the supernatants of EGFR$^{f/f}$, EGFR$^{\Delta liv}$ as well as MyD88$^{-/-}$ Kupffer cells following IL-1β or EGF stimulation (data not shown). Notably, IL-6 production was comparable between EGFR-expressing and EGFR-deficient Kupffer cells after stimulation with other Toll-Like Receptor (TLR) agonists that activate IL-6 production such as polyIC, imiquimod and LPS (see FIG. 9C) showing that EGFR-deficient Kupffer cells are not intrinsically impaired in IL-6 production. Thus, EGFR-deficient Kupffer cells cannot produce IL-6 in response to IL-1, indicating that EGFR-dependent IL-6 production is downstream of IL-1R signaling.

Kupffer cells release IL-6 in response to signals from damaged hepatocytes, which in turn stimulates compensatory hepatocyte proliferation. Hepatocyte proliferation was therefore analyzed after short term DEN treatment in vivo in EGFR$^{\Delta hep}$, EGFR$^{\Delta liv}$ and the matched EGFR$^{f/f}$ control mice. The strongest increase of BrdU incorporation was observed in livers of EGFR$^{\Delta hep}$ mice likely because DEN-induced damage is high (because of lack of EGFR in hepatocytes) and the Kupffer cells/liver macrophages still express EGFR and thereby produce IL-6 to stimulate proliferation. In contrast, proliferation was lower in EGFR$^{\Delta liv}$ and control mice, likely because of impaired IL-6 production by EGFR negative Kupffer cells/liver macrophages, and less severe DEN-induced damage in control (EGFR expressing) hepatocytes, respectively (see FIG. 8G). Together, these results show that increased compensatory proliferation correlates with increased IL-6 levels and increased HCC formation.

IL-1β-Induced IL-6 Production Involves ADAM-17-Dependent Cleavage of EGFR Ligands and JNK-, p38- and IKK2-Signaling To identify the molecular mechanism by which EGFR signaling in Kupffer cells leads to IL-1-induced IL-6 production, EGFR-expressing Kupffer cells were isolated from EGFR$^{\Delta hep}$ and matched control EGFR$^{f/f}$ mice, were incubated with IL-1, and EGFR ligand expression was quantified by using qRT-PCR. Except for BTC, all other EGFR ligands were significantly induced by IL-1β (see FIG. 10A). Among those, HB-EGF, TGFα, AR, and ER are proteolytically released by TACE/ADAM17 (a disintegrin and metalloprotease/TNFα converting enzyme) (Blobel, C. P., 2005), which was also induced by IL-1β (see FIG. 10A). TACE and EGFR ligands were not induced by IL-1 in MyD88$^{-/-}$ Kupffer cells, indicating that their induction is under direct control of IL-1R signaling (see FIG. 10A). EGFR ligands and TACE were also induced by IL-1β in Kupffer cells lacking EGFR (EGFR$^{\Delta liv}$) suggesting EGFR-independent transcriptional regulation (see FIG. 10A). Consistent with this, the release of the EGFR ligand AR into the culture medium of IL-1β stimulated Kupffer cells was significantly increased in both EGFR expressing and EGFR-deficient Kupffer cells, but did not occur in MyD88 Kupffer cells or when inhibiting TACE (TAPI-1) (see FIG. 10B). AR release could also be blocked by the IKK inhibitor Sc-514, but not by inhibiting JNK or p38 signaling using SP600125 and SB203580, respectively (see FIG. 10B), demonstrating that release of AR occurs via IKK-dependent activation of TACE.

These results demonstrate that in Kupffer cells IL-1R signaling controls primarily the expression of EGFR ligands and the protease TACE, which likely leads to EGFR activation and downstream IL-6 production. To test this, first IL-6 release was analyzed in isolated Kupffer cells/liver macrophages in the presence of various inhibitors. TAPI-1 (TACE-1 inhibitor) and BIBW2992 (EGFR inhibitor) blocked IL-1β-induced release of IL-6 in EGFR-expressing Kupffer cells (isolated from EGFR$^{f/f}$ and EGFR$^{\Delta hep}$ mice) to a similar extent as observed in untreated MyD88$^{-/-}$ (impaired IL-R signaling) and EGFR-deficient Kupffer cells (see FIG. 10C). This demonstrates a linear pathway from IL-1R signaling via MyD88, TACE, and EGFR ligands to EGFR signaling and IL-6 production. Next the ability of the EGFR ligand EGF to induce IL-6 release by isolated Kupffer cells was analyzed. EGF stimulation was sufficient and equally as potent as IL-1β in inducing IL-6 release in EGFR expressing Kupffer cells (see FIGS. 10C and 10D). Importantly, EGF, but not IL-1β, was able to fully restore IL-6 production in MyD88$^{-/-}$ Kupffer cells (see FIG. 10D). These results indicate that MyD88 is primarily required to induce EGFR ligand production, and that EGFR activation and thereby IL-6 production is downstream of IL-1R/MyD88 signaling. Consistent with this, IL-6 production by isolated Kupffer cells/liver macrophages induced by either EGF or IL-1β was prevented in the absence of EGFR (EGFR$^{\Delta liv}$). Pre-incubation of EGFR-positive liver macrophages with SP600125 (JNK inhibitor), SB203580 (p38 inhibitor), or Sc-514 (IKK inhibitors), also inhibited IL-6 production induced by either EGF or IL-1β, indicating the importance of JNK, p38 and NFκB signaling downstream of EGFR in mediating IL-6 production (see FIG. 10C).

To directly demonstrate activation of the EGFR, EGFR phosphorylation was analyzed in isolated Kupffer cells. IL-1β stimulation was able to induce EGFR phosphorylation in EGFR expressing Kupffer cells to a similar extent as EGF treatment. This did not occur in EGFR-deficient (EGFR$^{\Delta liv}$) Kupffer cells (see FIGS. 10E and 10F). IL-1β-induced EGFR transactivation was blocked by p38 inhibition (SB203580) but not by JNK (SP600125) or IKK (Sc-514) inhibition indicating that activation of p38 is necessary for EGFR activation (see FIG. 10E). A similar requirement for p38 for EGFR transactivation by LPS has been recently described (McElroy, S. J. et al., 2012). JNK, p38, IKKα/β and NFκB phosphorylation following IL-1β stimulation of EGFR-expressing and EGFR-deficient Kupffer cells could be efficiently blocked by respective inhibitors (see FIG. 10E). Except for IKK and NFκB, JNK and p38 were also activated following EGF stimulation of wild-type Kupffer cells (see FIG. 10F). Together, these data show that IL-1β stimulation of Kupffer cells leads to EGFR ligands and ADAM17 expression/induction with subsequent p38-dependent EGFR transactivation required for IL-6 production via JNK, p38 and IKK, as also shown in FIG. 11.

Discussion

EGFR is frequently overexpressed in human HCC, but its relevance for malignant progression is poorly understood. In the context of the present invention, the function of EGFR in HCC has been molecularly dissected by employing mice lacking EGFR in different liver cells, and it has been found that EGFR is expressed in Kupffer cells, where it plays a tumor-promoting role.

The present findings might provide a possible explanation for the poor response of unstratified advanced stage HCC patients to known EGFR targeted therapies. Based on the results provided herein, it is concluded and expected that only HCC patients with EGFR expression in liver macrophages alone or in both tumor cells and liver macrophages will show a therapeutic effect when treated with EGFR inhibitors/antagonists targeting liver macrophages. If EGFR is expressed only in tumor cells of HCC, it is expected that EGFR inhibitors/antagonists may even promote tumorigenesis, since the genetic results provided herein revealed that loss of EGFR in hepatocytes promotes HCC. Clinical follow-up studies are needed to re-evaluate the use of EGFR inhibitors in HCC, and to consider the possibility of targeting specific cell populations. At this stage, it is also possible that EGFR-expressing Kupffer cells play a tumor-promoting role only in the early stages of HCC development. Should this be the case, patients with advanced stage HCC would likely not benefit from EGFR targeted therapies, thus providing an explanation for the poor therapeutic effects seen in clinical trials with erlotinib. However, patients with HBV or HCV infections might benefit from EGFR inhibitor treatment in early disease stages to prevent HCC development. It will therefore be interesting to explore the predictive power of EGFR-expression in Kupffer cells also in patients in more advanced disease stages. Treatment of patients with EGFR positive Kupffer cells with EGFR inhibitors selectively targeting Kupffer cells could allow for improved HCC treatment in preselected patient populations.

The results shown herein also provide novel mechanistic insights into hepatocarcinogenesis and highlight the complexity of EGFR signaling in disease progression. It has been shown that EGFR plays a hepatoprotective role during DEN-induced liver damage, as absence of EGFR renders hepatocytes more susceptible to DEN-induced damage leading to increased IL-1β secretion and subsequent enhanced stimulation of Kupffer cells (see FIG. 11). This occurs in both mouse models lacking EGFR in parenchymal cells (EGFR$^{\Delta hep}$ and EGFR$^{\Delta liv}$ mice). However, the induction of IL-6 production in Kupffer cells is strictly dependent on the expression of EGFR and occurs in a bimodal way involving first IL-1R/MyD88 signaling followed by TACE/EGFR-L production and p38-dependent EGFR transactivation (see FIG. 11). In mice lacking EGFR only in hepatocytes (EGFR$^{\Delta hep}$), IL-6 secretion and compensatory proliferation are elevated leading ultimately to increased HCC formation. Additional deletion of EGFR in Kupffer cells/macrophages (EGFR$^{\Delta liv}$ and EGFR$^{\Delta hep/\Delta mac}$ mice) impairs HCC development, despite increased liver damage, as EGFR-deficient Kupffer cells cannot produce IL-6 to stimulate compensatory proliferation (see FIG. 11).

In conclusion, a crucial role for EGFR signaling in Kupffer cells/macrophages during inflammation-driven HCC formation has been identified, demonstrating for the first time that EGFR signaling plays a tumor-promoting function in non-tumor cells. Moreover, the present results and findings indicate that the determination of the expression of EGFR specifically in macrophages such as Kupffer cells allows to identify those patients that are susceptible to the treatment with an EGFR inhibitor/antagonist and thereby allows for an improved personalized therapy of inflammation-associated cancer such as HCC.

Example 2

EGFR Signaling in Myeloid Cells of the Lamina Propria Promotes Colorectal Cancer Development Introduction The link between inflammatory bowel disease (IBD) such as Crohn's disease, ulcerative colitis and colitis-associated cancer (CAC) has been described by numerous studies involving both human and animal models, where the severity of inflammation is portrayed as an important determinant for CAC development (Ben-Neriah, Y. et al., 2011; Danese, S. et al., 2010; Hanahan, D. et al., 2012; Terzic, J. et al., 2010; Eaden, J. A. et al., 2001; Ekbom, A. et al., 1990; Gupta, R. B. et al., 2007; Rutter, M. et al., 2004). The common practice for studying colitis in mice involves administration of synthetic detergents in drinking water such as dextran sulfate sodium salts (DSS) (Wirtz, S. et al., 2007). An advantage of the DSS protocol is also its ability to induce CAC, when implemented after administration of a genotoxic carcinogen such as azoxymethane (AOM). DSS induces colitis via tissue injury which renders the innate immune cells of the lamina propria exposed to the microbiota of the lumen causing their activation, which further secrete cytokines that heavily influence the course of disease pathology (Bollrath, J. et al., 2009(a); Chalaris, A. et al., 2009; Fichera, A. et al., 2007; Gabay, C., 2006; Hobbs, S. S. et al., 2011; Lee, C. H. et al., 2010).

The epidermal growth factor receptor (EGFR), a member of the ErbB family of receptor tyrosine kinases (RTK's) is well known to exert its influence on various epithelia by controlling cellular proliferation, differentiation, barrier integrity, etc (Egger, B. et al., 2000; Franzke, C. W. et al., 2012; Helmrath, M. A. et al., 1997; Sibilia, M. et al., 1995; Threadgill, D. W. et al., 1995; Yarden, Y. et al., 2001; Yamaoka, T. et al., 2008). The requirement of a robust EGFR signaling in the intestine is very well highlighted in previous studies employing Egfr$^{-/-}$ mice which show delayed development of the intestine starting from E14.5 and are born with stunted villi and showed proliferative defects in the enterocytes (Sibilia, M. et al., 1995; Threadgill, D. W. et al., 1995; Miettinen, P. J., 1995).

Attempts to define the role of EGFR in IBD have led to outcomes which show a highly complicated role for this molecule. In a human clinical trial, localized stimulation of EGFR was shown to alleviate the symptoms in colitis (Sinha, A. et al., 2003). Studies conducted with hypomorphic Egfr$^{wa2/wa2}$ mice (Egger, B. et al., 2000; Yan, F. et al., 2011) that express a mutant EGFR which retains only 5%-10% of its activity showed hypersensitivity to oral DSS treatment resulting in a pronounced increase in severity of colitis with considerable mucosal damage (Luetteke, N.C. et al., 1994). The mutant EGFR is unable to protect against DSS induced colitis even upon stimulation with exogenous EGF (Egger, B. et al., 2000) and in another study it weakened re-adaptation of the intestine after surgical resection (Helmrath, M. A. et al., 1997). However, during steady state the Egfr$^{wa2/wa2}$ mice do not show any structural defects in most organs, but are born with open eyes and develop a wavy coat like the Tgfa$^{-/-}$ mice which develop hair follicle defects (Luetteke, N.C. et al., 1993; Mann, G. B. et al., 1993). Other studies that used targeted genetic deletion on IECs describe EGFR expression on enterocytes as dispensable during DSS induced colitis as the mice lacking EGFR on IECs behaved similar to EGFR sufficient mice and did not show any difference in loss of barrier function and mucosal injury. Another study also showed that conditional ablation of EGFR on IECs did not affect the re-adaptation of the small intestine after surgical resection (Yan, F. et al., 2011; Rowland, K. J. et al., 2012). Such contravening results have further obscured the current understanding and in addition raised new questions as on which cells type does the EGFR play an important role; as IEC specific EGFR conditional KO mice display the same resilience to DSS colitis as WT mice while a global knockdown with Egfr$^{wa2/wa2}$ mice causes susceptibility.

The role of EGFR as a pro-tumorigenic molecule in CAC is also described. Studies have highlighted the requirement of EGFR expression on IECs for formation of aberrant crypt foci and AOM-DSS induced tumors, by demonstrating reduced tumor formation in mice treated with anti-EGFR pharmacological inhibitors or in mice expressing hypomorphic Egfr$^{wa2}$ alleles (Fichera, A. et al., 2007; Cohen, G. et al., 2006; Dougherty, U. et al., 2009; Roberts, R. B. et al., 2002). In human gastric cancers as well, prescription of cetuximab and panitumumab as an anti-EGFR therapy remains one of the widely practiced treatments. Such EGFR blocking strategies involving either pharmacological inhibitors or mAb's or both, though very effective, result in global inhibition of EGFR, which in turn leads to many adverse effects in addition to poor prognosis to therapy. Indeed, a recent study showed in an animal model that total EGFR inhibition by employing the dominant negative Egfr$^{wa5}$ or hypomorphic Egfr$^{wa2}$ expressing mice not only lead to increased colitis severity and loss of barrier function in a spontaneous model of colitis using il10$^{-/-}$ mice, but in fact the complete block of EGFR heightened the early onset of colorectal tumors many fold (Dube, P. E. et al., 2012). In addition the Egfr$^{wa5}$ also had no effect on tumor incidence in AOM-DSS induced tumors but in fact increased the progression of tumors by promoting invasiveness (Dube, P. E. et al., 2012).

Such results demonstrate that the role of EGFR in IBD and CAC is poorly understood, as during colitis models total knockdowns have led to increased susceptibility while conditional KOs show no effect, while in CAC studies with total knockdowns alone show increased tumor progression. These results also point towards a possible tumor suppressive role of EGFR which is yet to be addressed. Collectively these observations also point towards the role of EGFR in non-epithelial cells in intestinal cancers, namely the cells of the lamina propria, while its expression on IECs is largely redundant. The expression of EGFR on non-epithelial cells of the intestine has been reported (Eales-Reynolds, L. J. et al., 2001), but only recently some limited efforts have been made to address this aspect in colitis (Lu, N. et al., 2014). However, an attempt to address its comprehensive role in colitis and CAC has never been attempted before.

During epithelial injury EGFR is described to be stimulated locally in a paracrine or exocrine manner by EGF, which secreted from cells that arise temporarily in ulcerated regions (Wright, N. A. et al., 1990). Stimulation of EGFR occurs via ligands released from the cell membrane due to proteolytic cleavage of membrane bound ligand precursors by membrane bound metalloprotease-disintegrins, such as TNF-converting enzyme (TACE), also known as A Disintegrin and Metalloproteinase-17 (ADAM-17). Most fetuses of ADAM-17 hypomorphic mice (Adam17$^{ex/ex}$) die in utero and the few surviving ones show phenotypic similarities with Egfr$^{-/-}$ mice like open eyes at birth and also skin, hair follicle defects, etc (Sibilia, M. et al., 1995; Threadgill, D. W. et al., 1995; Peschon, J. J. et al., 1998). In addition to growth factor ligands, ADAM17 also facilitates signaling of cytokines such as TNFα and IL-6, via ecto-domain shedding of their membrane bound precursors. Both cytokines are mainly secreted by both tissues-resident, as well as infiltrating immune cells during an infection or injury which aid tissue regeneration and wound healing (Grivennikov, S. et al., 2009; Jin, X. et al., 2010). Additionally, they have also been implicated in prognosis of colitis, IBD and CAC as mice deficient in IL-6 show reduced tumor burden (Grivennikov, S. et al., 2009; Putoczki, T. L. et al., 2013). Moreover, elevated serum levels of IL-6 have been directly correlated with poor clinical prognosis in human cancers (Kim, S. et al., 2008).

Another signaling pathway currently believed to be active in such pathological conditions (Sibilia, M. et al., 1995; Threadgill, D. W. et al., 1995; Peschon, J. J. et al., 1998) is the IL-6 trans-signaling pathway, where IL-6 signals via its soluble IL6 receptor (IL6R), generated by ADAM17-mediated proteolytic cleavage in cells that do not express the membrane-bound IL6R, further leading to STAT3 activation via membrane-bound glycoprotein-130 (gp130). Inhibition of IL-6 trans-signaling by exogenous administration of gp130 in a mouse model of CAC led to substantial decrease of both colitis as well as tumor development (Kim, S. et al., 2008; Matsumoto, S. et al., 2010).

The intestinal mucosa is composed of a variety of cells, like IECs, which aid in the absorption of food, as well as non-epithelial cells present in the lamina propria, which are of both myeloid and hematopoietic origin, that serve to protect the intestinal lining during an infection or epithelial damage. A tumor, though mainly composed of cells of epithelial origin, also contains cells of hematopoietic origin including myeloid cells and tumor associated immune cells in its stroma, which have been described to heavily influence the progression of tumors (Danese, S. et al., 2010; Garlanda, C. et al., 2007). In the present study, conditional knock-out mice were employed, in which EGFR was selectively deleted on IECs and myeloid lineage cells. It has been demonstrated for the first time that EGFR expression on myeloid cells of the lamina propria is an important factor in prognosis of colitis and the risk of developing CAC. Moreover, the observations made herein describe a hitherto unknown barrier protective role of EGFR via IL-6 production in non-IECs intestinal injury, which is also an important requirement for survival and subsequent proliferation of transformed preneoplastic colon epithelial cells.

Material and Methods

Mice

All animal experiments conducted were compliant with federal laws and guidelines of the Medical University of Vienna. Egfr$^{f/f}$ mice (Natarajan, A. et al., 2007) were bred with hemizygous Villin-Cre (el Marjou, F. et al., 2004) and LysozymeM-Cre transgenic mice (Clausen, B. E. et al., 1999), resulting in Villin-cre Egfr$^{f/+}$ mice or LysM-cre Egfr$^{f/+}$, which were further bred to generate homozygous Egfr$^{f/f}$ mice expressing either Villin-cre (Egfr$^{\Delta IEC}$) or LysM-cre (Egfr$^{\Delta MYL}$). Mice were genotyped by PCR for the respective cre transgenes and cre negative littermates were used as controls. Egfr$^+$, Egfr$^f$ and Egfr$^\Delta$ alleles were detected by PCR using the following primers R4: GCCTGTGTC-CGGGTCTCGTCG, R6: CAACCAGTGCACCTAGC-CTGG and Egfr-fwd1: AAGTTTAAGAAACCCCGCTC-TACT. Apc$^{Min/+}$ mice were genotyped as described in Musteanu, M. et al., 2010.

Southern Blotting

Intestinal epithelial cells (IECs) were isolated as described in earlier studies (Musteanu, M. et al., 2010). Genomic DNA was extracted from IECs by salt and ethanol precipitation; 10 μg DNA was digested with HindIII and probed using a XbaI/HindIII digested fragment from intron1 of egfr.

Colitis and Tumorigenesis

Colitis was induced by administering 2.5% dextran sulfate sodium salt (DSS) (MP Biomedicals, 0216011080) in autoclaved drinking water for 5 d followed by 5 d of normal water (Chalaris, A. et al., 2010). Colon tumors in mice were induced as previously described (Wirtz, S. et al., 2007; Tanaka, T. et al., 2003). Briefly, mice were injected i.p. with 7.5 mg/kg azoxymethane (AOM) (Sigma-Aldrich, A5486) followed by repeated administration of DSS. 300 U recombinant mouse IL-6 (ImmunoTools GmbH, Germany) was administered by oral gavage. Egfr$^{f/+}$ Cre positive tumors were comparable to wild-type tumors and were thus analysed as controls.

Histology and Immunohistochemistry

Mice were injected with 10 mg/kg BrdU 2.5 hrs prior to sacrifice. The colons were extracted, flushed with ice cold PBS to remove feces, fixed overnight at 4° C. in neutral buffered 4% formaldehyde as "Swiss Rolls", which were further dehydrated, embedded in paraffin and sectioned. Sections were stained with Haematoxylin and Eosin (Sigma), Alcian blue, Giemsa and PAS. Colitis severity and tumor stage were scored and graded by pathologists in a blinded manner according to previously described criteria (Dube, P. E. et al., 2012; Musteanu, M. et al., 2010). For immunohistochemistry, sections were dewaxed, rehydrated and boiled in Citrate buffer pH 6.1 (S1699, Dakocytomation, Glostrup, Denmark) for antigen recovery. Endogenous peroxidase was quenched by incubation with 3% $H_2O_2$ in TBS, followed by blocking with 10% goat serum in 2% BSA in TBS—0.1% Tween. Sections were then incubated overnight with antibodies against β-catenin (Cell Signaling, Danvers, Mass.; 9582), cleaved caspase 3 (Cell Signaling; 9661), lysozyme (Dako; A0099), EGFR (sc-03, Santa Cruz Biotechnology, Santa Cruz, Calif.), pTyr705-STAT3 (9145, Cell Signaling), survivin (Cell Signaling; 2808) and synaptophysin (GTX100865, GeneTex Irvine, Calif.), respectively. All sections were further treated with SignalStain® Boost (Cell Signaling; 8114) to detect bound antibody and with liquid3-Amino-9-Ethylcarbazole Chromogen/Substrate (BP 1108, ID LABS™ ON, Canada) for peroxidase staining and counterstained with Haematoxylin (HHS32, Sigma-Aldrich). For BrdU staining, sections were treated with 2 N HCl after antigen recovery, blocked as described above and incubated with anti-BrdU antibody (347580, BD Biosciences) and further with secondary antibody (Invitrogen A-11018) and counterstained with DAPI.

Intestinal Barrier Assessment

Intestinal barrier permeability was assessed as previously described (Chalaris, A. et al., 2010). Briefly, mice were orally gavaged with 60 mg/kg FITC-Dextran (Sigma FD4), food and water were withdrawn 4 h prior to gavage. FITC levels were determined in the serum 4 h post gavage by absorption at 488 nm using standard dilutions of FITC-Dextran as reference.

Statistics

All values represented are mean and SEM. Statistical significance was calculated by unpaired student's t test or ANOVA for parametric observations, while for discontinuous observations like scores for colitis and tumors, significance was evaluated by Mann-Whitney U or Kruskal-Wallis test. All calculations were performed using the GraphPad Prism 5 software.

Results

EGFR Signaling is not Required for Differentiation of IECs

Mice with conditional EGFR deletion in intestinal epithelial cells (IEC) (Egfr$^{\Delta IEC}$) were generated by breeding Egfr$^{f/f}$ mice with Vil-Cre mice that start to express Cre recombinase around E10 (el Marjou, F. et al., 2004). Egfr$^{\Delta IEC}$ mice were born at Mendelian ratios (data not shown). Successful Egfr deletion in IECs was confirmed by immunohistochemistry (IHC; see FIG. 19A) Moreover, IHC demonstrated that many cells in the lamina propria stained positive for EGFR in Egfr$^{f/f}$ and Egfr$^{\Delta IEC}$ mice showing that EGFR is also expressed by non-epithelial cells (see FIG. 19A). IEC specific EGFR deletion was also demonstrated by PCR and Southern blot analysis (see FIGS. 20A and 20B). The mice were viable and displayed no obvious gut abnormalities (see FIG. 20C). In addition to Egfr$^{\Delta IEC}$ mice, hypomorphic Egfr$^{wa2/wa2}$ mice were used which display defective EGFR signaling because of a point mutation in the EGFR (Threadgill, D. W. et al., 1995).

A closer histological examination of the colon revealed no overt morphological and cellular changes in Egfr$^{wa2/wa2}$ and Egfr$^{\Delta IEC}$ mice when compared with controls (see FIG. 20C). The crypts in the small intestine showed proper cellular composition including Lysozyme-expressing paneth cells and Synaptophysin-expressing enteroendocrine cells (see FIG. 20D). These data demonstrate that lack of EGFR signaling does not affect structure and cell differentiation in the intestine.

EGFR Signaling in IECs does not Affect Severity of Colitis

Next the impact of EGFR signaling on DSS-induced colitis in Egfr$^{wa2/wa2}$ and Egfr$^{\Delta IEC}$ mice was investigated (see FIGS. 12A and 12B). Egfr$^{\Delta IEC}$ mice showed no significant loss of body weight during the entire period of DSS administration (see FIG. 12B). Histological analysis revealed that the inflamed colons of Egfr$^{\Delta IEC}$ mice were comparable to those of Egfr$^{f/f}$ mice (see FIGS. 12E, 12F and 12H). These data indicate that EGFR signaling in IECs does not protect from DSS-induced colitis. In contrast to Egfr$^{\Delta IEC}$ mice, DSS administration to Egfr$^{wa2/wa2}$ mice resulted in significant loss of body weight when compared with controls (see FIG. 12A) which was accompanied by diarrhea and presence of blood in the feces (data not shown). In addition, they displayed extensive damage of the colonic mucosa and severe inflammation (see FIGS. 12C, 12D and 12H). These data are consistent with previous studies which describe increased severity of DSS-induced colitis in Egfr$^{wa2/wa2}$ mice (Egger, B. et al., 2000).

EGFR Signaling in Myeloid Cells Protects from Colitis

Egfr$^{wa2/wa2}$ mice harbor hypomorphic EGFR alleles in all body cells including that of the lamina propria. It was reasoned that the obvious difference in the DSS response between Egfr$^{wa2/wa2}$ and Egfr$^{\Delta IEC}$ mice might be due to reduced EGFR signaling in lamina propria cells of Egfr$^{wa2/wa2}$ mice. Therefore, mice deficient for EGFR in myeloid cells (Egfr$^{\Delta MYL}$) were generated by breeding Egfr$^{f/f}$ mice with LysM-Cre mice. As expression of LysM-cre starts early during prenatal development (Clausen, B. E. et al., 1999), it was inferred that Egfr deletion should occur in all myeloid lineages of Egfr$^{\Delta MYL}$ mice in utero including tissue resident macrophages. Conditional deletion of Egfr in myeloid cells was confirmed by PCR and qRT-PCR on genomic DNA and mRNA extracted from cultured bone marrow derived macrophages (BMDM) (see FIGS. 21A and 21B). Interestingly, IHC analysis of DSS-treated colons showed a significant reduction of EGFR expression in lamina propria cells of Egfr$^{\Delta MYL}$ mice (see FIG. 21C), while IECs maintained expression of EGFR. Egfr$^{\Delta MYL}$ mice were born at mendelian ratios and displayed no reduced viability or pathological abnormalities after birth. Histological examination of adult Egfr$^{\Delta MYL}$ mice showed proper development of crypt structure and crypt cellular composition in both colon and small intestine (see FIGS. 21D and 21E).

Next DSS-induced colitis was investigated in Egfr$^{\Delta MYL}$ mice. Similar to Egfr$^{wa2/wa2}$ mice, administration of DSS induced profound weight loss of Egfr$^{\Delta MYL}$ mice (see FIG. 12B) which was accompanied by severe diarrhea and blood in the feces (data not shown). Histological examination showed extensive inflammation with complete loss of the epithelium and large ulcerated regions (see FIGS. 12G and 12H). DSS targets the crypt epithelial cells and alters the intestinal barrier permeability (Wirtz, S. et al., 2007; Chalaris, A. et al., 2010). While the number of ulcers per mouse was comparable between the different EGFR mutant strains (see FIG. 13A), epithelial barrier function measured by oral administration of FITC-Dextran was defective in Egfr$^{\Delta MYL}$ and Egfr$^{wa2/wa2}$ mice. Egfr$^{\Delta MYL}$ and Egfr$^{wa2/wa2}$ mice showed significantly higher levels of FITC-Dextran in the blood serum during colitis (see FIG. 13B) demonstrating loss of barrier integrity. Egfr$^{\Delta IEC}$ mice showed reduced levels of FITC-Dextran in the blood serum which is consistent with a previous study which demonstrated that inhibition of EGFR prevented loss of barrier permeability (Fasano, A., 2012; Tripathi, A. et al., 2009).

Crypt cell proliferation is an important factor contributing to intestinal homeostasis and epithelial regeneration during mucosal injury. Analysis of BrdU incorporation showed significantly reduced BrdU-positive nuclei in the crypts of Egfr$^{\Delta MYL}$ mice when compared with Egfr$^{f/f}$ mice. In contrast, the numbers of proliferating nuclei in Egfr$^{\Delta IEC}$ mice were comparable with genetic controls (see FIG. 13C and FIG. 22A). Moreover, it was stained for cleaved Caspase-3 to investigate apoptosis rates in the colon and no major differences were observed between Egfr$^{\Delta MYL}$ and Egfr$^{\Delta IEC}$ mice (see FIGS. 13D and 22B). These data indicate that EGFR expression in non-epithelial cells is required for proliferation of epithelial cells and mucosal integrity during colitis.

EGFR Signaling in Myeloid Cells Promotes Formation of Colorectal Cancer

Chronic colitis is a significant risk factor for development of colorectal cancer and inhibition of EGFR signaling by cetuximab is used for treatment of metastatic CRC. The occurrence of colon tumors was therefore investigated using the AOM-DSS model for colitis-associated colorectal cancer (Wirtz, S. et al., 2007; Tanaka, T. et al., 2003). Tumor multiplicity and tumor size was similar in Egfr$^{\Delta IEC}$ and Egfr$^{f/f}$ mice indicating that EGFR signaling in epithelial cells is not required for CRC formation. Similarly, ubiquitous reduction of EGFR activity in Egfr$^{wa2/wa2}$ mice did not affect tumor incidence or multiplicity when compared with Egfr$^{wa2/+}$ control mice (see FIGS. 14A and 14B) which is consistent with a previous study (Dube, P. E. et al., 2012). However, tumors of Egfr$^{wa2/wa2}$ mice were significantly smaller than tumors of Egfr$^{wa2/+}$ mice (see FIGS. 14C and 14D). In contrast, EGFR ablation in myeloid cells led to a significant reduction in overall tumor incidence and multiplicity with most tumors localized in the most distal colon (see FIGS. 14A to 14D). Moreover, 50-70% of mice remained tumor-free in Egfr$^{\Delta MYL}$ and Egfr$^{wa2/wa2}$ mice, respectively (see FIG. 23A). These data indicate that EGFR signaling in myeloid cells is required for CRC formation. Tumors in all genotypes were predominantly low-grade adenomatous lesions, with Egfr$^{\Delta MYL}$ mice having the highest proportion (see FIGS. 14E and 23B). Only a minor percentage of tumors progressed to high-grade adenomas or adenocarcinomas.

BrdU- and cleaved Caspase-3-staining was performed to assess the molecular mechanism for reduced tumor formation in Egfr$^{wa2/wa2}$ and Egfr$^{\Delta MYL}$ mice. No major difference in proliferation was observed between Egfr$^{\Delta IEC}$, Egfr$^{wa2/wa2}$ and Egfr$^{\Delta MYL}$ tumors (see FIGS. 14F and 24A). However, the rate of apoptosis as determined by cleaved Caspase-3-staining showed a significant increase of apoptotic cells in tumors of Egfr$^{wa2/wa2}$ and Egfr$^{\Delta MYL}$ mice (see FIGS. 14G and 24B). These data indicate that EGFR signaling in stromal myeloid cells supports survival of CRC cells thereby promoting tumorigenesis.

EGFR Signaling in Myeloid Cells Promotes STAT3 Activation in Colorectal Tumor Cells Various independent studies have demonstrated that activation of the transcription factor STAT3 promotes CRC formation (Bollrath, J. et al., 2009(a); Chalaris, A. et al., 2009; Grivennikov, S. et al., 2009; Becker, C. et al., 2005; Bromberg, J. et al., 2009; Lee, M. J. et al., 2012; Rigby, R. J. et al., 2007; Yu, H. et al., 2009; Grivennikov, S. I. et al., 2011; Bollrath, J. et al., 2009(b)). STAT3 activation was therefore assessed in mouse tumors by IHC for tyrosine-705-phosphorylated STAT3 (pY-Stat3). Interestingly, epithelial ablation of EGFR did not affect STAT3 activation and Egfr$^{\Delta IEC}$ mice showed comparable numbers of pY-STAT3 positive nuclei when compared with controls. In contrast, tumors from Egfr$^{wa2/wa2}$ mice and Egfr$^{\Delta MYL}$ mice showed significant reduction of nuclear pY-STAT3 when compared with corresponding control mice (see FIGS. 15A and 15D). Moreover, Egfr$^{wa2/wa2}$ and Egfr$^{\Delta MYL}$ tumors showed decreased expression of the anti-apoptotic protein Survivin, a downstream target of STAT3 (see FIGS. 15B and 15E). These data indicate that EGFR signaling in myeloid stromal cells promotes STAT3 activation and STAT3-dependent expression of Survivin in colorectal tumor cells. Interestingly, activation of β-Catenin was elevated in Egfr$^{wa2/wa2}$ and Egfr$^{\Delta MYL}$ tumors when compared with corresponding control and Egfr$^{\Delta IEC}$ tumors. This response might represent a compensatory reaction triggered by loss of oncogenic STAT3 activity (see FIGS. 15C and 15F).

EGFR Signaling in Myeloid Cells of Apc$^{Min/+}$ Mice Promotes Formation of Intestinal Tumors Next the role of EGFR signaling was investigated in Apc$^{Min/+}$ mice, an independent model for formation of intestinal tumors. Similar to the AOM-DSS model, no significant decrease in tumor multiplicity or tumor size was observed in Apc$^{Min/+}$ Egfr$^{\Delta IEC}$ mice. In contrast, Apc$^{Min/+}$ Egfr$^{\Delta MYL}$ mice showed a trend towards decreased tumor incidence and multiplicity (see FIG. 16A). However, the whole tumor load and the average size of Apc$^{Min/+}$ Egfr$^{\Delta MYL}$ tumors was significantly reduced when compared with controls (see FIGS. 16B and 16C). These data indicate that EGFR signaling in myeloid stromal cells promotes formation of intestinal tumors in Apc$^{Min/+}$ mice.

EGFR Signaling in Myeloid Cells Promotes STAT3 Activation Via Regulation of IL-6 Production Lamina propria cells secrete various pro-survival factors during inflammation that support epithelial regeneration. Among those factors is IL-6, a potent inducer of STAT3 activation (Gabay, C., 2006; Grivennikov, S. et al., 2009; Becker, C. et al., 2005; Bromberg, J. et al., 2009; Lee, M. J. et al., 2012; Grivennikov, S. I. et al., 2011; Neurath, M. F. et al., 2011; Reinecker, H. C. et al., 1993). IL-6 levels were measured because it has been demonstrated that IL-6/STAT3 protects from DSS-induced colitis (Grivennikov, S. et al., 2009). Interestingly, serum IL-6 levels were significantly reduced in Egfr$^{wa2/wa2}$ and Egfr$^{\Delta MYL}$ mice (see FIG. 17A) but not in Egfr$^{\Delta IEC}$ mice. This data indicates that the observed phenotypes of Egfr$^{wa2/wa2}$ and Egfr$^{\Delta MYL}$ mice in colitis and tumor formation are due to reduced IL-6 production by EGFR-deficient myeloid cells. To test this hypothesis, recombinant IL-6 was administered orally during DSS treatment. Importantly IL-6 was able to protect Egfr$^{\Delta MYL}$ mice from DSS-induced weight loss (see FIG. 17B) while Egfr$^{wa2/wa2}$ mice were partially rescued. Although the severity of inflammation was similar in all genotypes (see FIG. 17C), administration of IL-6 decreased the number of ulcers in Egfr$^{\Delta MYL}$ mice (see FIG. 17D) and protected from loss of epithelial barrier function (see FIG. 17E).

IL-6 treatment was also able to fully and partially restore epithelial proliferation during colitis in Egfr$^{\Delta MYL}$ and Egfr$^{wa2/wa2}$ mice, respectively (see FIGS. 18A and 26A), whereas apoptosis was not affected (see FIGS. 18B and 26B). Interestingly, IL-6 decreased apoptosis in Egfr$^{\Delta IEC}$ mice which might be a due to a cell autonomous effect. pY-STAT3 nuclear localization was significantly reduced during DSS treatment in crypts of vehicle treated Egfr$^{\Delta MYL}$ mice (see FIGS. 18C and 18D) which was fully restored upon IL-6 administration. These results demonstrate that EGFR signaling in myeloid cells promotes release of IL-6 which stimulates STAT3 activation in IECs in a paracrine manner. pY-STAT3 further promotes IEC proliferation and inhibits apoptosis via positive regulation of Survivin expression.

Discussion

Extensive studies have yielded considerable knowledge on the role of EGFR in many organs including the intestine, where it was shown that EGFR total KO mice display a wide range of intestinal abnormalities at birth, like stunted villi, distended loops, intestinal hemorrhage and necrotizing enterocolitis (Miettinen, P. J., 1995). These abnormalities are also influenced by the mouse background (Sibilia, M. et al., 1995; Threadgill, D. W. et al., 1995). As the currently available literature describing conditional Egfr targeting have been performed selectively with either epithelial or myeloid lineage in actue colitis alone by selectively ablating EGFR expression in both epithelial and non-epithelial tissues, in the context of the present invention it has been established for the first time that the expression of EGFR on myeloid cells is the crucial factor that determines the progression in chronic colitis and the likelihood of developing CAC, while loss of EGFR expression on IECs does not majorly influence disease outcome (Yan, F. et al., 2011; Rowland, K. J. et al., 2012; Dube, P. E. et al., 2012). Although the loss of EGFR on myeloid cells increases the severity of colitis, the immense outcome lies in impeding tumor development due to chronic colitis.

The role of EGFR in IBD is both intriguing and complex, the protective effect of an active EGFR signaling is described by results from Egger et al. where $Egfr^{Wa2/Wa2}$ mice are more sensitive to acute colitis. However more recent studies which employed selective gene ablation have showed the requirement of EGFR on IECs as redundant in both experimental colitis and small bowel resection (Yan, F. et al., 2011; Rowland, K. J. et al., 2012). Although EGFR expression on non-epithelial cells (such as cells of the immune system) has been previously reported (Rowland, K. J. et al., 2012; Playford, R. J. et al., 1996; Yoo, J. et al., 2012), attempts to understand its role on these cells have only recently been made (Lu, N. et al., 2014). This study by Lu et. al. showed the presence of activated EGFR on macrophages of experimental colitis mice and that its specific deletion on macrophages alleviated colitis via increased IL-10 production. However, this contravenes the results from Yan et. al. where activation of EGFR by administration of probiotics to $Egfr^{f/f}$ VilCre mice failed to protect against DSS mediated colitis injury (Yan, F. et al., 2011), as robust activation of EGFR should still occur in the macrophages of these mice (which still express EGFR) due to increased relative availability of probiotic, which should lower IL-10 levels, yet no difference in IL-10 expression was observed.

Additionally, in a clinical study involving ulcerative colitis patients, direct stimulation of EGFR in the colon via EGF enemas induced disease remission (Sinha, A. et al., 2003). Also, a study that investigated experimental colitis in mice harboring selective deletion of EGFR downstream target gene Cox-2 on myeloid cells reported an increase in colitis severity (Ishikawa, T. O. et al., 2011). Such contradictory results further perturb the knowledge of EGFR both in disease and during recovery, thereby underscoring the need to dissect further its mode of action in a cell specific manner as until now, characterization of EGFR in the gut has mainly been restricted to IECs. The influence of EGFR expression on myeloid cells in colitis was recently described by Lu et al. (Lu, N. et al., 2014). Although a similar decrease in the IL-6 levels in $Egfr^{\Delta MYL}$ mice has also been observed in the present study, contrary to their conclusions whereby conditional ablation of Egfr in macrophages alleviated inflammation and promoted recovery, the results provided herein demonstrate that the protective function exerted on IECs by EGFR is indirectly via its activation on cells of myeloid origin, which might lead to the secretion of IL-6. Also as DSS induces colitis by exposing the immune cells of the lamina propria to luminal microorganisms via erosion of the colonic epithelium, these differences in observations might be influenced due to different animal housing conditions and environment on the composition of gut microflora and heterogeneity within the mice. Additionally the observations made herein conform with a recently published study where deletion of an EGFR downstream target gene Cox-2 in myeloid cells was shown to exacerbate colitis (Ishikawa, T. O. et al., 2011). However, an influence of EGFR expression on endothelial cells on the outcome in colitis can currently not be excluded.

The IL-6 family of cytokines has been described to play a pro-proliferative role in many inflammation driven cancers and regulate epithelial barrier function (Chalaris, A. et al., 2009; Gabay, C., 2006; Grivennikov, S. et al., 2009; Jin, X. et al., 2010; Putoczki, T. L. et al., 2013; Becker, C. et al., 2005; Bromberg, J. et al., 2009; Grivennikov, S. I. et al., 2011; Neurath, M. F. et al., 2011; Reinecker, H. C. et al., 1993; Becker, C. et al., 2004; Fenton, J. I. et al., 2006; Ishihara, K. et al., 2002; Rollwagen, F. M. et al., 1998; Scheller, J. et al., 2006; Yu, M. et al., 2002; Zimmers, T. A. et al., 2003a; Zimmers, T. A. et al., 2003b). As $ll6^{-/-}$ mice exposed to colitis have been shown to have a defect in proliferation of IECs, similar to what has presently been observed in $Egfr^{\Delta MYL}$ mice, which have reduced systemic level of IL-6. As IL-6 is mainly produced by the innate immune cells of the lamina propria which promotes survival and proliferation of IECs, it is considered that selective deletion of EGFR in these cells of myeloid origin renders them unable to secrete IL-6. In addition, no apparent differences have been observed in response of $Egfr^{\Delta IEC}$ mice to DSS treatment in terms of weight loss and proliferation of IECs. This effect can be attributed to the expression of EGFR on the lamina propria cells of these mice, which are able to secrete IL-6, thereby inducing epithelial proliferation and subsequently, healing of the wounds caused by DSS. This inference is also supported by the results of previous independent investigations, where EGFR expression on IECs was dispensable in both during colitis and after surgical resection. In addition, the lack of EGFR in IECs in these mice may also contribute to greater barrier integrity as EGFR inhibition has been shown to prevent increase in barrier permeability (Tripathi, A. et al., 2009; Becker, C. et al., 2005).

The role of EGFR as a tumor promoter is highlighted by studies that describe its expression on IECs as a requirement for tumor formation in CAC (Fichera, A. et al., 2007; Cohen, G. et al., 2006; Dougherty, U. et al., 2009; Roberts, R. B. et al., 2002). Though these investigations have considerably expanded the knowledge of EGFR in such diseases, their results have to be viewed with caveat as they been derived from in mouse models where tumor formation is facilitated by constitutively active Beta-catenin, or due to consumption of excess fat which is known to influence tumor development. Perhaps the combination of EGFR signaling in addition to these secondary factors might facilitate in providing an ideal niche for tumor formation. Indeed, a recent study using $Egfr^{wa2/wa2}$ mice showed that ubiquitous reduction in the EGFR activity in $Egfr^{wa2/wa2}$ mice did not affect tumor incidence or multiplicity (Dube, P. E. et al., 2012). The results provided herein also show that EGFR expression on the lamina propria cells facilitates development of tumors upon treatment with AOM and DSS, while its absence on IECs has no such influence. Although a decrease in EGFR signaling showed no apparent effect on tumor incidence in $Egfr^{wa2/wa2}$ mice, it led to a significant reduction in tumor growth. However, complete abolition of EGFR on myeloid cells led to a dramatic decrease in both the tumor number and tumor growth. Tumor progression was also delayed in $Egfr^{\Delta MYL}$ mice, as they showed a high percentage of low grade adenomas when compared to $Egfr^{f/f}$ and $Egfr^{\Delta IEC}$ mice. The activation of STAT3 signaling by IL-6 family cytokines has been described earlier as paramount for the survival and subsequent proliferation of mutated IECs in mice administered with AOM (Bollrath, J. et al., 2009(a);

Grivennikov, S. et al., 2009; Putoczki, T. L. et al., 2013; Yoo, J. et al., 2012; Grivennikov, S. I. et al., 2011; Bollrath, J. et al., 2009(b)). It is considered that the absence of EGFR on the lamina propria of Egfr$^{\Delta MYL}$ mice leads to reduced survival of the preneoplastic IECs caused by AOM, due to lack of IL-6, elevated systemic levels of IL-6 have been linked to poor clinical outcome in humans (Grivennikov, S. I. et al., 2011). Additionally, the reduced nuclear STAT3 signaling observed in tumors of Egfr$^{\Delta MYL}$ mice supports the results provided herein of an IL-6 deficiency in these mice which drives tumor growth (Bollrath, J. et al., 2009(a); Gabay, C., 2006; Musteanu, M. et al., 2010; Bromberg, J. et al., 2009; Yu, H. et al., 2009; Grivennikov, S. I. et al., 2011; Scheller, J. et al., 2006; Quesnelle, K. M. et al., 2007). Decrease in expression of the STAT3 target survivin in tumors of mice lacking EGFR signaling in myeloid cells further illustrates the increased apoptosis, possibly leading to reduced tumor sizes, as survivin being a member of inhibitor of apoptosis family, prevents cell death by blocking caspases (Fan, Y. et al., 2008; Krieg, A. et al., 2013; Lassmann, S. et al., 2007; Zhu, Y. et al., 2013), with its increased expression leading to poor clinical outcomes. Furthermore, the decrease in STAT3 signaling observed in AOM/DSS induced tumors of Egfr$^{\Delta MYL}$ mice is further corroborated by the reduction in overall tumor burden in Apc$^{Min/+}$Egfr$^{\Delta MYL}$ mice, which is in accordance with the results of Musteanu et al. whereby STAT3 signaling was shown to be essential for promoting tumorigenesis during initial stages in Apc$^{Min/+}$ mice, yet impairing tumor progression at later stages (Musteanu, M. et al., 2010).

Finally oral replenishment of IL-6 in Egfr$^{\Delta MYL}$ mice led to considerable protection against intestinal damage caused due to DSS, in short via re-establishment of STAT3 signaling in the IECs, and most importantly aiding in restoration of proliferation. STAT3 activation by EGFR via IL-6 receptor (IL-6R) has been described previously in cell lines derived from human cancers (Colomiere, M. et al., 2009; Gao, S. P. et al., 2007). However, it has never been investigated in vivo. Therefore, the observations made herein for the first time describe the necessity of EGFR signaling on myeloid cells for IL-6 production during intestinal inflammation. However, it can currently not be ruled out that a deficiency in other IL-6 family cytokines in these mice caused due to EGFR deletion on myeloid cells, which activate STAT3 (Putoczki, T. L. et al., 2013) or compensation in signaling by other ErbB family RTKs. The characterization of many RTKs including EGFR have mainly been carried on epithelial tissues, their roles on immune cells is yet to be addressed. The need to dissect their role is highly imperative, as it has been described that inhibition of IL-6 signaling leads to decreased EGF mediated migration in human ovarian cancer cell lines (Colomiere, M. et al., 2009). In addition, activating mutations in EGFR have been shown to cause increased IL-6 production in human lung cancer (Gao, S. P. et al., 2007).

Targeting the ErbB family of RTKs remains one of the most favored anti-tumor therapies currently in practice, as they are one of the most frequently deregulated in many cancers. A recently published meta-analysis comparing the efficacies of pharmacological inhibitors in patients with advanced non-small-cell lung cancer described increased drug toxicity in the form of diarrhea, a classic symptom of colitis, in the group treated with erlotinib and gefitinib, in addition to other adverse effects (Liang, W. et al., 2014). A previous study using an in vitro model showed that pharmacological inhibition of ADAM-17 in wounded rat IECs resulted in a dose dependent decrease of EGFR phosphorylation which was required for epithelial regeneration, due to inhibition of TGFα release (Myhre, G. M. et al., 2004). A more recent study employing mice expressing a hypomorphic ADAM17 (Adam17$^{ex/ex}$) described extensively its role in IBD (Chalaris, A. et al., 2010). These mice showed increased susceptibility to DSS treatment with severe weight loss, inflammation, extensive damage of the colonic mucosa, decreased proliferation and increased permeability of intestinal barrier, a phenotype similar to Egfr$^{\Delta MYL}$ mice. This increased susceptibility to colitis was due to inability to cleave EGFR activating ligands, as exogenous supplementation of TGFα lead to a partial rescue of the symptoms (Chalaris, A. et al., 2010).

The results provided herein underscore the need for a more targeted cell specific anti-tumor therapy unlike the conventional approach, which also entails pervasive effects, as the treatment does not always lead to a favorable outcome. Furthermore, the present results indicate that the determination of the expression of EGFR in myeloid cells can advantageously be used to identify those patients suffering from inflammation-associated cancer such as colorectal cancer who are susceptible to the treatment with an EGFR inhibitor/antagonist. The present invention thus provides an improved personalized therapy of inflammation-associated cancer such as colorectal cancer, which is to be expected to yield improved clinical results, particularly in patients having CD68-positive myeloid cells in the inflammation-associated cancer tissue.

REFERENCES

Amado, R. G. et al. *J Clin Oncol* 26(10), 1626-1634 (2008).
Becker, C. et al. *Immunity* 21(4), 491-501 (2004).
Becker, C. et al. *Cell Cycle* 4(2), 217-220 (2005).
Ben-Neriah, Y. et al. *Nat Immunol* 12(8), 715-723 (2011).
Blobel, C. P. *Nat Rev Mol Cell Biol* 6, 32-43 (2005).
Bokemeyer, C. et al. *Ann Oncol* 22(7), 1535-1546 (2011).
Bollrath, J. et al. *Cancer Cell* 15(2), 91-102 (2009) (a).
Bollrath, J. et al. *EMBO Rep* 10(12), 1314-1319 (2009) (b).
Bret, P. M. et al. *Can Assoc Radiol J* 37, 5-8 (1986).
Bromberg, J. et al. *Cancer Cell* 15(2), 79-80 (2009).
Buckley, A. F. et al. *Am J Clin Pathol* 129, 245-251 (2008).
Caturelli, E. et al. *Gut* 53(9), 1356-1362 (2004).
Chalaris, A. et al. *Dig Dis* 30(5), 492-499 (2009).
Chalaris, A. et al. *J Exp Med* 207(8), 1617-1624 (2010).
Chen, W. C. et al. *Liver Int* 30(10), 1548-1549 (2010).
Chen, X. et al. *N Am J Med Sci* 2(5), 241-245 (2010).
Clausen, B. E. et al. *Transgenic Res* 8(4), 265-277 (1999).
Cohen, G. et al. *Cancer Res* 66(11), 5656-5664 (2006).
Cole, S. P. C. et al. *Monoclonal Antibodies and Cancer Therapy* 27, 77-96 (1985).
Colomiere, M. et al. *Br J Cancer* 100(1), 134-144 (2009).
Coussens, L. M. et al. *Nature* 420, 860-867 (2002).
Danese, S. et al. *Oncogene* 29(23), 3313-3323 (2010).
Das, M. et al. *Genes Dev* 25, 634-645 (2011).
Degryse, B. et al. *J Cell Biol* 152, 1197-1206 (2001).
Ding, C. et al. *J Biochem Mol Biol* 37(1), 1-10 (2004).
Dougherty, U. et al. *Clin Cancer Res* 15(22), 6780-6789 (2009).
Drobits, B. et al. *The Journal of clinical investigation* 122, 575-585 (2012).
Dube, P. E. et al. *J Clin Invest* 122(8), 2780-2792 (2012).
Eaden, J. A. et al. *Gut* 48(4), 526-535 (2001).
Eales-Reynolds, L. J. et al. *Cytokine* 16(5), 169-172 (2001).
EASL-EORTC clinical practice guidelines: management of hepatocellular carcinoma. *Journal of hepatology* 56, 908-943 (2012).

Edoute, Y. et al. *J Surg Oncol* 48, 246-251 (1991).
Edoute, Y. et al. *Am J Gastroenterol* 87, 1138-1141 (1992).
Eferl, R. et al. *Cell* 112, 181-192 (2003).
Egger, B. et al. *Scand J Gastroenterol* 35(11), 1181-1187 (2000).
Eisenhauer, E. A. et al. *Eur J Cancer* 45(2), 228-247 (2009).
Ekbom, A. et al. *N Engl J Med* 323(18), 1228-1233 (1990).
el Marjou, F. et al. *Genesis* 39(3), 186-193 (2004).
Epstein et al. Proc Natl Acad Sci USA 82, 3688-3692 (1985).
Fan, Y. et al. *World journal of gastroenterology: WJG* 14(3), 428-434 (2008).
Fasano, A. *Annals of the New York Academy of Sciences* 1258, 25-33 (2012).
Faulkner, N. E. et al. *ASCO Meeting on Molecular Markers*, abstract no. 96 (2010).
Feitelson, M. A. et al. *Surg Clin North Am* 84, 339-354 (2004).
Fenton, J. I. et al. *Carcinogenesis* 27(7), 1507-1515 (2006).
Fichera, A. et al. *Cancer Res* 67(2), 827-835 (2007).
Finkin, S. et al. *Current topics in microbiology and immunology* 349, 185-196 (2011).
Franzke, C. W. et al. *J Exp Med* 209(6), 1105-1119 (2012).
Gabay, C. *Arthritis Res Ther* 8 Suppl 2, S3 (2006).
Gan, H. K. et al. *FEBS J* 280(21), 5350-5370 (2013).
Gao, S. P. et al. *J Clin Invest* 117(12), 3846-3856 (2007).
Garlanda, C. et al. *Cancer Res* 67(13), 6017-6021 (2007).
Gerry, N. P. et al. *J Mol Biol* 292(2), 251-62 (1999).
Green, M. R. et al. Molecular Cloning: A Laboratory Manual. Cold Spring Harbor Laboratory Press. Fourth Edition. 2012. ISBN: 978-1936113422.
Grivennikov, S. et al. *Cancer Cell* 15(2), 103-113 (2009).
Grivennikov, S. I. et al. *Cell* 140, 883-899 (2010).
Grivennikov, S. I. et al. *Ann Rheum Dis* 70 Suppl 1, i104-i108 (2011).
Guo, Z. et al. *Diagn Cytopathol* 26, 283-289 (2002).
Gupta, R. B. et al. *Gastroenterology* 133(4), 1099-1105 (2007).
Hanahan, D. et al. *Cancer Cell* 21(3), 309-322 (2012).
Harlow, E. et al. Using Antibodies: A Laboratory Manual. Cold Spring Harbor Laboratory Press. 1998. ISBN: 978-0879695446.
He, G. et al. *Cell Res* 21, 159-168 (2011).
Heinrichsdorff, J. et al. *EMBO reports* 9, 1048-1054 (2008).
Helmrath, M. A. et al. *J Surg Res* 69(1), 76-80 (1997).
Ho, C. S. et al. *Cancer* 47, 1781-1785 (1981).
Hobbs, S. S. et al. *Am J Physiol Gastrointest Liver Physiol* 301(2), G220-G229 (2011).
Hoechst, B. et al. *Gastroenterology* 135(1), 234-243 (2008).
Holness, C. L. et al. *Blood* 81(6), 1607-1613 (1993).
Hopfner, M. et al. *J Hepatol* 41, 1008-1016 (2004).
Hui, L. et al. *Nat Genet* 39, 741-749 (2007).
Hui, L. et al. *The Journal of clinical investigation* 118, 3943-3953 (2008).
Hwang et al. Proc Natl Acad Sci USA 77, 4030-4034 (1980).
Ikarashi, M. et al. *J Leukoc Biol* 94(6), 1325-1336 (2013).
Ishihara, K. et al. *Cytokine Growth Factor Rev* 13(4-5), 357-368 (2002).
Ishikawa, T. O. et al. *Carcinogenesis* 32(3), 417-426 (2011).
Jemal, A. et al. *CA: a cancer journal for clinicians* 61, 69-90 (2011).
Jin, X. et al. *Gut* 59(2), 186-196 (2010).
Keohavong, P. et al. *Clin Cancer Res* 2(2), 411-418 (1996).
Key, M. Immunohistochemical staining methods: education guide. 2006.
Kim, S. et al. *Cancer Res* 68(1), 323-328 (2008).
Köhler, G. et al. *Nature* 256(5517), 495-497 (1975).
Kozbor, D. et al. *Immunol Today* 4(3), 72-79 (1983).
Krieg, A. et al. *PLoS One* 8(6), e65338 (2013).
Langer, R. et al. *J Biomed Mater Res* 15, 167-277 (1981).
Langer, R. ChemTech 12, 98-105 (1982).
Lassmann, S. et al. *Journal of clinical pathology* 60(2), 173-179 (2007).
Laurent-Puig, P. et al. *Oncogene* 25, 3778-3786 (2006).
Lee, C. H. et al. *Mol Cancer* 9(1), 64 (2010).
Lee, M. J. et al. *PLoS One* 7(9), e38801 (2012).
Li, H. P. et al. *Carcinogenesis* 34, 2443-2451 (2013).
Liang, W. et al. *PLoS One* 9(2), e85245 (2014).
Lichtenberger, B. M. et al. *Cell* 140, 268-279 (2010).
Llovet, J. M. et al. *Semin Liver Dis* 19(3), 329-338 (1999).
Lu, N. et al. *J Immunol* 192(3), 1013-1023 (2014).
Luedde, T. et al. *Cancer Cell* 11, 119-132 (2007).
Luetteke, N.C. et al. *Cell* 73(2), 263-278 (1993).
Luetteke, N.C. et. al. *Genes Dev* 8(4), 399-413 (1994).
Maeda, S. et al. *Cell* 121, 977-990 (2005).
Mallarkey, G. et al. *Therapeutic advances in medical oncology* 5, 5-16 (2013).
Mann, G. B. et al. *Cell* 73(2), 249-261 (1993).
Matsumoto, S. et al. *J Immunol* 184(3), 1543-1551 (2010).
Mazzaferro, V. et al. *The New England journal of medicine* 334, 693-699 (1996).
McElroy, S. J. et al. *PloS one* 7, e38373 (2012).
Michielsen, P. P. et al. *Acta Gastroenterol Belg* 61, 158-163 (1998).
Miettinen, P. J. *Nature* 376(6538), 337-341 (1995).
Murdoch, C. et al. *Nat Rev Cancer* 8(8), 618-631 (2008).
Musteanu, M. et al. *Gastroenterology* 138(3), 1003-1011 e1-5 (2010).
Myhre, G. M. et al. *Am J Physiol Gastrointest Liver Physiol* 287(6), G1213-G1219 (2004).
Naito, M. et al. *Microsc Res Tech* 39(4), 350-364 (1997).
Naito, M. et al. *Med Electron Microsc* 37(1), 16-28 (2004).
Natarajan, A. et al. Proc Natl Acad Sci USA 104, 17081-17086 (2007).
Naugler, W. E. et al. *Science* 317, 121-124 (2007).
Neurath, M. F. et al. *Cytokine Growth Factor Rev* 22(2), 83-89 (2011).
Peeters, M. et al. *J Clin Oncol* 28(31), 4706-4713 (2010).
Peschon, J. J. et al. *Science* 282(5392), 1281-1284 (1998).
Pilotti, S. et al. *Acta Cytol* 32, 27-38 (1988).
Playford, R. J. et al. *Gut* 39(2), 262-266 (1996).
Pons, F. et al. *HPB (Oxford)* 7(1), 35-41 (2005).
Putoczki, T. L. et al. *Cancer Cell* 24(2), 257-271 (2013).
Quesnelle, K. M. et al. *J Cell Biochem* 102(2), 311-319 (2007).
Reinecker, H. C. et al. *Clin Exp Immunol* 94(1), 174-181 (1993).
Renshaw, S. Immunohistochemistry: Methods Express. Scion Publishing Ltd, Bloxham (UK). 2007. ISBN: 9781904842033.
Rigby, R. J. et al. *Oncogene* 26(33), 4833-4841 (2007).
Roberts, R. B. et al. Proc Natl Acad Sci USA 99(3), 1521-1526 (2002).
Rollwagen, F. M. et al. *Clin Immunol Immunopathol* 89(3), 205-213 (1998).
Rowland, K. J. et al. *J Pediatr Surg* 47(9), 1748-1753 (2012).
Roxana, A. *Maedica* 1(1), 63-65 (2006).
Rutter, M. et al. *Gastroenterology* 126(2), 451-459 (2004).
Sakurai, T. et al. Proc Natl Acad Sci USA 103, 10544-10551 (2006).
Sakurai, T. et al. *Cancer Cell* 14, 156-165 (2008).
Samaratunga, H. et al. *Aust NZ J Surg* 62, 540-544 (1992).
Scheller, J. et al. *Scand J Immunol* 63(5):321-329 (2006).

Schiffer, E. et al. *Hepatology* 41, 307-314 (2005).
Schubbert, S. et al. *Nat Rev Cancer* 7(4), 295-308 (2007).
Sell, S. *Semin Cell Dev Biol* 13, 419-424 (2002).
Shacter, E. et al. *Oncology (Williston Park)* 16(2), 217-226 (2002).
Sibilia, M. et al. *Science* 269(5221), 234-238 (1995).
Sibilia, M. et al. *Cell* 102, 211-220 (2000).
Sidman, U. et al. *Biopolymers* 22, 547-556 (1983).
Sieghart, W. et al. *J Hepatol* 54, 89-97 (2011).
Sinha, A. et al. *N Engl J Med* 349(4), 350-357 (2003).
Smedsrod, B. et al. *Journal of leukocyte biology* 38, 213-230 (1985).
Stintzing, S. et al. *Dtsch Arztebl Int* 106(12), 202-206 (2009).
Tanaka, T. et al. *Cancer Sci* 94(11), 965-973 (2003).
Taylor, P. C. *Curr Opin Pharmacol* 3(3), 323-328 (2003).
Terzic, J. et al. *Gastroenterology* 138(6), 2101-2114 e5 (2010).
Threadgill, D. W. et al. *Science* 269(5221), 230-234 (1995).
Tripathi, A. et al. *Proc Natl Acad Sci USA* 106(39), 16799-16804 (2009).
Vainer, G. W. et al. *Cancer Lett* 267, 182-188 (2008).
Wang, K. et al. *Hepatology* 52, 164-173 (2010).
Wang, S. N. et al. *European journal of clinical investigation* 42, 1295-1301 (2012).
Whittaker, S. et al. *Oncogene* 29, 4989-5005 (2010).
Wiedmann, M. W. et al. *Curr Cancer Drug Targets* 11(6), 714-733 (2011).
Wirtz, S. et al. *Nature protocols* 2(3), 541-546 (2007).
Wikstrand, C. J. et al. *J Neurovirol* 4(2), 148-158 (1998).
Wright, N. A. et al. *Nature* 343(6253), 82-85 (1990).
Yamaoka, T. et al. *Proc Natl Acad Sci USA* 105(33), 11772-11777 (2008).
Yan, F. et al. *J Clin Invest* 121(6), 2242-2253 (2011).
Yarden, Y. et al. *Nat Rev Mol Cell Biol* 2(2), 127-137 (2001).
Yoo, J. et al. *Am J Physiol Gastrointest Liver Physiol* 302(8), G805-G814 (2012).
Yu, M. et al. *Toxicol Sci* 68(2), 488-497 (2002).
Yu, H. et al. *Nat Rev Cancer* 9(11), 798-809 (2009).
Zhu, Y. et al. *PLoS One* 8(9), e74778 (2013).
Zimmers, T. A. et al. *Hepatology* 38(2), 326-334 (2003) (a).
Zimmers, T. A. et al. *Hepatology* 38(6), 1590-1591 (2003) (b), author reply 1.

---

The invention claimed is:

1. A method of testing a subject for the need of treatment of an inflammation-associated cancer, wherein the subject has or is suspected of having said cancer, and wherein the inflammation-associated cancer is hepatocellular carcinoma or an inflammation-associated intestinal cancer, the method comprising the steps of:
   (a) obtaining a sample from the subject that comprises a myeloid cell population, wherein the myeloid cells in the myeloid cell population are CD68-positive macrophage cells and/or Kupffer cells and are from within said cancer or from the tissue adjacent to said cancer;
   (b) testing the myeloid cell population to identify that portion of myeloid cells that detectably express EGFR, wherein greater than 5% of myeloid cells in the myeloid cell population detectably express EGFR; and
   (c) treating the subject by administering a therapeutically effective amount of an EGFR inhibitor/antagonist to the subject.

2. The method of claim 1, wherein the subject is a human.

3. The method of claim 1, wherein greater than 10% of myeloid cells in the myeloid cell population detectably express EGFR.

4. The method of claim 3, wherein greater than 20% of myeloid cells in the myeloid cell population detectably express EGFR.

5. The method of claim 4, wherein greater than 30% of myeloid cells in the myeloid cell population detectably express EGFR.

6. The method of claim 1, wherein the sample is a cancer tissue biopsy sample.

7. The method of claim 1, wherein the myeloid cells are CD68-positive macrophage cells.

8. The method of claim 1, wherein the inflammation-associated cancer is hepatocellular carcinoma.

9. The method of claim 1, wherein the sample is a liver tissue sample.

10. The method of claim 1, wherein the myeloid cells are Kupffer cells.

11. The method of claim 1, wherein the inflammation-associated cancer is colorectal cancer.

12. The method of claim 11, wherein the sample is a colorectal tissue sample or a colorectal polyp.

13. The method of claim 1, wherein the myeloid cells are identified by determining a level of translation of EGFR therein.

14. The method of claim 13, wherein the level of translation is determined using an immunohistochemical method, an enzyme-linked immunosorbent assay, or a radioimmunoassay.

15. The method of claim 1, wherein the EGFR inhibitor/antagonist is selected from the group consisting of gefitinib, erlotinib, lapatinib, afatinib, neratinib, ABT-414, dacomitinib, AV-412, PD 153035, vandetanib, PKI-166, pelitinib, canertinib, icotinib, poziotinib, BMS-690514, CUDC-101, AP26113, XL647, cetuximab, panitumumab, zalutumumab, nimotuzumab, matuzumab, and a pharmaceutically acceptable salt thereof.

* * * * *